US011291691B2

(12) United States Patent
Peltz et al.

(10) Patent No.: US 11,291,691 B2
(45) Date of Patent: *Apr. 5, 2022

(54) METHODS AND COMPOSITIONS FOR PRODUCING HEPATOCYTE-LIKE CELLS

(71) Applicant: The Board of Trustees of the Leland Stanford Junior University, Stanford, CA (US)

(72) Inventors: Gary Peltz, Redwood City, CA (US); Dan Xu, Fremont, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 446 days.

This patent is subject to a terminal disclaimer.

(21) Appl. No.: 15/974,377

(22) Filed: May 8, 2018

(65) Prior Publication Data

US 2019/0083545 A1    Mar. 21, 2019

Related U.S. Application Data

(63) Continuation of application No. 14/917,558, filed as application No. PCT/US2014/056049 on Sep. 17, 2014, now Pat. No. 10,004,767.

(60) Provisional application No. 61/880,056, filed on Sep. 19, 2013.

(51) Int. Cl.
```
A61K 35/407    (2015.01)
C12N 5/071     (2010.01)
C12N 5/074     (2010.01)
```

(52) U.S. Cl.
CPC .......... *A61K 35/407* (2013.01); *C12N 5/067* (2013.01); *C12N 5/0696* (2013.01); *C12N 2500/62* (2013.01); *C12N 2501/119* (2013.01); *C12N 2501/12* (2013.01); *C12N 2501/155* (2013.01); *C12N 2501/16* (2013.01); *C12N 2501/237* (2013.01); *C12N 2501/39* (2013.01); *C12N 2501/415* (2013.01); *C12N 2501/602* (2013.01); *C12N 2501/603* (2013.01); *C12N 2501/604* (2013.01); *C12N 2501/606* (2013.01); *C12N 2506/1384* (2013.01); *C12N 2506/45* (2013.01); *C12N 2510/00* (2013.01); *C12N 2513/00* (2013.01); *C12N 2533/90* (2013.01)

(58) Field of Classification Search
CPC .... A61K 35/407; C12N 5/067; C12N 6/0696; C12N 2500/62; C12N 2501/119; C12N 2501/12; C12N 2501/155; C12N 2501/16
See application file for complete search history.

(56) References Cited

U.S. PATENT DOCUMENTS

| | | | |
|---|---|---|---|
| 2004/0018621 A1* | 1/2004 | Reid | ............... G01N 33/5005 435/370 |
| 2008/0031858 A1 | 2/2008 | Chan et al. | |
| 2010/0098739 A1 | 4/2010 | Katz et al. | |
| 2010/0112031 A1 | 5/2010 | Katz | |
| 2011/0020239 A1 | 1/2011 | Bulte et al. | |
| 2011/0294211 A1 | 12/2011 | D'Amour et al. | |
| 2012/0282228 A1 | 11/2012 | Bhasin | |
| 2013/0071931 A1 | 3/2013 | Ishikawa | |

FOREIGN PATENT DOCUMENTS

| | | |
|---|---|---|
| AU | 2007/244965 A1 | 11/2007 |
| EP | 1496110 | 1/2005 |
| EP | 2362899 A1 | 9/2011 |
| EP | 2554176 A1 | 2/2013 |
| JP | 2010/534065 A | 11/2010 |
| JP | 2012/509085 A | 4/2012 |
| WO | WO 2003/080821 | 10/2003 |
| WO | 2006/034873 A1 | 4/2006 |
| WO | 2007/089798 A2 | 8/2007 |
| WO | 2009/013254 A1 | 1/2009 |
| WO | 2009/092092 A1 | 7/2009 |
| WO | 2010/059775 A1 | 5/2010 |
| WO | 2010/108126 A2 | 9/2010 |

OTHER PUBLICATIONS

Banas et al., "Rapid hepatic fate specification of adipose-derived stem cells and their therapeutic potential for liver failure", 2009, Journal of Gastroenterology and Hepatology 24, p. 70-77.*
Yoon et al., "Enhanced Cartilage Formation via Three-Dimensional Cell Engineering of Human Adipose-Derived Stem Cells", Sep. 10, 2012, Tissue Engineering: Part A vol. 18(19-20), p. 1949-1956.*
Turner et al., "The performance of decellularized adipose tissue microcarriers as an inductive substrate for human adipose-derived stem cells", Mar. 26, 2012, Biomaterials 33, p. 4490-4499.*
Shen et al., "Implications of adipose-derived stromal cells in a 3D culture system for osteogenic differentiation: an in vitro and in vivo investigation", Jan. 2013, The Spine Journal 13(1), p. 32-43.*
Lee et al., "Possibility of Undifferentiated Human Thigh Adipose Stem Cells Differentiating into Functional Hepatocytes", Nov. 14, 2012, Archives of Plastic Surgery 39(6), p. 593-599.*

(Continued)

*Primary Examiner* — Scott Long
(74) *Attorney, Agent, or Firm* — Kyle A. Gurley; Bozicevic, Field & Francis LLP

(57) ABSTRACT

Methods are provided for producing a population of hepatocyte-like cells (iHeps) from a population of adipocyte-derived stem cells (ASCs). Aspects of the methods include placing a population of ASCs into a three dimensional culture (e.g., hanging drop suspension culture, high density culture, spinner flask culture, microcarrier culture, etc.), and contacting the cells with a first and second culture medium. Also provided are methods of treating an individual, which include producing a population of iHeps from a population of ASCs, and administering an effective number of iHeps into the individual. Kits for practicing the methods are also described herein.

12 Claims, 31 Drawing Sheets

Specification includes a Sequence Listing.

(56) References Cited

OTHER PUBLICATIONS

Behbahan et al., "New Approaches in the Differentiation of Human Embryonic Stem Cells and Induced Pluripotent Stem Cells toward Hepatocytes", 2011, Stem Cell Reviews and Reports, p. 748-759.*

Si-Tayeb et al., "Highly Efficient Generation of Human Hepatocyte-Like Cells from Induced Pluripotent Stem Cells", 2010, Hepatology vol. 51(1), p. 297-305.*

Hay et al., "Direct Differentiation of Human Embryonic Stem Cells to Hepatocyte-like Cells Exhibiting Functional Activities", 2007, Cloning and Stem Cells vol. 9(1), p. 51-62.*

Haraguchi et al., "Simple suspension culture system of human iPS cells maintaining their pluripotency for cardiac cell sheet engineering", J Tissue Eng Regen Med., Jun. 3, 2013, pp. 1363-1375, vol. 9, Issue 12, Wiley, Hoboken, NJ.

Behbahan et al., "New Approaches in the Differentiation of Human Embryonic Stem Cells and Induced Pluripotent Stem Cells toward Hepatocytes", Stem Cell Rev. and Rep., Sep. 2011, pp. 748-759, vol. 7, Issue 3, Springer, Berlin, Germany.

Firth et al., "Dynamic Three-Dimensional Culture Methods Enhance Mesenchymal Stem Cell Properties and Increase Therapeutic Potential", Tiss. Eng. C, Aug. 2010, pp. 735-749, vol. 16, Issue 4, Mary Ann Liebert, Inc., New Rochelle, NY.

Lock et al., "Expansion and Differentiation of Human Embryonic Stem Cells to Endoderm Progeny in a Microcarrier Stirred-Suspension Culture", Tiss. Eng. Part A, Aug. 2009, pp. 2051-2063, vol. 15, No. 8, Mary Ann Liebert, Inc., New Rochelle, NY.

Bartosh et al., "Aggregation of human mesenchymal stromal cells (MSCs) into 3D spheroids enhances their antiinflammatory properties", PNAS, Aug. 3, 2010, pp. 13724-13729, 107 (31), National Academy of Sciences, Washington, D.C.

Lotfi et al., "High yield generation of hepatocyte like cells from adipose derived stem cells", Sci. Res. Essays, Mar. 16, 2012, pp. 1141-1147, vol. 7 (10), Academic Journals, Abraka, Nigeria.

Duan et al., "Differentiation and Enrichment of Hepatocyte-Like Cells from Human Embryonic Stem Cells In Vitro and In Vivo", Stem Cells, Dec. 2007, pp. 3058-3068, vol. 25, Issue12, Wiley, Hoboken, NJ.

Agarwak et al., "Efficient Differentiation of Functional Hepatocytes from Human Embryonic Stem Cells", Stem Cells, May 2008, pp. 1117-1127, vol. 26, Issue 5, Wiley, Hoboken, NJ.

Battan et al., "Current Status of Human Adipose-Derived Stem Cells: Differentiation into Hepatocyte-Like Cells", Sci. World. J., Aug. 6, 2011, pp. 1568-1581, vol. 11, Hindawi Publishing Corporation, New York, NY.

Cai et al., "Directed differentiation of human embryonic stem cells into functional hepatic cells", Hepatol., May 2007, pp. 1229-1239, vol. 45, Issue 5, Wiley, Hoboken, NJ.

Cheng et al., "The influence of spheroid formation of human adipose-derived stem cells on chitosan films on stemness and differentiation capabilities", Biomater., Feb. 2012, pp. 1748-1758, vol. 33, Issue 6, Elsevier, New York City, NY.

Hamazaki et al., "Hepatic maturation in differentiating embryonic stem cells in vitro"', FEBS Let., May 18, 2001, pp. 15-19, vol. 497, Issue 1, Wiley, Hoboken, NJ.

Ma et al., "The Differentiation of Hepatocyte-Like Cells from Monkey Embryonic Stem Cells", Cloning Stem Cells, Dec. 2008, pp. 485-493, vol. 10, Issue 4, Mary Ann Liebert, Inc., New Rochelle, NY.

Touboul et al., "Generation of functional hepatocytes from human embryonic stem cells under chemically defined conditions that recapitulate liver development", Hepatol., May 2010, pp. 1754-1765, vol. 51, Issue 5, Wiley, Hoboken, NJ.

Snykers et al. "In Vitro Differentiation of Embryonic and Adult Stem Cells Into Hepatocytes: State of the Art" Stem Cells, Mar. 27, 2009, pp. 577-605,27, Wiley, Hoboken, NJ.

Amos et al., "Human Adipose-Derived Stromal Cells Accelerate Diabetic Wound Healing: Impact of Cell Formulation and Delivery", Tissue Engineering, May 2010, pp. 1595-1606, Part A, vol. 16, No. 5, Mary Ann Liebert, Inc., New Rochelle, NY.

Macisaac et al., "Long-term In-Vivo Tumorigenic Assessment of Human Culture-expanded Adipose Stromal/Stem Cells", Exp Cell Res., Feb. 15, 2012, pp. 416-423, vol. 318(4), Elsevier Inc, New York City, NY.

Kapur et al., "Human adipose stem cells maintain proliferative, synthetic and multipotential properties when suspension cultured as self-assembling spheroids", Biofabrication, Apr. 23, 2012, pp. 1-12, IOP Publishing Ltd, Bristol, United Kingdom.

Gutierrez et al., "A hanging drop culture method to study terminal erythroid differentiation", Exp Hematol. Oct. 2005, pp. 1083-1091, vol. 33(10), Elsevier Inc., New York City, NY.

Banerjee et al., "Application of hanging drop technique for stem cell differentiation and cytotoxicity studies", Cytotechnology, May 2006, pp. 1-5, vol. 51, Springer, Berlin, Germany.

Banas et al., "Adipose Tissue-Derived Mesenchymal Stem Cells as a Source of Human Hepatocytes", Hepatology, Jul. 2007, pp. 219-228, vol. 46, Issue 1, Wiley, Hoboken, NJ.

Green et al., "Generation of anterior foregut endoderm from human embryonic and induced pluripotent stem cells", Nat Biotechnol, Mar. 2011, pp. 267-272, vol. 29(3), Macmillan Publishers Limited, Basingstoke, United Kingdom.

So et al., "Wnt/b-catenin signaling cell-autonomously converts non-hepatic endodermal cells to a liver fate", Biology Open, Sep. 24, 2012, pp. 30-36, Biology Open Cambridge, United Kingdom.

Payne et al., "The role of activin/nodal and Wnt signaling in endoderm formation", Vitam Horm. 2011, pp. 207-216, vol. 85, Elsevier Inc., New York City, NY.

Hay et al., "Highly efficient differentiation of hESCs to functional hepatic endoderm requires ActivinA and Wnt3a Signaling", PNAS, Aug. 26, 2008, pp. 12301-12306, vol. 105, No. 34, National Academy of Sciences, Washington, D.C.

Cameron et al, "Improved Development of Human Embryonic Stem Cell-Derived Embryoid Bodies by Stirred Vessel Cultivation", Biotechnol Bioeng., Aug. 5, 2006, pp. 938-948, vol. 94, Issue 5, Wiley, Hoboken, NJ.

Lue et al, "Transdifferentiation of adipose-derived stem cells into hepatocytes: a new approach", Liver Int., Jul. 2010, pp. 913-922, vol. 30, Issue 6, Wiley, Hoboken, NJ.

Hasegawa et al, "The Reconstituted 'Humanized Liver' in TK-NOG Mice is Mature and Functional", Biochem Biophys Res Commun, Feb. 18, 2011, pp. 405-410, vol. 405, Issue 3, Elsevier Inc., New York City, NY.

Casadei et al., "Adipose Tissue Regeneration: A State of the Art", J Biomed Biotechnol. Jul. 16, 2012, pp. 1-12, vol. 2012, Hindawi Publishing Corporation, Cairo, Egypt.

Francesco et al, "Human CD34+/CD90+ ASCs Are Capable of Growing as Sphere Clusters, Producing High Levels ofVEGF and Forming Capillaries", PLoS One, Aug. 6, 2009 pp. 1-13, Vo14, Issue 8, PLoS ONE, San Francisco, CA.

Han et al, "An Endothelial Cell Niche Induces Hepatic Specification Through Dual Repression of Wnt and Notch Signaling", Stem Cells, Feb. 2011, pp. 217-228, vol. 29, Issue 2, Wiley, Hoboken, NJ.

Kelm et al, "Method for Generation of Homogeneous Multicellular Tumor Spheroids Applicable to a Wide Variety of Cell Types", Biotechnol Bioeng, Jul. 20, 2003, pp. 173-180, vol. 83, Issue 2, Wiley, Hoboken, NJ.

Pastrana et al, "Eyes Wide Open: A Critical Review of Sphere-Formation as an Assay for Stem Cells", Cell Stem Cell. May 6, 2011, pp. 486-498, 8(5), Elsevier Inc., New York City, NY.

Takahashi et al, "Biological and Clinical Availability of Adipose-Derived Stem Cells for Pelvic Dead Space Repair", Stem Cells Transl Med., Nov. 2012, pp. 803-810, 1(11), Wiley, Hoboken, NJ.

Ku et al, "Phenotypic correction of murine hemophilia A using an iPS cell-based therapy", Proc Natl Acad Sci USA., Jan. 20, 2009, pp. 808-813, vol. 106 (No. 3), National Academy of Sciences, Washington, DC.

Okura et al., "Properties of Hepatocyte-like Cell Clusters from Human Adipose Tissue-Derived Mesenchymal Stem", Tissue Engineering. Part C., Aug. 2010, pp. 761-770, 2010, vol. 16, No. 4, Mary Ann Liebert, Inc., New Rochelle, NY.

(56) References Cited

OTHER PUBLICATIONS

Seo et al., "Differentiation of human adipose stromal cells into hepatic lineage in vitro and in vivo", Biochemical and Biophysical Research Communications, Mar. 4, 2005, pp. 258-264, vol. 328. No. 1., Elsevier, New York City, NY.

Talens-Visconti et al., "Hepatogenic differentiation of human mesenchymal stem cells from adipose tissue in comparison with bone marrow mesenchymal stem cells", World Journal of Gastroenterology, Sep. 28, 2006, pp. 5834-2845, vol. 12, No. 36, Baishideng Publishing Group, Pleasanton, CA.

Ku et al., "Rapid and high-efficiency generation of mature functional hepatocyte-like cells from adipose-derived stem cells by a three-step protocol", Stem Cell Research & Therapy, Oct. 5, 2015, pp. 1-10, vol. 6. No. 1, Biomed Central LTD, London, United Kingdom.

Banas et al., "Rapid hepatic fate specification of adipose-derived stem cells and their therapeutic potential for liver failure", J Gastroenterol Hepatol., Jan. 2009, pp. 70-77, vol. 24, Issue 1, Wiley, Hoboken, NJ.

\* cited by examiner

FIGURE 11

Selected Genes: 1129 genes with increased expression in hepatocytes (vs ASC)

|  | Increased | Decreased | NS |
|---|---|---|---|
| Chi-Hep vs ASC | 494 (44%) | 2 (0%) | 633 (56%) |
| Sci-Hep vs ASC | 565 (50%) | 6 (1%) | 558 (49%) |
| iPS-Hep vs ASC | 591 (52%) | 22 (2%) | 516 (46%) |

Selected Genes: 1437 genes with decreased expression in hepatocytes (vs ASC)

|  | Increased | Decreased | NS |
|---|---|---|---|
| Chi-Hep vs ASC | 49 (3%) | 341 (24%) | 1047 (73%) |
| Sci-Hep vs ASC | 81 (6%) | 449 (31%) | 907 (63%) |
| iPS-Hep vs ASC | 93 (6%) | 781 (54%) | 563 (39%) |

Selected Genes: 16446 genes with insignificant changes in hepatocytes (vs ASC)

|  | Increased | Decreased | NS |
|---|---|---|---|
| Chi-Hep vs ASC | 256 (2%) | 345 (2%) | 15845 (96%) |
| Sci-Hep vs ASC | 764 (5%) | 507 (3%) | 15175 (92%) |
| iPS-Hep vs ASC | 1718 (10%) | 1251 (8%) | 13477 (82%) |

FIGURE 12

|  | *Foxa2* | *Albumin* | *CD105* |
|---|---|---|---|
| P-value | | | |
| Day 3 | 2.81E-06 | 0.00307 | 0.012584 |
| Day 6 | 0.000182 | 0.000224 | 0.000616 |
| Day 12 | 0.000683 | 9.35 E-05 | 0.001107 |
| Fold-Change | | | |
| Day 3 | 9.4 | 11.0 | -3.3 |
| Day 6 | 19.7 | 16.7 | -12.3 |
| Day 12 | 25.3 | 50.8 | -34.8 |

SEQUENCE LISTING

<160> NUMBER OF SEQ ID NOS: 19

<210> SEQ ID NO 1
<211> LENGTH: 426
<212> TYPE: PRT
<213> ORGANISM: Homo sapiens

<400> SEQUENCE: 1

```
Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
        355                 360                 365
```

His Ser Thr Val Ile Asn His Tyr Arg Met Arg Gly His Ser Pro Phe
370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
            405                 410                 415

Asn Met Ile Val Glu Glu Cys Gly Cys Ser
            420                 425

<210> SEQ ID NO 2
<211> LENGTH: 155
<212> TYPE: PRT
<213> ORGANISM: Homo sapiens

<400> SEQUENCE: 2

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155

<210> SEQ ID NO 3
<211> LENGTH: 288
<212> TYPE: PRT
<213> ORGANISM: Homo sapiens

<400> SEQUENCE: 3

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
                20                  25                  30

Pro Gly Ala Ala Ala Trp Glu Ala Ala Leu Pro Arg Arg Arg Pro Arg
            35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

```
Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
        130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 4
<211> LENGTH: 239
<212> TYPE: PRT
<213> ORGANISM: Homo sapiens

<400> SEQUENCE: 4

Met Gly Leu Ile Trp Leu Leu Leu Leu Ser Leu Leu Glu Pro Gly Trp
1               5                   10                  15

Pro Ala Ala Gly Pro Gly Ala Arg Leu Arg Arg Asp Ala Gly Gly Arg
            20                  25                  30

Gly Gly Val Tyr Glu His Leu Gly Gly Ala Pro Arg Arg Arg Lys Leu
        35                  40                  45

Tyr Cys Ala Thr Lys Tyr His Leu Gln Leu His Pro Ser Gly Arg Val
50                  55                  60

Asn Gly Ser Leu Glu Asn Ser Ala Tyr Ser Ile Leu Glu Ile Thr Ala
65                  70                  75                  80

Val Glu Val Gly Ile Val Ala Ile Arg Gly Leu Phe Ser Gly Arg Tyr
                85                  90                  95

Leu Ala Met Asn Lys Arg Gly Arg Leu Tyr Ala Ser Glu His Tyr Ser
            100                 105                 110

Ala Glu Cys Glu Phe Val Glu Arg Ile His Glu Leu Gly Tyr Asn Thr
        115                 120                 125

Tyr Ala Ser Arg Leu Tyr Arg Thr Val Ser Ser Thr Pro Gly Ala Arg
    130                 135                 140

Arg Gln Pro Ser Ala Glu Arg Leu Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu Asp His Arg Asp His Glu Met Val Arg
            180                 185                 190

Gln Leu Gln Ser Gly Leu Pro Arg Pro Pro Gly Lys Gly Val Gln Pro
        195                 200                 205
```

-continued

Arg Arg Arg Arg Gln Lys Gln Ser Pro Asp Asn Leu Glu Pro Ser His
            210                 215                 220

Val Gln Ala Ser Arg Leu Gly Ser Gln Leu Glu Ala Ser Ala His
225                 230                 235

<210> SEQ ID NO 5
<211> LENGTH: 206
<212> TYPE: PRT
<213> ORGANISM: Homo sapiens

<400> SEQUENCE: 5

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Ala Ala Ala Pro
            20                  25                  30

Thr Ala Pro Asn Gly Thr Leu Glu Ala Glu Leu Glu Arg Arg Trp Glu
            35                  40                  45

Ser Leu Val Ala Leu Ser Leu Ala Arg Leu Pro Val Ala Ala Gln Pro
50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
            115                 120                 125

Phe Gly Val Ala Ser Arg Phe Phe Val Ala Met Ser Ser Lys Gly Lys
130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
            195                 200                 205

<210> SEQ ID NO 6
<211> LENGTH: 268
<212> TYPE: PRT
<213> ORGANISM: Homo sapiens

<400> SEQUENCE: 6

Met Ser Leu Ser Phe Leu Leu Leu Phe Phe Ser His Leu Ile Leu
1               5                   10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Ser Arg Gln
            35                  40                  45

Ser Ser Ser Ser Ala Met Ser Ser Ser Ala Ser Ser Ser Pro Ala
50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

```
Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
            115                 120                 125

Gly Ile Val Gly Ile Arg Gly Val Phe Ser Asn Lys Phe Leu Ala Met
        130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Lys Pro Pro
225                 230                 235                 240

Ser Pro Ile Lys Pro Lys Ile Pro Leu Ser Ala Pro Arg Lys Asn Thr
                245                 250                 255

Asn Ser Val Lys Tyr Arg Leu Lys Phe Arg Phe Gly
                260                 265

<210> SEQ ID NO 7
<211> LENGTH: 208
<212> TYPE: PRT
<213> ORGANISM: Homo sapiens

<400> SEQUENCE: 7

Met Ala Leu Gly Gln Lys Leu Phe Ile Thr Met Ser Arg Gly Ala Gly
1               5                   10                  15

Arg Leu Gln Gly Thr Leu Trp Ala Leu Val Phe Leu Gly Ile Leu Val
            20                  25                  30

Gly Met Val Val Pro Ser Pro Ala Gly Thr Arg Ala Asn Asn Thr Leu
        35                  40                  45

Leu Asp Ser Arg Gly Trp Gly Thr Leu Leu Ser Arg Ser Arg Ala Gly
    50                  55                  60

Leu Ala Gly Glu Ile Ala Gly Val Asn Trp Glu Ser Gly Tyr Leu Val
65                  70                  75                  80

Gly Ile Lys Arg Gln Arg Arg Leu Tyr Cys Asn Val Gly Ile Gly Phe
                85                  90                  95

His Leu Gln Val Leu Pro Asp Gly Arg Ile Ser Gly Thr His Glu Glu
            100                 105                 110

Asn Pro Tyr Ser Leu Leu Glu Ile Ser Thr Val Glu Arg Gly Val Val
        115                 120                 125

Ser Leu Phe Gly Val Arg Ser Ala Leu Phe Val Ala Met Asn Ser Lys
    130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
            180                 185                 190

Ser Lys Val Ser Pro Ile Met Thr Val Thr His Phe Leu Pro Arg Ile
        195                 200                 205
```

<210> SEQ ID NO 8
<211> LENGTH: 194
<212> TYPE: PRT
<213> ORGANISM: Homo sapiens

<400> SEQUENCE: 8

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
            20                  25                  30

Asn Asp Met Thr Pro Glu Gln Met Ala Thr Asn Val Asn Cys Ser Ser
        35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr
```

<210> SEQ ID NO 9
<211> LENGTH: 233
<212> TYPE: PRT
<213> ORGANISM: Homo sapiens

<400> SEQUENCE: 9

```
Met Gly Ser Pro Arg Ser Ala Leu Ser Cys Leu Leu Leu His Leu Leu
1               5                   10                  15

Val Leu Cys Leu Gln Ala Gln Glu Gly Pro Gly Arg Gly Pro Ala Leu
            20                  25                  30

Gly Arg Glu Leu Ala Ser Leu Phe Arg Ala Gly Arg Glu Pro Gln Gly
        35                  40                  45

Val Ser Gln Gln His Val Arg Glu Gln Ser Leu Val Thr Asp Gln Leu
    50                  55                  60

Ser Arg Arg Leu Ile Arg Thr Tyr Gln Leu Tyr Ser Arg Thr Ser Gly
65                  70                  75                  80

Lys His Val Gln Val Leu Ala Asn Lys Arg Ile Asn Ala Met Ala Glu
                85                  90                  95

Asp Gly Asp Pro Phe Ala Lys Leu Ile Val Glu Thr Asp Thr Phe Gly
            100                 105                 110

Ser Arg Val Arg Val Arg Gly Ala Glu Thr Gly Leu Tyr Ile Cys Met
        115                 120                 125

Asn Lys Lys Gly Lys Leu Ile Ala Lys Ser Asn Gly Lys Gly Lys Asp
    130                 135                 140
```

Cys Val Phe Thr Glu Ile Val Leu Glu Asn Asn Tyr Thr Ala Leu Gln
145                 150                 155                 160

Asn Ala Lys Tyr Glu Gly Trp Tyr Met Ala Phe Thr Arg Lys Gly Arg
                165                 170                 175

Pro Arg Lys Gly Ser Lys Thr Arg Gln His Gln Arg Glu Val His Phe
            180                 185                 190

Met Lys Arg Leu Pro Arg Gly His His Thr Thr Glu Gln Ser Leu Arg
        195                 200                 205

Phe Glu Phe Leu Asn Tyr Pro Pro Phe Thr Arg Ser Leu Arg Gly Ser
210                 215                 220

Gln Arg Thr Trp Ala Pro Glu Pro Arg
225                 230

<210> SEQ ID NO 10
<211> LENGTH: 208
<212> TYPE: PRT
<213> ORGANISM: Homo sapiens

<400> SEQUENCE: 10

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205

<210> SEQ ID NO 11
<211> LENGTH: 208
<212> TYPE: PRT
<213> ORGANISM: Homo sapiens

<400> SEQUENCE: 11

Met Trp Lys Trp Ile Leu Thr His Cys Ala Ser Ala Phe Pro His Leu
1               5                   10                  15

Pro Gly Cys Cys Cys Cys Cys Phe Leu Leu Leu Phe Leu Val Ser Ser
            20                  25                  30

Val Pro Val Thr Cys Gln Ala Leu Gly Gln Asp Met Val Ser Pro Glu
    35                  40                  45

Ala Thr Asn Ser Ser Ser Ser Phe Ser Ser Pro Ser Ser Ala Gly
 50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                 85                  90                  95

Lys Val Ser Gly Thr Lys Lys Glu Asn Cys Pro Tyr Ser Ile Leu Glu
                100                 105                 110

Ile Thr Ser Val Glu Ile Gly Val Val Ala Val Lys Ala Ile Asn Ser
                115                 120                 125

Asn Tyr Tyr Leu Ala Met Asn Lys Lys Gly Lys Leu Tyr Gly Ser Lys
130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
                180                 185                 190

Arg Arg Lys Asn Thr Ser Ala His Phe Leu Pro Met Val Val His Ser
195                 200                 205

<210> SEQ ID NO 12
<211> LENGTH: 207
<212> TYPE: PRT
<213> ORGANISM: Homo sapiens

<400> SEQUENCE: 12

Met Ala Glu Val Gly Gly Val Phe Ala Ser Leu Asp Trp Asp Leu His
 1               5                  10                  15

Gly Phe Ser Ser Ser Leu Gly Asn Val Pro Leu Ala Asp Ser Pro Gly
                 20                  25                  30

Phe Leu Asn Glu Arg Leu Gly Gln Ile Glu Gly Lys Leu Gln Arg Gly
                 35                  40                  45

Ser Pro Thr Asp Phe Ala His Leu Lys Gly Ile Leu Arg Arg Arg Gln
 50                  55                  60

Leu Tyr Cys Arg Thr Gly Phe His Leu Glu Ile Phe Pro Asn Gly Thr
 65                  70                  75                  80

Val His Gly Thr Arg His Asp His Ser Arg Phe Gly Ile Leu Glu Phe
                 85                  90                  95

Ile Ser Leu Ala Val Gly Leu Ile Ser Ile Arg Gly Val Asp Ser Gly
                100                 105                 110

Leu Tyr Leu Gly Met Asn Glu Arg Gly Glu Leu Tyr Gly Ser Lys Lys
                115                 120                 125

Leu Thr Arg Glu Cys Val Phe Arg Glu Gln Phe Glu Glu Asn Trp Tyr
130                 135                 140

Asn Thr Tyr Ala Ser Thr Leu Tyr Lys His Ser Asp Ser Glu Arg Gln
145                 150                 155                 160

Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
                180                 185                 190

Pro Ser Lys Leu Pro Ser Met Ser Arg Asp Leu Phe His Tyr Arg
                195                 200                 205

<210> SEQ ID NO 13
<211> LENGTH: 216
<212> TYPE: PRT
<213> ORGANISM: Homo sapiens

<400> SEQUENCE: 13

```
Met Gly Ala Ala Arg Leu Leu Pro Asn Leu Thr Leu Cys Leu Gln Leu
1               5                   10                  15

Leu Ile Leu Cys Cys Gln Thr Gln Gly Glu Asn His Pro Ser Pro Asn
            20                  25                  30

Phe Asn Gln Tyr Val Arg Asp Gln Gly Ala Met Thr Asp Gln Leu Ser
        35                  40                  45

Arg Arg Gln Ile Arg Glu Tyr Gln Leu Tyr Ser Arg Thr Ser Gly Lys
50                  55                  60

His Val Gln Val Thr Gly Arg Arg Ile Ser Ala Thr Ala Glu Asp Gly
65                  70                  75                  80

Asn Lys Phe Ala Lys Leu Ile Val Glu Thr Asp Thr Phe Gly Ser Arg
                85                  90                  95

Val Arg Ile Lys Gly Ala Glu Ser Glu Lys Tyr Ile Cys Met Asn Lys
            100                 105                 110

Arg Gly Lys Leu Ile Gly Lys Pro Ser Gly Lys Ser Lys Asp Cys Val
        115                 120                 125

Phe Thr Glu Ile Val Leu Glu Asn Asn Tyr Thr Ala Phe Gln Asn Ala
130                 135                 140

Arg His Glu Gly Trp Phe Met Ala Phe Thr Arg Gln Gly Arg Pro Arg
145                 150                 155                 160

Gln Ala Ser Arg Ser Arg Gln Asn Gln Arg Glu Ala His Phe Ile Lys
                165                 170                 175

Arg Leu Tyr Gln Gly Gln Leu Pro Phe Pro Asn His Ala Glu Lys Gln
            180                 185                 190

Lys Gln Phe Glu Phe Val Gly Ser Ala Pro Thr Arg Arg Thr Lys Arg
        195                 200                 205

Thr Arg Arg Pro Gln Pro Leu Thr
210                 215
```

<210> SEQ ID NO 14
<211> LENGTH: 207
<212> TYPE: PRT
<213> ORGANISM: Homo sapiens

<400> SEQUENCE: 14

```
Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110
```

```
Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205

<210> SEQ ID NO 15
<211> LENGTH: 211
<212> TYPE: PRT
<213> ORGANISM: Homo sapiens

<400> SEQUENCE: 15

Met Ala Pro Leu Ala Glu Val Gly Gly Phe Leu Gly Gly Leu Glu Gly
1               5                   10                  15

Leu Gly Gln Gln Val Gly Ser His Phe Leu Pro Pro Ala Gly Glu
            20                  25                  30

Arg Pro Pro Leu Leu Gly Glu Arg Ser Ala Ala Glu Arg Ser Ala
        35                  40                  45

Arg Gly Gly Pro Gly Ala Ala Gln Leu Ala His Leu His Gly Ile Leu
    50                  55                  60

Arg Arg Arg Gln Leu Tyr Cys Arg Thr Gly Phe His Leu Gln Ile Leu
65                  70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
            100                 105                 110

Val Asp Ser Gly Leu Tyr Leu Gly Met Asn Asp Lys Gly Glu Leu Tyr
        115                 120                 125

Gly Ser Glu Lys Leu Thr Ser Glu Cys Ile Phe Arg Glu Gln Phe Glu
    130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Met Tyr Thr
        210

<210> SEQ ID NO 16
<211> LENGTH: 170
<212> TYPE: PRT
<213> ORGANISM: Homo sapiens
```

```
<400> SEQUENCE: 16

Met Arg Arg Arg Leu Trp Leu Gly Leu Ala Trp Leu Leu Leu Ala Arg
1               5                   10                  15

Ala Pro Asp Ala Ala Gly Thr Pro Ser Ala Ser Arg Gly Pro Arg Ser
            20                  25                  30

Tyr Pro His Leu Glu Gly Asp Val Arg Trp Arg Arg Leu Phe Ser Ser
            35                  40                  45

Thr His Phe Phe Leu Arg Val Asp Pro Gly Gly Arg Val Gln Gly Thr
        50                  55                  60

Arg Trp Arg His Gly Gln Asp Ser Ile Leu Glu Ile Arg Ser Val His
65                  70                  75                  80

Val Gly Val Val Val Ile Lys Ala Val Ser Ser Gly Phe Tyr Val Ala
                85                  90                  95

Met Asn Arg Arg Gly Arg Leu Tyr Gly Ser Arg Leu Tyr Thr Val Asp
            100                 105                 110

Cys Arg Phe Arg Glu Arg Ile Glu Glu Asn Gly His Asn Thr Tyr Ala
        115                 120                 125

Ser Gln Arg Trp Arg Arg Gly Gln Pro Met Phe Leu Ala Leu Asp
        130                 135                 140

Arg Arg Gly Gly Pro Arg Pro Gly Gly Arg Thr Arg Tyr His Leu
145                 150                 155                 160

Ser Ala His Phe Leu Pro Val Leu Val Ser
                165                 170

<210> SEQ ID NO 17
<211> LENGTH: 352
<212> TYPE: PRT
<213> ORGANISM: Homo sapiens

<400> SEQUENCE: 17

Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
    50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
    130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190
```

-continued

Gln Ala Ile Ala Ser His Met His Leu Lys Cys Lys Cys His Gly Leu
            195                 200                 205

Ser Gly Ser Cys Glu Val Lys Thr Cys Trp Trp Ser Gln Pro Asp Phe
210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
            245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
            275                 280                 285

Ser Phe Gly Thr Arg Asp Arg Thr Cys Asn Val Ser Ser His Gly Ile
            290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
            325                 330                 335

Val Ser Cys Gln Glu Cys Thr Arg Val Tyr Asp Val His Thr Cys Lys
            340                 345                 350

<210> SEQ ID NO 18
<211> LENGTH: 728
<212> TYPE: PRT
<213> ORGANISM: Homo sapiens

<400> SEQUENCE: 18

Met Trp Val Thr Lys Leu Leu Pro Ala Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

```
His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
            245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
        290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
        370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
        450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
            485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
            515                 520                 525

Val Leu Thr Ala Arg Gln Cys Phe Pro Ser Arg Asp Leu Lys Asp Tyr
        530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
610                 615                 620
```

```
Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
            645                 650                 655

Ile Cys Ala Gly Ala Glu Lys Ile Gly Ser Gly Pro Cys Glu Gly Asp
        660                 665                 670

Tyr Gly Gly Pro Leu Val Cys Glu Gln His Lys Met Arg Met Val Leu
    675                 680                 685

Gly Val Ile Val Pro Gly Arg Gly Cys Ala Ile Pro Asn Arg Pro Gly
        690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 19
<211> LENGTH: 252
<212> TYPE: PRT
<213> ORGANISM: Homo sapiens

<400> SEQUENCE: 19

Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
            85                  90                  95

Gln Thr Leu Asn Ala Thr Leu Gly Cys Val Leu His Arg Leu Ala Asp
        100                 105                 110

Leu Glu Gln Arg Leu Pro Lys Ala Gln Asp Leu Glu Arg Ser Gly Leu
    115                 120                 125

Asn Ile Glu Asp Leu Glu Lys Leu Gln Met Ala Arg Pro Asn Ile Leu
130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
            165                 170                 175

Thr Pro Thr Pro Ala Ser Asp Ala Phe Gln Arg Lys Leu Glu Gly Cys
    180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
            245                 250
```

METHODS AND COMPOSITIONS FOR PRODUCING HEPATOCYTE-LIKE CELLS

CROSS REFERENCE

This application claims benefit and is a Continuation of application Ser. No. 14/917,558 filed Mar. 8, 2016, which is a national stage entry of PCT Application No. PCT/US2014/056049, filed Sep. 17, 2014, which claims benefit of U.S. Provisional Patent Application No. 61/880,056, filed Sep. 19, 2013, which applications are incorporated herein by reference in their entirety.

GOVERNMENT RIGHTS

This invention was made with Government support under contract DK090992 awarded by the National Institutes of Health. The Government has certain rights in the invention.

BACKGROUND

A major goal for regenerative medicine is to facilitate human tissue replacement through transplantation of stem cells that can be harvested from readily accessible tissues. For example, orthotopic liver transplantation is the only effective treatment for end-stage liver disease or severe liver injury, but its utility is severely limited by the lack of donor liver tissue and by the requirement for lifelong immunosuppression.

A large number of adipocyte-derived stem cells (ASCs) can be easily obtained using a commonly performed procedure, liposuction. Additionally, methods for inducing ASC differentiation into hepatocyte-like cells (iHeps) have been developed. Liver regeneration via transplantation of iHeps (e.g., autologous iHeps) is a highly attractive possibility for regenerative medicine. By this method, ASC obtained by liposuction are induced to differentiate into iHeps in vitro, and then iHeps are transplanted into the donor's liver. The abundance and accessibility of adipose tissue ensures that there is a source of readily available ASCs. Moreover, liver regeneration using autologous iHeps would not require immunosuppression.

However, since a patient can die rapidly after acute liver failure (e.g., caused by acetaminophen toxicity), the prolonged culture period associated with the currently known method to produce iHeps from ASCs severely limits the clinical utility for producing iHeps. Furthermore, the known method to produce iHeps from ASCs is also characterized by low efficiency and low yield.

The production of hepatocyte-like cells from adipocyte-derived stem cells for use in therapy and/or research will benefit from reduced cost, reduced culture time, increased efficiency, and increased yield.

PUBLICATIONS

Amos et al., Tissue Eng Part A. 2010 May; 16(5):1595-606; MacIsaac et al., Exp Cell Res. 2012 Feb. 15; 318(4): 416-423; Kapur et al, Biofabrication. 2012 Jun.; 4(2): 025004; Gutierrez et al., Exp Hematol. 2005 October; 33(10):1083-91; Banerjee et al, Cytotechnology. 2006 May; 51(1):1-5. -2006; Banas et al., Hepatology. 2007 July; 46(1):219-28; Banas et al., J Gastroenterol Hepatol. 2009 Jan.; 24(1):70-7; Green et al., 2011. Nat Biotechnol 29:267-272; So et al., Biol Open. 2013 Jan. 15; 2(1):30-6; Payne et al., Vitam Horm. 2011; 85:207-16; Hay et al., Proc Natl Acad Sci USA. 2008 Aug. 26; 105(34):12301-6; Lue et al, Liver Int. 2010 Jul.; 30(6):913-22; Hasegawa et al, Biochem Biophys Res Commun. 2011 Feb. 18; 405 (3):405-10; Haraguchi et al, J Tissue Eng Regen Med. 2013 Jun. 3; Cameron et al, Biotechnol Bioeng. 2006 Aug. 5; 94(5):938-48; WO2007089798; US20100098739; and US20100112031.

SUMMARY

Methods are provided for producing a population of hepatocyte-like cells (iHeps) from a population of adipocyte-derived stem cells (ASCs). Aspects of the methods include placing a population of ASCs into a three dimensional culture (e.g., hanging drop suspension culture, high density culture, spinner flask culture, microcarrier culture, etc.) and contacting the cells with a first and second culture medium. Also provided are methods of treating an individual, which include producing a population of iHeps from a population of ASCs, and administering an effective number of iHeps into the individual.

The presence of iHeps may be confirmed by various methods, including for example, contacting the induced cell population with an antibody specific for a hepatocyte marker protein, and determining the percentage of cells positive for expression. In some embodiments, 15% or more of cells of the induced cell population are hepatocyte-like cells. In some cases, 37% or more of the cells of the induced cell population are hepatocyte-like cells. In some embodiments, the elapsed time to generate iHeps from ASCs is less than 13 days (e.g., less than 10 days). The high efficiency of iHep production and the short time frame over which iHeps can be produced by the subject methods facilitate treatment methods because liver damage (e.g., liver failure, e.g., due to acetaminophen toxicity) can rapidly cause death (e.g., in 2 weeks or less). Kits for practicing the methods of the disclosure are also provided.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A) The two different methods for inducing the differentiation of ASC into iHeps are shown. The top panel shows the method for chemically differentiating ASC into Chi-Heps. The cells isolated from lipo-aspirates are cultured for 3-15 days ASC cells. These cells are then differentiated from mesoderm into endodermal cells over a 3-day period (stage 1), and then further differentiated into Chi-Heps (stage 2) using defined media containing growth factors. The bottom panel shows one embodiment of a subject method for producing SCi-Heps. (FIG. 1B) Bright field images (100×) showing the change in the morphology of the spindle-shaped ASC as they differentiate into Chi-Heps (via chemical differentiation) or SCi-Heps using a subject method for producing SCi-Heps. Relative to Chi-Heps, SCi-Heps have a greater cellular density and colony-like morphology that more closely resembles hepatocytes. (FIG. 1C) The percentage of ASC, Chi-Heps, SCi-Heps and iPS-Heps expressing the CK8/18 marker found on mature hepatocytes. Unstained ASC were used to characterize the background level of staining (control), and 100% of human hepatocytes express this marker. (FIG. 1D) Immunofluorescence staining images (at 100×) of control ASC, Chi-Heps, SCi-Heps or hepatocytes for human CK8/18 expression, LDL uptake or PAS staining. Chi-Heps and SCi-Heps, but not ASC, can endocytose LDL and can synthesize glycogen (PAS stain). (FIG. 1E) The amount of human albumin or urea secreted into the supernatant by Chi-Heps, SCi-Heps and ASC cultured for the indicated time period. SCi-Heps produced albumin and urea well before Chi-Heps produced detectable amounts of these analytes, while ASC did not produce albumin or urea. In panels C and E, each bar represents the average (+SEM) of 4 biologically independent samples analyzed.

(FIG. 2A) iHeps have increased levels of hepatocyte-specific mRNAs and decreased levels of adipocyte-specific mRNAs. RT-PCR analysis was used to measure the level of hepatocyte-specific (FoxA2, AFP, ALB, AAT, TDO2) or adipocyte-specific (CD37) mRNA expression in Chi-Heps, SCi-Heps, iPS-Heps or ASCs. For each gene, the mRNA levels in Chi-Heps (after 15 days of differentiation), SCi-Heps (after 9 days of differentiation) and iPS-Heps (after 30 days of differentiation) are normalized relative to that in ASCs. (FIG. 2B) RT-PCR analysis of the gene expression in ASCs, and in SCi-Heps after 3, 6 and 12 days of induced differentiation. The level of CD105 mRNA expression (which is an ASC marker) was decreased by 35-fold (p=0.001); while the level of hepatocyte (FoxA2 and ALB) mRNA expression was increased by 25- and 51-fold, respectively (p=0.0007 and 9×10$^{-5}$, respectively), in SCi-Heps after 12 days of hepatocyte differentiation. The mRNA levels in SCi-Heps were normalized relative to that in ASCs. Each data point in panels A-B represents the average±SEM for 3 independent determinations. As shown in FIG. 11, there were significant changes in the level of expression of each gene in SCi-Heps after 3, 6 and 12 days of differentiation. (FIG. 2C) An illustration of the spatial relationship between the gene expression profiles obtained from ASCs, Chi-Heps, SCi-Heps, iPS-Heps and hepatocytes. Microarray-based global gene expression data was analyzed as described in the methods section. The lengths of each connecting edge (and the number shown) indicate the distance between the expression profiles for the cell types at each of the corresponding vertices. This distance is determined by summing the squares of the differences in the level of expression for each gene on the array for the two cell types at the vertices of each line. This diagram indicates that the gene expression pattern in Chi- and SCi-Heps is closer to that of hepatocytes than is that of iPS-Heps. Also, the deviation of the iPS-Heps pattern from the ASC-hepatocyte axis is larger than that of iHeps, which indicates that iPS-Heps have a larger number of gene expression changes that are external to both ASCs and hepatocytes than are found in Chi- or SCi-Heps.

(FIG. 3A) An ultrasound generated image (in transverse view) of SCi-Heps being injected through a 30G needle directly into the right lobe of the liver of a TK-NOG mouse. (FIG. 3B) Chimeric mice produced human albumin after SCi-Hep transplantation. The amount of human albumin in plasma was serially measured over an 8-week period after transplantation of SCi-Heps into 4 ganciclovir-conditioned mice. Each dashed line shows the amount of human albumin measured in a chimeric mouse at the indicated time. In all 4 chimeric mice, human serum albumin was detectable 4 weeks after transplantation, and the amount increased with time after transplantation. In contrast, albumin was not produced by any of the 4 mice that were recipients of control, undifferentiated ASCs (red triangles and solid line). (FIG. 3C) Immunofluorescent staining of liver sections (at 100× magnification) obtained from TK-NOG mice 4 weeks after implantation of SCi-Heps, (a-c) or undifferentiated ASCs (d-f). The liver sections were stained with human specific anti-albumin (a, d), anti-CK8/18 (b, e), or anti ASGR1 antibodies, and counter-strained with DAPI to show the cell nuclei. (FIG. 3D) Immunofluorescent staining of liver sections (200× magnification) obtained from TK-NOG mice 4 weeks after transplantation with SCi-Heps or undifferentiated ASCs. The liver sections were stained with anti-CK8/18, anti-Ki67 or anti-ZO-1 antibodies; and were then counter-strained with DAPI to show the cell nuclei.

(FIG. 4A) As early as three weeks after 5×10$^4$ iPS-Heps were implanted under the kidney capsule of NOG mice, palpable tumors were formed in the area of implantation. In contrast, no tumors were detected 2-months after the same number of Chi- or SCi-Heps were implanted (top row). The tumors were visible in tissue sections obtained from the area of iPS-Hep implantation, while only normal tissue was present in the area of Chi-Hep implantation (middle row). The magnification of images in the top and middle rows are 10×. The images in the bottom rows were obtained from the boxed regions of the corresponding image and are shown at 200× magnification. (FIG. 4B) Tumor formation after iPS-Heps implantation. Top row: Images of the tumors formed 3 weeks after iPS-Hep cells were implanted under the kidney capsule. The 300× and 100× images were obtained from the indicated region (dashed box) of the corresponding 40× and 100× images. Bottom row: Two months after the iPS-iHep cells were implanted, the tumors contained cells from all three germ cell layers. These images are at 200× magnification. The scale bars shown are 50 µm.

(FIG. 8C) Chi-Heps (after 15 days) and iPS-Heps (after 30 days of differentiation), but not ASCs, can mediate a CYP3A4-dependent drug biotransformation reaction. (FIG. 8D) iPS-Heps have increased levels of hepatocyte-specific and decreased levels of adipocyte-specific mRNAs. RT-PCR analysis was used to measure the level of hepatocyte-specific (FoxA2, AFP, ALB, AAT, A1AT, TDO2) or adipocyte-specific (CD37, CD29) mRNA expression in s, iPS-Heps or ASCs. For each gene, the mRNA levels in in Chi-Heps (after 15 days of differentiation) and iPS-Heps (after 30 days of differentiation) are normalized relative to that of the corresponding mRNA level in ASCs. Each bar or data point in panels A-D represents the average ($\pm$SEM) of 4 biologically independent samples that were analyzed.

FIG. 11 presents a table depicting the numbers of differentially expressed genes in hepatocytes, Chi-Heps, SCi-Heps, and iPS-heps relative to ASCs. From analysis of microarray data, the indicated number of genes whose expression was significantly increased, decreased or unchanged in hepatocytes relative to ASCs were selected. (A gene's expression was considered as altered in hepatocytes if the absolute value of the fold change was >5 and the adjusted p value was <0.01.) Each of the 3 panels indicates the number (and percentage) of the selected genes whose expression was increased, decreased or not significantly changed (NS) when the expression profiles in Chi-Heps, SCi-Heps or iPS-Heps (relative to ASCs). For each of these comparisons, the expression of a gene was considered altered in iHeps if the absolute value of the fold change was >2 and the adjusted p value was <0.01. It is noteworthy that 18% of the genes whose expression was not altered in hepatocytes had an altered level of expression in iPS-Heps.

FIG. 12 presents a table depicting changes in the level of expression of genes (Foxa2, Albumin) expressed in hepatocytes and in adipocyte-specific (CD105) mRNAs during induced SCi-Hep differentiation. RT-PCR was used to measure the level of expression of 3 genes (Foxa2, Albumin and CD105) in ASC, and in SCi-Heps after 3, 6 and 12 days of induced differentiation. The measured average expression levels for each gene in SCi-Heps on the indicated day (relative to its level of expression in ASC) and the corresponding p-values for the expression differences are shown. Each value is the average fold-change for 3 independent measurements; a positive value indicates that its expression was increased in SCi-Heps relative to ASC, while a negative value indicates that it was decreased. A one-sample t-test was applied using the log-transformed expression level to assess the statistical significance (P-value) of the measured expression differences.

(FIG. 13A) The morphology of ASC cellular aggregates formed after spinner flask culture of ASCs for 24 hours. The morphology of the aggregates is very similar to that of the 'spheres' formed after culturing ASCs by the hanging drop method. The increased cell density (hence the term "high density culture") in the spinner flask culture is readily apparent when comparing panel (FIG. 13A) to panel (FIG. 13B). (FIG. 13B) 'spheres' formed after culturing ASCs by the hanging drop method for 48 hours.

DETAILED DESCRIPTION OF THE EMBODIMENTS

Figure 1A:
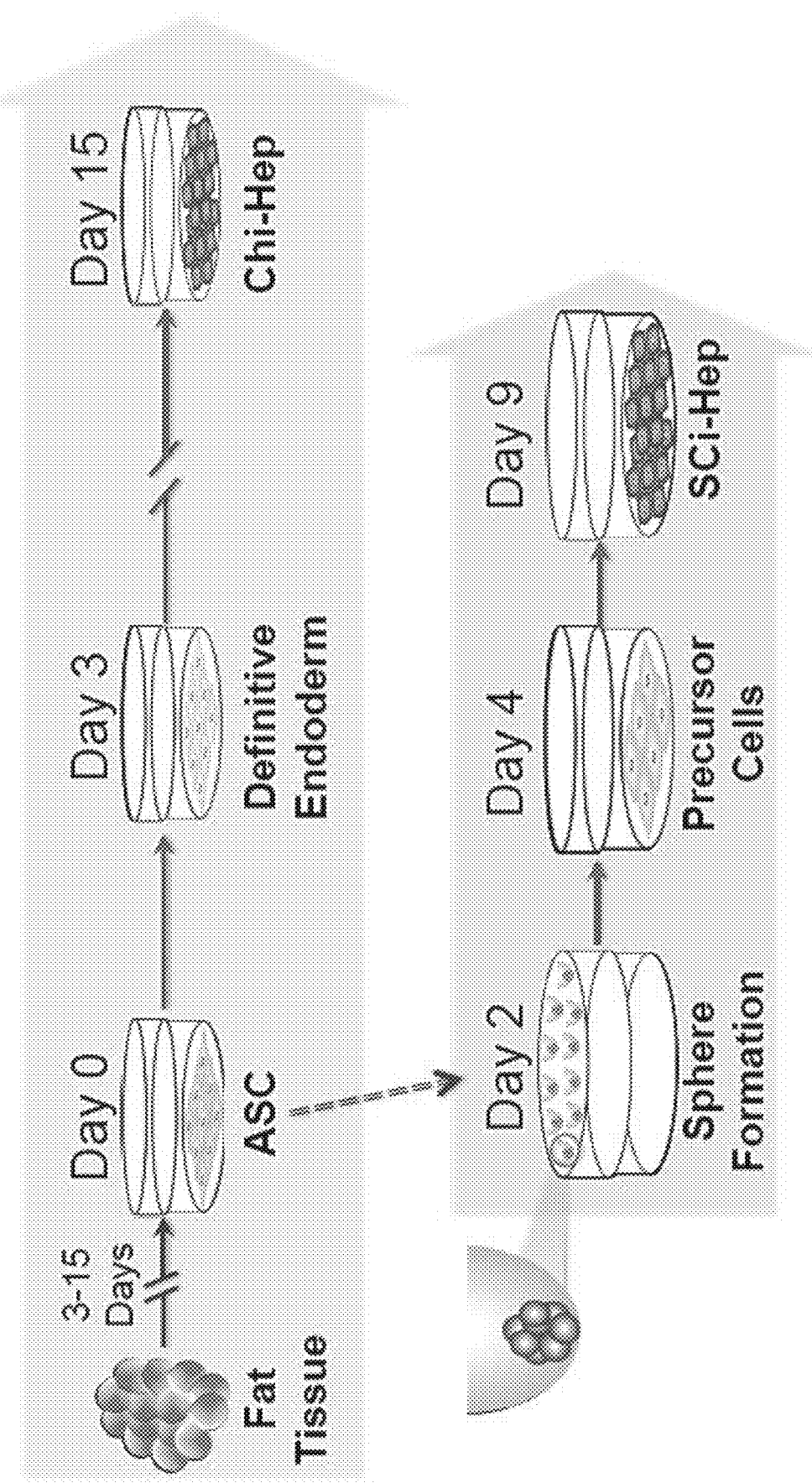
FIGS. 1A-1E provide a comparison of SCi-Heps to Chi-Heps, and a comparison of the methods of generating SCi-Heps and Chi-Heps.

Methods are provided for producing a population of hepatocyte-like cells (iHeps) from a population of adipocyte-derived stem cells (ASCs). Aspects of the methods include placing a population of ASCs into a three dimensional culture (e.g., hanging drop suspension culture, high density culture, spinner flask culture, microcarrier culture, etc.), and contacting the cells with a first and second culture medium. Also provided are methods of treating an individual, which include producing a population of iHeps from a population of ASCs, and administering an effective number of iHeps into the individual. Kits for practicing the methods are also described herein.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed Definitions The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member).

The term "specific binding agent" as used herein refers to any agent that specifically binds a biomolecule (e.g., a marker such as a nucleic acid marker molecule, a protein marker molecule, etc.). In some cases, a "specific binding agent" for a marker molecule (e.g., a hepatocyte marker molecule) is used. Specific binding agents can be any type of molecule. In some cases, a specific binding agent is an antibody or a fragment thereof. In some cases, a specific binding agent is nucleic acid probe (e.g., an RNA probe; a DNA probe; an RNA/DNA probe; a modified nucleic acid probe, e.g., a locked nucleic acid (LNA) probe, a morpholino probe, etc.; and the like)

As used herein, a "marker molecule" does not have to be definitive (i.e., the marker does not have to definitely mark the cell as being of a particular type. For example, the expression of a marker molecule by a cell can be indicative (i.e., suggestive) that the cell is of a particular cell type. For example, if 3 cell types (type A, type B, and type C) express a particular marker molecule (e.g., a particular mRNA, a particular protein, etc.), expression of that marker molecule by a cell cannot necessarily be used by itself to definitively determine that the cell is a type A cell. However, expression of such a marker can suggest that the cell is a type A cell. In some cases, expression of such a marker, combined with other evidence, can definitively show that the cell is a type A cell. As another illustrative example, if a particular cell type is known to express two or more particular marker molecules (e.g., mRNAs, proteins, a combination thereof, etc.) then the expression by a cell of one of the two or more particular marker molecules can be suggestive, but not definitive, that the cell is of the particular type in question. In such a case, the marker is still considered a marker molecule.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

A "TK-NOG mouse", as used herein refers to a mouse in which a herpes simplex virus type 1 thymidine kinase (HSVtk) transgene is expressed within the liver of a highly immunodeficient NOG mouse. Mouse liver cells expressing the HSVtk transgene can be ablated after a brief exposure to a non-toxic dose of ganciclovir (GCV). In some embodiments, an individual receiving treatment can be a mouse. For example, a TK-NOG mouse with ablated liver cells can be considered an individual with reduced liver function (i.e., an individual with liver damage) and the mouse can therefore be considered to be an individual receiving treatment when subject iHEPS (describe in detail below) are transplanted into the mouse. Transplanted human liver cells can be stably maintained within the liver of TK-NOG mice, and TK-NOG mice with transplanted human liver cells are referred herein as humanized TK-NOG mice. The reconstituted liver of humanized TK-NOG mice can be a mature and functioning human organ, and can generate a human-specific profile of drug metabolism. The 'humanized liver' can be stably maintained in humanized TK-NOG mice with a high level of function for a prolonged period (e.g., at least 8 months). For more information about TK-NOG mice, refer to: (i) Hasegawa et al, Biochem Biophys Res Commun. 2011 Feb. 18; 405(3):405-10; (ii) Yamazaki et al, Chem Res Toxicol. 2012 Feb. 20; 25(2):274-6; (iii) Hu et al., Pharmacogenet Genomics. 2013 Feb.; 23(2):78-83; and (iv) Yamazaki et al, Chem Res Toxicol. 2013 Mar. 18; 26(3):486-9; which are hereby incorporated by reference in their entirety.

The term "stem cell" is used herein to refer to a mammalian cell that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells can differentiate into lineage-restricted progenitor cells (e.g., adipocyte-derived stem cells), which in turn can differentiate into end-stage cells (e.g., adipocytes, osteoblasts, chondrocytes, etc.), which play a characteristic role in a certain tissue type, and may or may not retain the capacity to proliferate further. Stem cells (and differentiated progeny) may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

The stem cells of interest are mammalian, where the term refers to cells isolated from any animal classified as a mammal, including humans, domestic and farm animals, and zoo, laboratory, sports, or pet animals, such as dogs, horses, cats, cows, mice, rats, rabbits, etc. In some embodiments, the mammal is a human and the mammalian cells (e.g., a population of adipocyte-derived stem cells) are therefore human cells (e.g., a population of human adipocyte-derived stem cells).

The terms "passaging" or "passage" (i.e., splitting or split) in the context of cell culture are known in the art and refer to the transferring of a small number of cells into a new vessel. Cells can be cultured if they are split regularly because it avoids the senescence associated with high cell density. For adherent cells, cells are detached from the growth surface as part of the passaging protocol. Detachment is commonly performed with the enzyme trypsin and/or other commercially available reagents (e.g., TrypLE, EDTA (Ethylenediaminetetraacetic acid), a policemen (e.g., a rubber policemen) for physically scrapping the cells from the surface, etc.). A small number of detached cells (e.g., as few as one cell) can then be used to seed a new cell population, e.g., after dilution with additional media. Therefore, to passage a cell population means to dissociate at least a portion of the cells of the cell population, dilute the dissociated cells, and to plate the diluted dissociated cells (i.e., to seed a new cell population).

The terms "media" and "medium" are herein used interchangeably. Cell culture media is the liquid mixture that baths cells during in vitro culture.

The term "population", e.g., "cell population" or "population of cells", as used herein means a grouping (i.e., a population) of two or more cells that are separated (i.e., isolated) from other cells and/or cell groupings. For example, a 6-well culture dish can contain 6 cell populations, each population residing in an individual well. The cells of a cell population can be, but need not be, clonal derivatives of one another. A cell population can be derived from one individual cell. For example, if individual cells are each placed in a single well of a 6-well culture dish and each cell divides one time, then the dish will contain 6 cell populations. A cell population can be any desired size and contain any number of cells greater than one cell. For example, a cell population can be 2 or more, 10 or more, 100 or more, 1,000 or more, 5,000 or more, $10^4$ or more, $10^5$ or more, $10^6$ or more, $10^7$ or more, $10^8$ or more, $10^9$ or more, $10^{10}$ or more, $10^{11}$ or more, $10^{12}$ or more, $10^{13}$ or more, $10^{14}$ or more, $10^{15}$ or more, $10^{16}$ or more, $10^{17}$ or more, $10^{18}$ or more, $10^{19}$ or more, or $10^{20}$ or more cells.

Methods

Aspects of the disclosure include methods of producing a population of hepatocyte-like cells from a population of adipocyte-derived stem cells (ASCs). The methods generally involve placing a population of ASCs into a three dimensional culture (e.g., hanging drop suspension culture, high density culture, spinner flask culture, microcarrier culture, etc.) to produce an ASC-derived cellular aggregate (e.g., sphere); contacting cells of the ASC-derived cellular aggregate with a first culture medium comprising Activin A and a fibroblast growth factor (FGF) to produce a precursor cell population; and contacting cells of the precursor cell population with a second culture medium comprising hepatocyte growth factor (HGF) to produce an induced cell population that comprises induced hepatocyte-like cells (iHeps).

Adipose derived stem cells (ASCs). The term "adipose-derived stem cell" refers to a population of adipose cells found in post-natal mammals that are pluripotent and have the potential to differentiate into a variety of cell types including but not limited to cells of osteogenic, adipogenic, and chondrogenic lineages. ASCs can also differentiate into hepatocyte-like cells. ASCs have been referred to in the literature as adipose-derived adult stem (ADAS) cells, adipose-derived adult stromal cells, adipose-derived stromal cells (ADSCs), adipose stromal cells (ASCs), adipose mesenchymal stem cells (AdMSCs), lipoblast, pericyte, preadipocyte, and processed lipoaspirate (PLA) cells. The International Fat Applied Technology Society (IFATS) reached a consensus to adopt the term "adipose-derived stem cells" (ASCs) to identify the isolated, plastic-adherent, multipotent cell population. Thus, the term "Adipose-derived stem cell" (ASC) is used herein in accordance with the IFATS consensus, which will be known to one of ordinary skill in the art. In contrast to cell lines, ASCs have not undergone immortalization.

A number of scientific publications have described the underlying biology of ASCs, preclinical studies for the use of ASCs in regenerative medicine in various fields have been performed, and the efficacy of ASCs has been determined in several clinical trials.

ASCs for use in the subject methods can be isolated by any convenient methods, which will be known to one of ordinary skill in the art. Subcutaneous adipose tissue samples can generally be obtained under local anesthesia. Current methods used for isolating ASCs generally include collagenase digestion followed by centrifugal separation to isolate the Stromal Vascular Fraction from primary adipocytes.

As a non-limiting example, to isolate ASCs, adipose tissue obtained as excised surgical specimens (e.g., a biopsy) or as lipoaspirates can be digested with a collagenase enzyme (e.g., a bacterially-derived collagenase) in the presence of calcium to release the individual cell components. Subsequently, mature adipocytes can be separated (e.g., via differential centrifugation), from the remaining cells, which form a Stromal Vascular Fraction (SVF) pellet. The SVF cell population includes endothelial cells, fibroblasts, B and T-lymphocytes, macrophages, myeloid cells, pericytes, pre-adipocytes, smooth muscle cells, and the culture adherent ASCs. After culture (e.g., 4 to 6 days) with medium containing about 10% fetal bovine serum (any convenient culture medium can be used), a single milliliter of human lipoaspirate will yield between 0.25 to 0.375×$10^6$ ASCs capable of differentiating along the adipogenic (adipocyte), chondrogenic (chondrocyte), and osteogenic (osteoblast) lineages in vitro. ASCs display a fibroblast-like morphology and lack the intercellular lipid droplets seen in adipocytes. Isolated ASCs are typically expanded in monolayer culture on standard tissue culture plastics with a basal medium containing 10% fetal bovine serum. Since liposuction from a single patient often results in >1 L of tissue, it is feasible to generate hundreds of millions of ASCs from a single donor within a single in vitro cell culture passage In contrast to the SVF cells, ASCs are relatively homogeneous based on their expression profile of surface antigens.

In general, the isolation of ASCs from a lipoaspirate can include: (1) wash the lipoaspriate in buffered saline solution; (2) subject the lipoaspirate to collagenase digestion; (3) centrifuge and isolate the stromal vascular fraction (SVF) pellet; (4) culture the heterogeneous SVF cells on an adherent surface; and (5) isolate adherent ASCs. Culture of SVF cells under standard conditions eventually (within the first few passages) results in the appearance of ASCs, which is a relatively homogeneous population of mesodermal or mesenchymal cells. ASCs can be verified, for example, by demonstrating that the cells can differentiate into multiple different lineages (e.g., adipocytes can be identified using, for example, Oil Red O stain; osteoblasts can be identified using, for example, Alizarin Red stain; and chondrocytes can be identified using, for example, Alcian Blue stain). Protein and nucleic acid markers can also be used to verify differentiation into multiple lineages.

The International Society for Cellular Therapy (ISCT) and IFATS have established minimal criteria defining SVF cells and ASC based on functional and quantitative criteria. The four criteria used herein are: (1) ASCs are plastic-adherent when maintained under standard culture conditions; (2) ASCs have the capacity for osteogenic, adipogenic, and chondrogenic differentiation; (3) ASCs express the markers (i.e., molecular markers) CD29, CD34, CD36, CD49f, CD73, CD90 (Thy-1), CD105, CD133, c-kit, and c-met; and (4) ASCs are negative for CD45, CD106, and CD31. The adipocytic, chondroblastic and osteoblastic differentiation assays (e.g., Oil Red O stain, Alcian blue stain, and Alizarin red stain, respectively) can be used to assess potency and differentiation capacity, and can be used in conjunction with a quantitative evaluation of differentiation either biochemically or by reverse transcription polymerase chain reaction. The colony-forming unit-fibroblast (CFU-F) assay is recommended by the IFATS to calculate population doublings capacity of ASCs.

For more information regarding the nature of ASCs, including the isolation and culture of ASCs, see (i) Gimble et al., Circ Res. 2007 May 11; 100(9):1249-60: "Adipose-derived stem cells for regenerative medicine"; (ii) Gimble et al., Organogenesis. 2013 Jan. 1; 9(1): "Adipose-derived stromal/stem cells: A primer"; (iii) Bourin et al, Cytotherapy. 2013 Jun.; 15(6):641-8: "Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT)"; (iv) Gentile et al, Stem Cells Transl Med. 2012 Mar.; 1(3):230-6: "Concise review: adipose-derived stromal vascular fraction cells and platelet-rich plasma: basic and clinical implications for tissue engineering therapies in regenerative surgery"; and (v) Mizuno et al., Stem Cells. 2012 May; 30(5):804-10: "Concise review: Adipose-derived stem cells as a novel tool for future regenerative medicine"; all of which are hereby incorporated by reference in their entirety.

As used herein, the term "adipose tissue" refers to fat including the connective tissue that stores fat. Adipose tissue contains multiple regenerative cell types, including ASCs and endothelial progenitor and precursor cells.

Three dimensional culture. Methods of the disclosure include placing a population of ASCs into a three dimensional culture to produce an ASC-derived cellular aggregate (e.g., sphere). The term "three dimensional culture" as used herein refers to the culture of cells in a way that includes low shear force (and consequently low turbulence), and high mass transfer of nutrients. One non-limiting example of "three dimensional culture" is the culture of cells as aggregates (e.g., spheres, i.e., spheroid formation). Placing a population of cells (e.g., ASCs) into a three dimensional culture can cause the cells to form cellular aggregates (e.g., cellular spheres). Thus, subject cells (e.g., a population of ASCs) can be placed into a three dimensional culture to produce an ASC-derived cellular aggregate (e.g., sphere). Cellular aggregates (e.g., spheres) can be produced by a number of three dimensional culture techniques, including but not limited to hanging drop suspension culture, high density cell culture (e.g., stirred suspension culture such as spinner flask culture, e.g., with or without microcarriers; bioreactor culture, e.g., with or without microcarriers; etc.), and the like (see examples section).

In some embodiments, cells can be placed into a three dimensional culture at any convenient chosen density (e.g., via dilution or concentration). For example, in some cases, cells are placed into a three dimensional culture at a cell density in a range of from $1\times10^2$ cells/ml to $1\times10^7$ cells/ml (e.g., from $5\times10^2$ cells/ml to $5\times10^6$ cells/ml, from $1\times10^3$ cells/ml to $5\times10^6$ cells/ml, from $5\times10^3$ cells/ml to $5\times10^6$ cells/ml, from $5\times10^3$ cells/ml to $1\times10^5$ cells/ml, from $5\times10^3$ cells/ml to $5\times10^4$ cells/ml, from $7\times10^3$ cells/ml to $3\times10^4$ cells/ml, from $8\times10^3$ cells/ml to $3\times10^4$ cells/ml, $1\times10^4$ cells/ml, from $1\times10^4$ cells/ml to $1\times10^6$ cells/ml, from $5\times10^4$ cells/ml to $1\times10^6$ cells/ml, from $7\times10^4$ cells/ml to $7\times10^5$, from $1\times10^5$ cells/ml to $7\times10^5$, from $3\times10^5$ cells/ml to $7\times10^5$, from $4\times10^5$ cells/ml to $6\times10^5$, or $5\times10^5$).

In practicing the methods of the disclosure, ASCs can be cultured in three dimensional culture for a period of time sufficient for the formation of cellular aggregates (e.g., spheres, which can resemble embryoid bodies). In some embodiments, ASCs are cultured using three dimensional culture (i.e., ASCs are placed into a three dimensional culture) for 3 days or less (e.g., 2.5 days or less, 2 days or less, 1.5 days or less, 1 day or less, 12 hours or less, 8 hours or less, 6 hours or less, or 4 hours or less). In some embodiments, ASCs are cultured using three dimensional culture for a period of time in a range of from 2 hours to 3 days (e.g., from 2 hours to 3 days, from 2 hours to 2.5 days, from 2 hours to 2 days, from 2 hours to 1.5 days, from 2 hours to 1 day, from 6 hours to 3 days, from 6 hours to 2.5 days, from 6 hours to 2 days, from 6 hours to 1.5 days, from 6 hours to 1 day, from 6 hours to 12 hours, from 8 hours to 3 days, from 8 hours to 2.5 days, from 8 hours to 2 days, from 8 hours to 1.5 days, from 8 hours to 1 day, from 8 hours to 12 hours, from 12 hours to 2.5 days, from 12 hours to 2 days, from 12 hours to 1.5 days, from 12 hours to 1 day, from 1 day to 3 days, from 1 day to 2.5 days, from 1 day to 2 days, from 1 day to 1.5 days, from 1.5 days to 3 days, from 1.5 days to 2.5 days, from 1.5 days to 2 days, from 2 days to 3 days, from 1 day, 1.5 days, from 2 days, from 2.5 days, or 3 days).

Hanging drop suspension culture. In some embodiments, the three dimensional culture is a hanging drop suspension culture. Thus, in some embodiments, aggregates of subject cells (e.g., ASCs) are formed by placing the cells in a hanging drop suspension culture. Hanging drop suspension culture is a technique often used to form embryoid bodies from embryonic stem cells (ESCs). Cells in fluid are placed in droplets (usually in the range of 5-50 μl in size) onto a surface (e.g., surface of a Petri dish, a coverslip, glass, plastic etc.) and the surface is inverted such that the cells are suspended from the surface. The cells are thus cultured under the surface in a suspended droplet instead of being cultured on top of the surface. The suspended droplets are sometimes referred to as hanging drops. Some cells form aggregates, (referred to as 'spheres' and/or 'spheroids') when cultured using the hanging drop suspension culture.

In some embodiments, cells can be placed into hanging drop suspension culture at a chosen density (e.g., via dilution or concentration). For example, in some cases, cells are placed into hanging drop suspension culture at a cell density in a range of from $1\times10^2$ cells/ml to $1\times10^7$ cells/ml (e.g., from $5\times10^2$ cells/ml to $5\times10^6$ cells/ml, from $1\times10^3$ cells/ml to $5\times10^6$ cells/ml, from $5\times10^3$ cells/ml to $5\times10^6$ cells/ml, from $5\times10^3$ cells/ml to $1\times10^5$ cells/ml, from $5\times10^3$ cells/ml to $5\times10^4$ cells/ml, from $7\times10^3$ cells/ml to $3\times10^4$ cells/ml, from $8\times10^3$ cells/ml to $3\times10^4$ cells/ml, $1\times10^4$ cells/ml, from $1\times10^4$ cells/ml to $1\times10^6$ cells/ml, from $5\times10^4$ cells/ml to $1\times10^6$ cells/ml, from $7\times10^4$ cells/ml to $7\times10^5$, from $1\times10^5$ cells/ml to $7\times10^5$, from $3\times10^5$ cells/ml to $7\times10^5$, from $4\times10^5$ cells/ml to $6\times10^5$, or $5\times10^5$).

In practicing the methods of the disclosure, ASCs can be cultured by the hanging drop method (i.e., cultured using hanging drop suspension culture) for a period of time sufficient for the formation of cellular aggregates (e.g., spheres, which can resemble embryoid bodies). In some embodiments, ASCs are cultured using hanging drop suspension culture (i.e., ASCs are placed into a hanging drop suspension culture) for 3 days or less (e.g., 2.5 days or less, 2 days or less, 1.5 days or less, 1 day or less, 12 hours or less, 8 hours or less, 6 hours or less, or 4 hours or less). In some embodiments, ASCs are cultured using hanging drop suspension culture for a period of time in a range of from 2 hours to 3 days (e.g., from 2 hours to 3 days, from 2 hours to 2.5 days, from 2 hours to 2 days, from 2 hours to 1.5 days, from 2 hours to 1 day, from 6 hours to 3 days, from 6 hours to 2.5 days, from 6 hours to 2 days, from 6 hours to 1.5 days, from 6 hours to 1 day, from 6 hours to 12 hours, from 8 hours to 3 days, from 8 hours to 2.5 days, from 8 hours to 2 days, from 8 hours to 1.5 days, from 8 hours to 1 day, from 8 hours to 12 hours, from 12 hours to 2.5 days, from 12 hours to 2 days, from 12 hours to 1.5 days, from 12 hours to 1 day, from 1 day to 3 days, from 1 day to 2.5 days, from 1 day to 2 days, from 1 day to 1.5 days, from 1.5 days to 3 days, from 1.5 days to 2.5 days, from 1.5 days to 2 days, from 2 days to 3 days, from 1 day, 1.5 days, from 2 days, from 2.5 days, or 3 days).

In some embodiments, an ASC-derived cellular aggregate (e.g., sphere) is removed from three dimensional culture (e.g., hanging drop suspension culture, high density culture, spinner flask culture, microcarrier culture, etc.). For example, a cellular aggregate (e.g., sphere) can be suspended in fluid and plated onto a two-dimensional surfaced that is not considered a three dimensional culture. In some cases, aggregates (e.g., spheres) are collected (e.g., by centrifugation) and suspended. In some cases, the aggregates (e.g., spheres) are collected and suspended at a density in a range of from 15 aggregates/ml to 45 aggregates/ml (e.g., from 20 aggregates/ml to 40 aggregates/ml, from 25 aggregates/ml to 35 aggregates/ml, or 30 aggregates/ml). The aggregates can be suspended in any convenient media (e.g., stage 1 media, described below). In some cases, the collected (suspended) aggregates (e.g., spheres) are seeded (i.e., plated, e.g., onto matrigel-coated dishes). In some embodiments, an ASC-derived cellular aggregate (e.g., sphere) is removed from three dimensional culture (e.g., hanging drop suspension culture, high density culture, spinner flask culture, microcarrier culture, etc.) simultaneous with, or prior to, contacting cells of the ASC-derived cellular aggregate (e.g., sphere) with a stage 1 medium. Thus, in some cases, cells are cultured (e.g., contacted with) a stage 1 medium after being removed from three dimensional culture. In some embodiments, cells of the ASC-derived cellular aggregate (e.g., sphere) are contacted with a stage 1 medium while still in three dimensional culture (e.g., in order to transfer the cells to non-inverted culture conditions).

High density culture—microcarrier culture. In some embodiments, the three dimensional culture is a high density culture. Thus, aggregates (e.g., spheres) of subject cells (e.g., ASCs) are formed by placing the cells in a high density culture. In some embodiments, a high density culture is a microcarrier culture. In some embodiments, the three dimensional culture is a microcarrier culture. Thus, aggregates (e.g., spheres) of subject cells (e.g., ASCs) are formed by placing the cells in a microcarrier culture. The term "microcarrier culture" is used herein to refer to the culture of cells on a support matrix (e.g., a spherical support matrix). In this system, cells are propagated on the surface of small solid particles suspended in the growth medium by slow agitation. The cells attach and grow to confluence on the surface of the microcarriers.

Microcarriers can be produced in various shapes and sizes, spherical being the most common, and their density allows them to be maintained in suspension with gentle stirring. Each microcarrier should have dimensions that can facilitate cell growth for several doublings. In this way at the end of the cell growth, each microcarrier will support several hundred cells on its surface. Spherical microcarriers usually have diameters of 100-250 µm. In some embodiments, microcarriers are spheres with a diameter in a range of from 100 µm to 250 µm. The size distribution of the spherical microcarriers should be low (e.g., ±25 µm) in order to prevent uneven distribution of cells on the microcarriers. Density of the microcarriers should be slightly above 1 (e.g., 1.02-1.05 g/ml) in order to maintain the microcarriers in suspension at minimal agitation speed.

Microcarriers can be made from a number of different materials including diethylaminoethanol (DEAE)-dextran, dextran, glass, polystyrene plastic, acrylamide (e.g., polyacrylamide), collagen, etc. In some cases, biodegradable microcarriers can be used as the scaffold for in vivo transplantation of cells. The MC surface is available for cell growth while the mobility of MCs in the medium generates a homogeneity that is similar to the suspension environment used in traditional mammalian and microbial submerged cultures.

The surface of a microcarrier can be derivatized with functional groups such as recombinant proteins, positively charged tertiary quaternary or primary amines, gelatin, collagen, other extracellular matrix (ECM) proteins and peptides (e.g. RGD peptide). The positively charged MCs attract the cells (which are negatively charged), by electrostatic forces. The optimal amount of positive charge is generally found to be between 1 and 2 milliequivalents/g dry materials (for cross-linked dextran or polyacrylamide beads derivatized with tertiary amines). At this level, cells attach to the microcarriers efficiently (about 90% within 1 h) without negative effect on cell growth. Coating with collagen or ECM protein results in lower cell attachment but usually supports better growth of cells at low inoculation levels.

Several types of microcarriers are available commercially including dextran-based (Cytodex, GE Healthcare), collagen-based (Cultispher, Percell), and polystyrene-based (SoloHill Engineering) microcarriers. They differ in their porosity, specific gravity, optical properties, presence of animal components, and surface chemistries. It is possible to categorize the microcarriers into six groups:

Group 1: Non-porous smooth (e.g. polystyrene microcarriers) or microporous microcarriers (e.g. Cytodex 1) with positive charges. These microcarriers are suitable for culturing adherent cells that form a continuous monolayer of cells on the surface of the microcarriers in stirred cultures. This group includes also Whatman's anion exchange celluloses (DE-53), cylindrical shaped microcarriers that have been used successfully in culturing cell lines (BHK and MDCK).

Group 2: Collagen coated microcarriers (e.g. Cytodex 3 and FACT 102-L). These microcarriers are chemically coupled with collagen and are suitable for culturing sensitive cells with low plating efficiency. The collagen coating is also designed to facilitate cell harvesting.

Group 3: ECM coated microcarriers (Pro-F 102-L). Pro-F 102-L is coated with recombinant fibronectin which is designed for culturing of sensitive cells in serum free conditions.

Group 4: Non-charged microcarriers (e.g. Glass beads and tissue culture Polystyrene MC P 102-L). These microcarriers have similar surface properties as classical 2D tissue culture surfaces.

Group 5: Macroporous microcarriers (e.g. Cytopore and Cultispher). Macroporous microcarriers with pore sizes in the range of 10-70 µm on the surface. They provide higher cell surface areas for growth and offer better mechanical protection to the cells from shear stress generated by stirrers, spargers or spin filters.

Group 6: Weighted microcarriers (Cytoline). These microcarriers are designed for use in fluidized bed perfusion cultures. These commercial microcarriers have been designed according to the needs for propagating anchorage dependent cell lines used in production of vaccine and biopharmaceuticals.

In practicing the methods of the disclosure, ASCs can be cultured by microcarrier culture (i.e., cultured using microcarrier culture) for a period of time sufficient for the formation of cellular aggregates (e.g., spheres, which can resemble embryoid bodies). In some embodiments, ASCs are cultured using microcarrier culture (i.e., ASCs are placed into a microcarrier culture) for 3 days or less (e.g., 2.5 days or less, 2 days or less, 1.5 days or less, 1 day or less, 12 hours or less, 8 hours or less, 6 hours or less, or 4 hours or less). In some embodiments, ASCs are cultured using microcarrier culture for a period of time in a range of from 2 hours to 3 days (e.g., from 2 hours to 3 days, from 2 hours to 2.5 days, from 2 hours to 2 days, from 2 hours to 1.5 days, from 2 hours to 1 day, from 6 hours to 3 days, from 6 hours to 2.5 days, from 6 hours to 2 days, from 6 hours to 1.5 days, from 6 hours to 1 day, from 6 hours to 12 hours, from 8 hours to 3 days, from 8 hours to 2.5 days, from 8 hours to 2 days, from 8 hours to 1.5 days, from 8 hours to 1 day, from 8 hours to 12 hours, from 12 hours to 2.5 days, from 12 hours to 2 days, from 12 hours to 1.5 days, from 12 hours to 1 day, from 1 day to 3 days, from 1 day to 2.5 days, from 1 day to 2 days, from 1 day to 1.5 days, from 1.5 days to 3 days, from 1.5 days to 2.5 days, from 1.5 days to 2 days, from 2 days to 3 days, from 1 day, 1.5 days, from 2 days, from 2.5 days, or 3 days).

For examples of the use of microcarriers (e.g., using spinner flasks, bioreactors, etc.) for various purposes and with various types of cells, refer to scientific literature such as: (i) Chen et al, Biotechnol Adv. 2013 Mar. 24. pii: S0734-9750(13)00065-7: Application of human mesenchymal and pluripotent stem cell microcarrier cultures in cellular therapy: Achievements and future direction; (ii) Pacak et al, PLoS One. 2013; 8(1):e55187: Microcarrier-based expansion of adult murine side population stem cells; (iii) Torgan et al, Med Biol Eng Comput. 2000 September; 38(5):583-90: Differentiation of mammalian skeletal muscle cells cultured on microcarrier beads in a rotating cell culture system; and (iv) Park et al, Tissue Eng Part B Rev. 2013 Apr.; 19(2):172-90: Microcarriers designed for cell culture and tissue engineering of bone; as well as patent literature such as U.S. Pat. Nos. 8,524,492, 8,426,176, 7,947,471, 7,670,839, 7,361,493, 6,214,618, and 5,153,133, 4,910,142, and 4,824,946; all of which are hereby incorporated by reference in their entirety.

Microcarrier culture generally requires agitation of the microcarriers (e.g., the cell-loaded microcarriers). Agitation can include simple agitation or shaking, agitation using a spinner flask, and/or agitation using a bioreactor (also known as a rotating cell culture system (RCCS), a rotary cell culture system (RCCS), or a rotating chamber system).

Figure 13A:
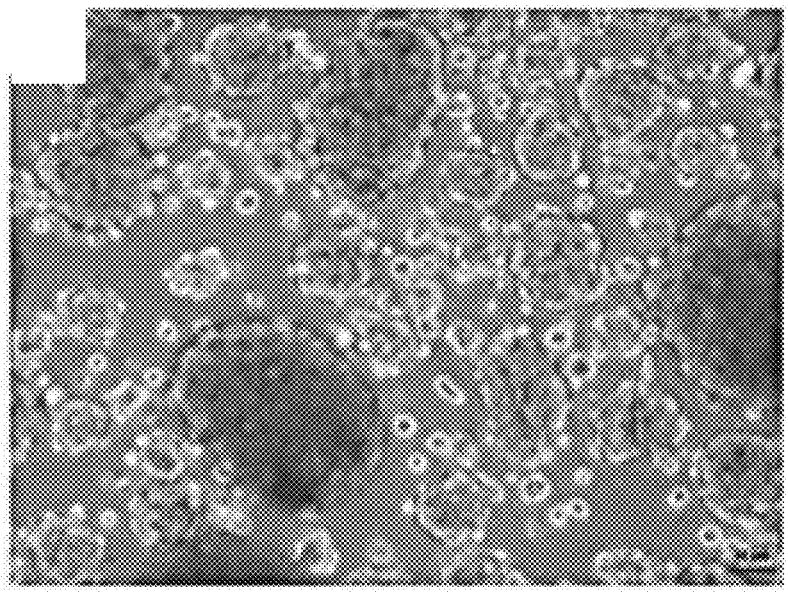
FIGS. 13A-13B demonstrate that ASCs cultured by stirred suspension culture (spinner flask culture in this case) form a high density of cellular aggregates that resemble the spheres formed during hanging drop suspension culture. Images shown are at 10× magnification.
Figure 13B:
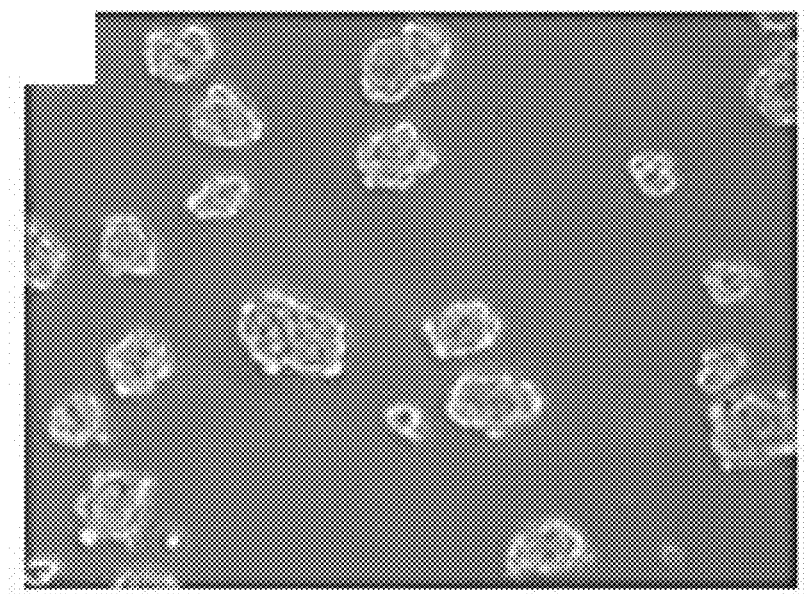

High density culture—Spinner flask culture. In some embodiments, the three dimensional culture is a high density culture. Thus, aggregates (e.g., spheres) of subject cells (e.g., ASCs) are formed by placing the cells in a high density culture. In some embodiments, a high density culture is a spinner flask culture. Spinner flask culture is an example of a stirred suspension culture. Stirred suspension culture (i.e., mass suspension culture)(e.g., spinner flask culture, bioreactor culture, etc.) can be used to culture cells in the absence of microcarriers or in the presence of microcarriers. Thus, in some embodiments, a microcarrier culture is agitated using a spinner flask. In some embodiments, a three dimensional culture (e.g., a high density culture) is a spinner flask culture without (i.e., in the absence of) microcarriers. In the absence of microcarriers, ASCs placed in stirred suspension culture (e.g., spinner flask culture, bioreactor culture) still form cellular aggregates (e.g., spheres)(FIG. 13). Thus, in some embodiments, a three dimensional culture (e.g., a high density culture) is a spinner flask culture without (i.e., in the absence of) microcarriers.

Spinner flasks (i.e., stirrer bottles) are generally designed to facilitate the culture of high volumes of cells by providing homogenous circulation of cells (e.g., cells in the absence of microcarriers, cells on microcarriers, etc.) and medium (i.e., nutrients), and superior gas exchange (e.g., oxygenation). Spinner flasks can be made of any convenient material (e.g., borosilicate glass, tissue culture grade plastics, etc.) and are usually a flat-bottom flask with a stirring device (e.g., usually a vertical impeller or a hanging stir bar) that can be controlled using a magnetic stir plate. A spinner flask can also include two angled side arms to allow for the introduction of pipettes. Any convenient spinner flask that provides for high density culture can be used in practicing the subject methods.

In some embodiments, cells can be placed into a spinner flask culture at any convenient chosen density (e.g., via dilution or concentration). For example, in some cases, cells are placed into a spinner flask culture at a cell density in a range of from $1\times10^2$ cells/ml to $1\times10^7$ cells/ml (e.g., from $5\times10^2$ cells/ml to $5\times10^6$ cells/ml, from $1\times10^3$ cells/ml to $5\times10^6$ cells/ml, from $5\times10^3$ cells/ml to $5\times10^6$ cells/ml, from $5\times10^3$ cells/ml to $1\times10^5$ cells/ml, from $5\times10^3$ cells/ml to $5\times10^4$ cells/ml, from $7\times10^3$ cells/ml to $3\times10^4$ cells/ml, from $8\times10^3$ cells/ml to $3\times10^4$ cells/ml, $1\times10^4$ cells/ml, from $1\times10^4$ cells/ml to $1\times10^6$ cells/ml, from $5\times10^4$ cells/ml to $1\times10^6$ cells/ml, from $7\times10^4$ cells/ml to $7\times10^5$, from $1\times10^5$ cells/ml to $7\times10^5$, from $3\times10^5$ cells/ml to $7\times10^5$, from $4\times10^5$ cells/ml to $6\times10^5$, or $5\times10^5$).

In practicing the methods of the disclosure, ASCs can be cultured by spinner flask culture (i.e., cultured using spinner flask culture) for a period of time sufficient for the formation of cellular aggregates (e.g., spheres, which can resemble embryoid bodies). In some embodiments, ASCs are cultured using spinner flask culture (i.e., ASCs are placed into a spinner flask culture) for 3 days or less (e.g., 2.5 days or less, 2 days or less, 1.5 days or less, 1 day or less, 12 hours or less, 8 hours or less, 6 hours or less, or 4 hours or less). In some embodiments, ASCs are cultured using spinner flask culture for a period of time in a range of from 2 hours to 3 days (e.g., from 2 hours to 3 days, from 2 hours to 2.5 days, from 2 hours to 2 days, from 2 hours to 1.5 days, from 2 hours to 1 day, from 6 hours to 3 days, from 6 hours to 2.5 days, from 6 hours to 2 days, from 6 hours to 1.5 days, from 6 hours to 1 day, from 6 hours to 12 hours, from 8 hours to 3 days, from 8 hours to 2.5 days, from 8 hours to 2 days, from 8 hours to 1.5 days, from 8 hours to 1 day, from 8 hours to 12 hours, from 12 hours to 2.5 days, from 12 hours to 2 days, from 12 hours to 1.5 days, from 12 hours to 1 day, from 1 day to 3 days, from 1 day to 2.5 days, from 1 day to 2 days, from 1 day to 1.5 days, from 1.5 days to 3 days, from 1.5 days to 2.5 days, from 1.5 days to 2 days, from 2 days to 3 days, from 1 day, 1.5 days, from 2 days, from 2.5 days, or 3 days).

High density culture—Bioreactor culture. In some embodiments, the three dimensional culture is a high density culture. Thus, aggregates (e.g., spheres) of subject cells (e.g., ASCs) are formed by placing the cells in a high density culture. In some embodiments, a high density culture is a bioreactor culture. Bioreactor culture is an example of a stirred suspension culture. Stirred suspension culture (i.e., mass suspension culture)(e.g., spinner flask culture, bioreactor culture, etc.) can be used to culture cells in the absence of microcarriers or in the presence of microcarriers. Thus, in some embodiments, a microcarrier culture is agitated using a bioreactor. In some embodiments, a three dimensional culture (e.g., a high density culture) is a bioreactor culture without (i.e., in the absence of) microcarriers. In the absence of microcarriers, ASCs placed in stirred suspension culture (e.g., spinner flask culture, bioreactor culture) still form cellular aggregates (e.g., spheres). Thus, in some embodiments, a three dimensional culture (e.g., a high density culture) is a bioreactor culture without (i.e., in the absence of) microcarriers.

Bioreactors (also known as a rotating cell culture system (RCCS), a rotary cell culture system (RCCS), or a rotating chamber system) can control environmental conditions such as gas (e.g., air, oxygen, nitrogen, carbon dioxide) flow rates, temperature, pH, dissolved oxygen levels, agitation speed/circulation rate, and the like. Like spinner flasks, bioreactors are designed to facilitate the culture of high volumes of cells by providing homogenous circulation of cells (e.g., cells in the absence of microcarriers, cells on microcarriers, etc.) and medium (i.e., nutrients), and superior gas exchange (e.g., oxygenation). Any convenient bioreactor that provides for high density cell culture can be used with the disclosed methods and various suitable bioreactors are known in the art. Examples of suitable biorecactors include, but are not limited to: rotating wall microgravity bioreactors, rotating wall vessel bioreactors (RWVB), stirred tank bioreactors, perfused bioreactors, fluidized bed bioreactors. Bioreactors can be made from a large variety of different materials, including, but not limited to: stainless steel, polytetraflouroethylene (PTFE), glass, and the like.

Bioreactors can allow for the scaling up of culture in, for example, conventional stainless steel or disposable bioreactors that are used for propagation of suspended mammalian cells. Bioreactors range in size. In some cases a bioreactor culture is a culture in the range of from 5 liters to 105 liters (e.g., from 5 liters to 15 liters, from 8 liters to 12 liters, from 15 liters to 25 liters, from 25 liters to 40 liters, from 40 liters to 50 liters, from 45 liters to 55 liters, from 55 liters to 65 liters, from 65 liters to 75 liters, from 75 liters to 85 liters, from 85 liters to 95 liters, or from 95 liters to 105 liters).

In some embodiments, cells can be placed into a bioreactor culture at any convenient chosen density (e.g., via dilution or concentration). For example, in some cases, cells are placed into a bioreactor culture at a cell density in a range of from $1 \times 10^2$ cells/ml to $1 \times 10^7$ cells/ml (e.g., from $5 \times 10^2$ cells/ml to $5 \times 10^6$ cells/ml, from $1 \times 10^3$ cells/ml to $5 \times 10^6$ cells/ml, from $5 \times 10^3$ cells/ml to $5 \times 10^6$ cells/ml, from $5 \times 10^3$ cells/ml to $1 \times 10^5$ cells/ml, from $5 \times 10^3$ cells/ml to $5 \times 10^4$ cells/ml, from $7 \times 10^3$ cells/ml to $3 \times 10^4$ cells/ml, from $8 \times 10^3$ cells/ml to $3 \times 10^4$ cells/ml, $1 \times 10^4$ cells/ml, from $1 \times 10^4$ cells/ml to $1 \times 10^6$ cells/ml, from $5 \times 10^4$ cells/ml to $1 \times 10^6$ cells/ml, from $7 \times 10^4$ cells/ml to $7 \times 10^5$, from $1 \times 10^5$ cells/ml to $7 \times 10^5$, from $3 \times 10^5$ cells/ml to $7 \times 10^5$, from $4 \times 10^5$ cells/ml to $6 \times 10^5$, or $5 \times 10^5$).

In practicing the methods of the disclosure, ASCs can be cultured in bioreactor culture for a period of time sufficient for the formation of cellular aggregates (e.g., spheres, which can resemble embryoid bodies). In some embodiments, ASCs are cultured using bioreactor culture (i.e., ASCs are placed into a bioreactor culture) for 3 days or less (e.g., 2.5 days or less, 2 days or less, 1.5 days or less, 1 day or less, 12 hours or less, 8 hours or less, 6 hours or less, or 4 hours or less). In some embodiments, ASCs are cultured using bioreactor culture for a period of time in a range of from 2 hours to 3 days (e.g., from 2 hours to 3 days, from 2 hours to 2.5 days, from 2 hours to 2 days, from 2 hours to 1.5 days, from 2 hours to 1 day, from 6 hours to 3 days, from 6 hours to 2.5 days, from 6 hours to 2 days, from 6 hours to 1.5 days, from 6 hours to 1 day, from 6 hours to 12 hours, from 8 hours to 3 days, from 8 hours to 2.5 days, from 8 hours to 2 days, from 8 hours to 1.5 days, from 8 hours to 1 day, from 8 hours to 12 hours, from 12 hours to 2.5 days, from 12 hours to 2 days, from 12 hours to 1.5 days, from 12 hours to 1 day, from 1 day to 3 days, from 1 day to 2.5 days, from 1 day to 2 days, from 1 day to 1.5 days, from 1.5 days to 3 days, from 1.5 days to 2.5 days, from 1.5 days to 2 days, from 2 days to 3 days, from 1 day, 1.5 days, from 2 days, from 2.5 days, or 3 days).

Culturing cells in differentiation media. The term "differentiation media" as used herein refers to media can be used to induce cells to differentiate. For example, stage 1 and stage 2 media (described below) are two types of differentiation media used to induce ASCs to differentiate into hepatocyte-like cells. In some embodiments, the methods include removing the ASC-derived cellular aggregate (e.g., sphere) from three dimensional culture (e.g., hanging drop suspension culture, high density culture, spinner flask culture, bioreactor culture, stirred suspension culture, microcarrier culture, etc.) and contacting cells of the ASC-derived cellular aggregate (e.g., for 3 days or less) with a first culture medium (e.g., stage 1 media) comprising Activin A and a fibroblast growth factor (FGF) to produce a precursor cell population. In some embodiments, cells of the precursor cell population are contacted with a second culture medium (e.g., stage 2 media) comprising hepatocyte growth factor (HGF) (e.g., for 7 days or less) to produce an induced cell population that comprises induced hepatocyte-like cells (iHeps). All proteins listed below that can be included in a suitable differentiation media, can be provided from any convenient source (e.g., purified from tissue, recombinant, etc.).

In some embodiments, cells of an ASC-derived cellular aggregate (e.g., sphere) are contacted with stage 1 media (as defined below, e.g., a culture medium having Activin A and an FGF) for 3 days or less (e.g., 2.5 days or less, 2 days or less, 1.5 days or less, 1 day or less, or 12 hours or less) to produce a precursor cell population. In some embodiments, cells of an ASC-derived cellular aggregate (e.g., sphere) are contacted with stage 1 media for a period of time in a range of from 12 hours to 3 days (e.g., 12 hours to 2.5 days, 12 hours to 2 days, 12 hours to 1.5 days, 12 hours to 1 day, 1 day to 3 days, 1 day to 2.5 days, 1 day to 2 days, 1 day to 1.5 days, 1.5 days to 3 days, 1.5 days to 2.5 days, 1.5 days to 2 days, 2 days to 3 days, 1 day, 1.5 days, 2 days, 2.5 days, or 3 days) to produce a precursor cell population.

In some embodiments, cells of the precursor cell population are contacted with stage 2 media (as defined below, e.g., a culture medium having hepatocyte growth factor (HGF)) for 8 days or less (e.g., 7.5 days or less, 7 days or less, 6.5 days or less, 6 days or less, 5.5 days or less, 5 days or less, 4.5 days or less, 4 days or less, 3.5 days or less, 3 days or less, 2.5 days or less, 2 days or less, 1.5 days or less, 1 day or less, or 12 hours or less) to produce an induced cell population that comprises induced hepatocyte-like cells. In some embodiments, cells of the precursor cell population are contacted with stage 2 media for a period of time in a range of from 12 hours to 8 days (e.g., 12 hours to 8 days, 1 day to 8 days, 2 days to 8 days, 3 days to 8 days, 4 days to 8 days, 5 days to 8 days, 6 days to 8 days, 2 days to 7 days, 3 days to 7 days, 4 days to 7 days, 5 days to 7 days, 6 days to 7 days, 5.5 days to 8 days, 5.5 days to 7.5 days, 5.5 days to 6.5 days, 6 days to 7.5 days, 6.5 days to 7.5 days, 1 day, 2 days, 3 days, or 3 days) to produce an induced cell population that comprises induced hepatocyte-like cells.

In some embodiments, the total time elapsed from (i) placing a population of ASCs into a three dimensional culture, to (ii) producing an induced cell population that comprises induced hepatocyte-like cells (iHeps), is less than 13 days (e.g., less than 12.5 days, less than 12 days, less than 11.5 days, less than 11 days, less than 10.5 days, less than 10 days, less than 9.5 days, less than 9 days, less than 8.5 days, less than 8 days, less than 7.5 days, less than 7 days, less than 6.5 days, less than 6 days, less than 5.5 days, less than 5 days, less than 4.5 days, or less than 4 days).

In some embodiments, the total time elapsed from (i) placing a population of ASCs into a three dimensional culture, to (ii) producing an induced cell population that comprises induced hepatocyte-like cells (iHeps), is 13 days or less (e.g., 12.5 days or less, 12 days or less, 11.5 days or less, 11 days or less, 10.5 days or less, 10 days or less, 9.5 days or less, 9 days or less, 8.5 days or less, 8 days or less, 7.5 days or less, 7 days or less, 6.5 days or less, 6 days or less, 5.5 days or less, 5 days or less, 4.5 days or less, or 4 days or less).

In some embodiments, the total time elapsed from (i) placing a population of ASCs into a three dimensional culture, to (ii) producing an induced cell population that comprises induced hepatocyte-like cells (iHeps), is in a range of from 12 hours to 13 days (e.g., from 1 day to 13 days, from 2 days to 13 days, from 3 days to 13 days, from 4 days to 13 days, from 4.5 days to 13 days, from 5 days to 13 days, from 5.5 days to 13 days, from 6 days to 13 days, from 6.5 days to 13 days, from 7 days to 13 days, from 7.5 days to 13 days, from 8 days to 13 days, from 8.5 days to 13 days, from 9 days to 13 days, from 9.5 days to 13 days, from 10 days to 13 days, from 10.5 days to 13 days, from 11 days to 13 days, from 11.5 days to 13 days, from 12 hours to 12.5 days, from 1 day to 12.5 days, from 2 days to 12.5 days, from 3 days to 12.5 days, from 4 days to 12.5 days, from 4.5 days to 12.5 days, from 5 days to 12.5 days, from 5.5 days to 12.5 days, from 6 days to 12.5 days, from 6.5 days to 12.5 days, from 7 days to 12.5 days, from 7.5 days to 12.5 days, from 8 days to 12.5 days, from 8.5 days to 12.5 days, from 9 days to 12.5 days, from 9.5 days to 12.5 days, from 10 days to 12.5 days, from 10.5 days to 12.5 days, from 11 days to 12.5 days, from 11.5 days to 12.5 days, from 12 hours to 12 days, from 1 day to 12 days, from 2 days to 12 days, from 3 days to 12 days, from 4 days to 12 days, from 4.5 days to 12 days, from 5 days to 12 days, from 5.5 days to 12 days, from 6 days to 12 days, from 6.5 days to 12 days, from 7 days to 12 days, from 7.5 days to 12 days, from 8 days to 12 days, from 8.5 days to 12 days, from 9 days to 12 days, from 9.5 days to 12 days, from 10 days to 12 days, from 10.5 days to 12 days, from 11 days to 12 days, from 3 days to 11 days, from 3 days to 10 days, from 3 days to 9.5 days, from 3 days to 9 days, from 6 days 10 days, or from 4 days to 10 days).

Basal cell culture media. Subject cells (e.g., ASCs, iHeps, differentiating ASCs, etc.) are cultured in an appropriate liquid nutrient medium, referred to herein as "basal cell culture media.". The stage 1 and stage 2 media are basal culture media supplemented with at least one additional component, as described below. Various basal media formulations are available (e.g., Dulbecco's Modified Eagle Medium (DMEM), RPMI, Iscove's medium, hepatocyte culture medium (HCM) (Lonza, Cat: cc-3198) etc.).

Any convenient culture media can serve as a basal culture medium. For example, a suitable tissue culture medium can contain components such as a vitamin; an amino acid (e.g., an essential amino acid, a non-essential amino acid, etc.); a pH buffering agent; a salt; an antimicrobial agent (e.g., an antibacterial agent, an antimycotic agent, etc.); serum (e.g., fetal bovine serum, human serum, calf serum, horse serum, goat serum etc.); an energy source (e.g., a sugar); a nucleoside; a lipid; trace metals; a cytokine; a growth factor; a stimulatory factor; additives (e.g., pyruvate (0.1-5 mM), glutamine (0.5-5 mM), etc.) and the like. Any convenient cell culture media can be used, and as is known in the art, various cell types grow better in particular media preparations. For example, in some cases, particular media formulations have been optimized to culture specific types of cells (e.g., ASCs, hepatocytes (hepatocyte culture medium (HCM) (Lonza, Cat: cc-3198)), neural progenitors, embryonic stem cells, etc.). Accordingly, any convenient cell culture media can be used as a basal culture media and may be tailored to the culture of ASCs and/or their differentiating progeny.

One exemplary, non-limiting, suitable basal medium is RPMI (Roswell Park Memorial Institute) 1640, which is well known in the art as a basal medium that allows the culture of mammalian cells with serum (Fetal Bovine Serum (FBS)) supplementation. Another suitable basal culture media is Advanced RPMI 1640, which is similar to classic RPMI 1640, but allows for serum supplementation to be reduced by 50-90% with no change in growth rate or morphology. Advanced RPMI 1640 can contain, for example, glucose, non-essential amino acids, sodium pyruvate, and phenol red. The complete formulation is readily available (e.g., online) to one of ordinary skill in the art for RPMI 1640, for Advanced RPMI 1640, and for many suitable commercially available basal culture media. Another suitable basal culture media is CLONETICS™ hepatocyte culture medium (HCM™) (available, ofr example, from Lonza—Catalog number 3198).

Stage 1 medium. "Stage 1 medium" is also referred to herein as a "first culture medium." A suitable stage 1 medium is a basal culture medium (e.g., advanced RPMI 1640, RPMI 1640, etc.) suitable for the culture of cells (e.g., ASCs, differentiating ASCs, etc.) supplemented with at least activin A (e.g., 100 ng/ml) and a fibroblast growth factor (e.g., FGF4, e.g., 20 ng/ml). In some cases, stage 1 medium includes a Wnt signaling agonist (e.g., Wnt3a, e.g., 50 ng/ml). In some cases, stage 1 medium includes a supplement such as B27 (e.g., 20%), which is known in the art. In some cases, a stage 1 medium includes a Wnt signaling agonist and a supplement (e.g., B27). In some cases, the basal culture media used for stage 1 media is advanced RPMI 1640 and it is supplemented with activin A (e.g., 100 ng/ml), FGF4 (e.g., 20 ng/ml), Wnt3a (e.g., 50 ng/ml), and 20% B27. In general, Stage 1 medium drives ASC differentiation toward the endoderm lineage.

Activins are dimeric proteins consisting of β subunits, which are connected by disulfide bonds. There are three different forms of activin: (i) homodimeric activin A (2 $\beta_A$ subunits); (ii) homodimeric activin B (2 $\beta_B$ subunits); and (iii) heterodimeric activin AB (1 $\beta_A$ and 1 $\beta_B$ subunit). The term "Activin A" as used herein refers to a homodimer of $\beta_A$ subunits. A $\beta_A$ subunit is the polypeptide also referred to as "Inhibin beta A chain" or "INHBA." The amino acid sequence of Inhibin beta A chain is:

```
                                             (SEQ ID NO: 1)
MPLLWLRGFLLASCWIIVRSSPTPGSEGHSAAPDCPSCALAALPKDV

PNSQPEMVEAVKKHILNMLHLKKRPDVTQPVPKAALLNAIRKLHVGK

VGENGYVEIEDDIGRRAEMNELMEQTSEIITFAESGTARKTLHFEIS

KEGSDLSVVERAEVWLFLKVPKANRTRTKVTIRLFQQQKHPQGSLDT

GEEAEEVGLKGERSELLLSEKVVDARKSTWHVFPVSSSIQRLLDQGK

SSLDVRIACEQCQESGASLVLLGKKKKKEEEGEGKKKGGGEGGAGAD

EEKEQSHRPFLMLQARQSEDHPHRRRRRGLECDGKVNICCKKQFFVS

FKDIGWNDWIIAPSGYHANYCEGECPSHIAGTSGSSLSFHSTVINHY

RMRGHSPFANLKSCCVPTKLRPMSMLYYDDGQNIIKKDIQNMIVEEC

GCS
```

In some embodiments, a subject stage 1 medium comprises Activin A at a concentration in a range of from about 50 ng/ml to about 150 ng/ml (e.g., from about 60 ng/ml to about 140 ng/ml, from about 70 ng/ml to about 130 ng/ml, from about 80 ng/ml to about 120 ng/ml, from about 85 ng/ml to about 115 ng/ml, from about 90 ng/ml to about 110 ng/ml, from about 95 ng/ml to about 105 ng/ml, from about 97.5 ng/ml to about 102.5 ng/ml, or about 100 ng/ml).

Fibroblast growth factors (FGFs) are a well described family of proteins (related by sequence, structure, and function), with 18 mammalian members. The FGFs are grouped into 6 subfamilies based on differences in sequence homology and phylogeny: FGFs 1 and 2; FGFs 3, 7, 10, and 22; FGFs 4-6; FGFs 8, 17, and 18; FGFs 9, 16 and 20; and FGFs 19, 21 and 23. In some cases, a suitable FGF is FGF 1, 2, 3, 4, 5, 6, 7, 8, 9, 10, 16, 17, 18, 20, and/or 22. In some cases, a suitable FGF is FGF4, FGF5, and/or FGF6. In some cases, a suitable FGF is FGF4.

The amino acid sequences of exemplary human FGFs are:

```
FGF1:
                                             (SEQ ID NO: 2)
MAEGEITTFTALTEKFNLPPGNYKKPKLLYCSNGGHFLRILPDGTVD

GTRDRSDQHIQLQLSAESVGEVYIKSTETGQYLAMDTDGLLYGSQTP

NEECLFLERLEENHYNTYISKKHAEKNWFVGLKKNGSCKRGPRTHYG

QKAILFLPLPVSSD
```

FGF2:

(SEQ ID NO: 3)
MVGVGGGDVEDVTPRPGGCQISGRGARGCNGIPGAAAWEAALPRRRP
RRHPSVNPRSRAAGSPRTRGRRTEERPSGSRLGDRGRGRALPGGRLG
GRGRGRAPERVGGRGRGRGTAAPRAAPAARGSRPGPAGTMAAGSITT
LPALPEDGGSGAFPPGHFKDPKRLYCKNGGFFLRIHPDGRVDGVREK
SDPHIKLQLQAEERGVVSIKGVCANRYLAMKEDGRLLASKCVTDECF
FFERLESNNYNTYRSRKYTSWYVALKRTGQYKLGSKTGPGQKAILFL
PMSAKS

FGF3:

(SEQ ID NO: 4)
MGLIWLLLLSLLEPGWPAAGPGARLRRDAGGRGGVYEHLGGAPRRRK
LYCATKYHLQLHPSGRVNGSLENSAYSILEITAVEVGIVAIRGLFSG
RYLAMNKRGRLYASEHYSAECEFVERIHELGYNTYASRLYRTVSSTP
GARRQPSAERLWYVSVNGKGRPRRGFKTRRTQKSSLFLPRVLDHRDH
EMVRQLQSGLPRPPGKGVQPRRRRQKQSPDNLEPSHVQASRLGSQLE
ASAH

FGF4:

(SEQ ID NO: 5)
MSGPGTAAVALLPAVLLALLAPWAGRGGAAAPTAPNGTLEAELERRW
ESLVALSLARLPVAAQPKEAAVQSGAGDYLLGIKRLRRLYCNVGIGF
HLQALPDGRIGGAHADTRDSLLELSPVERGVVSIFGVASRFFVAMSS
KGKLYGSPFFTDECTFKEILLPNNYNAYESYKYPGMFIALSKNGKTK
KGNRVSPTMKVTHFLPRL

FGF5:

(SEQ ID NO: 6)
MSLSFLLLLFFSHLILSAWAHGEKRLAPKGQPGPAATDRNPRGSSSR
QSSSSAMSSSSASSSPAASLGSQGSGLEQSSFQWSPSGRRTGSLYCR
VGIGFHLQIYPDGKVNGSHEANMLSVLEIFAVSQGIVGIRGVFSNKF
LAMSKKGKLHASAKFTDDCKFRERFQENSYNTYASAIHRTEKTGREW
YVALNKRGKAKRGCSPRVKPQHISTHFLPRFKQSEQPELSFTVTVPE
KKKPPSPIKPKIPLSAPRKNTNSVKYRLKFRFG

FGF6:

(SEQ ID NO: 7)
MALGQKLFITMSRGAGRLQGTLWALVFLGILVGMVVPSPAGTRANNT
LLDSRGWGTLLSRSRAGLAGEIAGVNWESGYLVGIKRQRRLYCNVGI
GFHLQVLPDGRISGTHEENPYSLLEISTVERGVVSLFGVRSALFVAM
NSKGRLYATPSFQEECKFRETLLPNNYNAYESDLYQGTYIALSKYGR
VKRGSKVSPIMTVTHFLPRI

FGF7:

(SEQ ID NO: 8)
MHKWILTWILPTLLYRSCFHIICLVGTISLACNDMTPEQMATNVNCS
SPERHTRSYDYMEGGDIRVRRLFCRTQWYLRIDKRGKVKGTQEMKNN
YNIMEIRTVAVGIVAIKGVESEFYLAMNKEGKLYAKKECNEDCNFKE
LILENHYNTYASAKWTHNGGEMFVALNQKGIPVRGKKTKKEQKTAHF
LPMAIT

FGF8:

(SEQ ID NO: 9)
MGSPRSALSCLLLHLLVLCLQAQEGPGRGPALGRELASLFRAGREPQ
GVSQQHVREQSLVTDQLSRRLIRTYQLYSRTSGKHVQVLANKRINAM
AEDGDPFAKLIVETDTFGSRVRVRGAETGLYICMNKKGKLIAKSNGK
GKDCVFTEIVLENNYTALQNAKYEGWYMAFTRKGRPRKGSKTRQHQR
EVHFMKRLPRGHHTTEQSLRFEFLNYPPFTRSLRGSQRTWAPEPR

FGF9:

(SEQ ID NO: 10)
MAPLGEVGNYFGVQDAVPFGNVPVLPVDSPVLLSDHLGQSEAGGLPR
GPAVTDLDHLKGILRRRQLYCRTGFHLEIFPNGTIQGTRKDHSRFGI
LEFISIAVGLVSIRGVDSGLYLGMNEKGELYGSEKLTQECVFREQFE
ENWYNTYSSNLYKHVDTGRRYYVALNKDGTPREGTRTKRHQKFTHFL
PRPVDPDKVPELYKDILSQS

FGF10:

(SEQ ID NO: 11)
MWKWILTHCASAFPHLPGCCCCCFLLLFLVSSVPVTCQALGQDMVSP
EATNSSSSSFSSPSSAGRHVRSYNHLQGDVRWRKLFSFTKYFLKIEK
NGKVSGTKKENCPYSILEITSVEIGVVAVKAINSNYYLAMNKKGKLY
GSKEFNNDCKLKERIEENGYNTYASFNWQHNGRQMYVALNGKGAPRR
GQKTRRKNTSAHFLPMVVHS

FGF16:

(SEQ ID NO: 12)
MAEVGGVFASLDWDLHGFSSSLGNVPLADSPGFLNERLGQIEGKLQR
GSPTDFAHLKGILRRRQLYCRTGFHLEIFPNGTVHGTRHDHSRFGIL
EFISLAVGLISIRGVDSGLYLGMNERGELYGSKKLTRECVFREQFEE
NWYNTYASTLYKHSDSERQYYVALNKDGSPREGYRTKRHQKFTHFLP
RPVDPSKLPSMSRDLFHYR

FGF17:

(SEQ ID NO: 13)
MGAARLLPNLTLCLQLLILCCQTQGENHPSPNFNQYVRDQGAMTDQL
SRRQIREYQLYSRTSGKHVQVTGRRISATAEDGNKFAKLIVETDTFG
SRVRIKGAESEKYICMNKRGKLIGKPSGKSKDCVFTEIVLENNYTAF
QNARHEGWFMAFTRQGRPRQASRSRQNQREAHFIKRLYQGQLPFPNH
AEKQKQFEFVGSAPTRRTKRTRRPQPLT

FGF18:

(SEQ ID NO: 14)
MYSAPSACTCLCLHFLLLCFQVQVLVAEENVDFRIHVENQTRARDDV
SRKQLRLYQLYSRTSGKHIQVLGRRISARGEDGDKYAQLLVETDTFG
SQVRIKGKETEFYLCMNRKGKLVGKPDGTSKECVFIEKVLENNYTAL
MSAKYSGWYVGFTKKGRPRKGPKTRENQQDVHFMKRYPKGQPELQKP
FKYTTVTKRSRRIRPTHPA

FGF20:

(SEQ ID NO: 15)
MAPLAEVGGFLGGLEGLGQQVGSHFLLPPAGERPPLLGERRSAAERS
ARGGPGAAQLAHLHGILRRRQLYCRTGFHLQILPDGSVQGTRQDHSL
FGILEFISVAVGLVSIRGVDSGLYLGMNDKGELYGSEKLTSECIFRE

-continued

```
QFEENWYNTYSSNIYKHGDTGRRYFVALNKDGTPRDGARSKRHQKFT

HFLPRPVDPERVPELYKDLLMYT
```

FGF22:

(SEQ ID NO: 16)
```
MRRRLWLGLAWLLLARAPDAAGTPSASRGPRSYPHLEGDVRWRRLFS

STHFFLRVDPGGRVQGTRWRHGQDSILEIRSVHVGVVVIKAVSSGFY

VAMNRRGRLYGSRLYTVDCRFRERIEENGHNTYASQRWRRRGQPMFL

ALDRRGGPRPGGRTRRYHLSAHFLPVLVS
```

In some embodiments, a subject stage 1 medium comprises an FGF (e.g., FGF4, FGF5, FGF6, etc.) at a concentration in a range of from 5 ng/ml to 50 ng/ml (e.g., from 5 ng/ml to 40 ng/ml, from 10 ng/ml to 40 ng/ml, from 10 ng/ml to 30 ng/ml, from 15 ng/ml to 25 ng/ml, from 17.5 ng/ml to 22.5 ng/ml, 15 ng/ml, 17.5 ng/ml, 20 ng/ml, 22.5 ng/ml, 25 ng/ml or 30 ng/ml).

Wnt signaling agonist—In some embodiments, a suitable "Stage 1 medium" includes a Wnt signaling agonist. A Wnt signaling agonist triggers the nuclear localization of β-Catenin and results in the activation of canonical Wnt signaling. There are two main branches of the Wnt signaling pathway: (1) the canonical β-Catenin dependent Wnt signaling pathway and (2) the non-canonical β-Catenin independent pathways, which include planar cell polarity (PCP) signaling as well as Calcium signaling (Gao, et. al, Cell Signal. 2010 May; 22(5):717-27. Epub 2009 Dec. 13). As used herein, the terms "Wnt signaling" and "Wnt/β-Catenin signaling" are used interchangeably to refer to the canonical β-Catenin dependent Wnt signaling pathway. As such, a "Wnt signaling agonist" increases output from the β-Catenin dependent Wnt signaling pathway. Activation of the Wnt pathway culminates when the protein β-Catenin enters the cell nucleus (for recent review of the canonical β-Catenin dependent Wnt signaling pathway see Clevers et. al., Cell. 2012 Jun. 8; 149(6):1192-205: Wnt/β-catenin signaling and disease). However, in the absence of Wnt signaling, free cytosolic β-Catenin is incorporated into a complex, known in the art as the β-Catenin destruction complex, which includes the proteins Axin, Adenomatous Polyposis Coli (APC), and glycogen synthase kinase (GSK-3β). Phosphorylation of β-Catenin by GSK-3β designates β-Catenin for the ubiquitin pathway and degradation by proteasomes (via βTRCP).

The binding of a canonical Wnt to its receptor (a Frizzled protein) leads to the activation of Dishevelled (Dvl) proteins, which inhibit glycogen synthase kinase-3β (GSK-3β) activity (i.e., phosphorylation of β-Catenin), leading to the cytosolic stabilization of β-Catenin. Stabilized β-Catenin then enters the nucleus and associates with the TCF/LEF (T Cell-specific transcription Factor/Lymphoid Enhancer Factor) family of transcription factors to induce transcription of important downstream target genes. Thus, in the absence of Wnt signaling, cytosolic (and therefore nuclear) levels of β-Catenin are kept low by negative regulatory components of the pathway while in the presence of Wnt signaling, cytosolic (and therefore nuclear) levels of β-Catenin are stabilized by positive regulatory components of the pathway.

By "negative regulatory components" of the Wnt pathway, it is meant proteins that function by antagonizing the Wnt pathway, thus resulting in decreased pathway output (i.e., decreased target gene expression). Examples of known negative regulatory components of the Wnt pathway include, but are in no way limited to: WIF, sFRP, Dkk, APCDD1, Notum, SOST, Axin, APC, GSK-3β, CK1γ, WTX, and βTrCP.

By "positive regulatory components" of the Wnt pathway, it is meant proteins that function by enhancing the Wnt pathway, thus resulting in increased pathway output (i.e., increased target gene expression). Examples of known positive regulatory components of the Wnt pathway include, but are in no way limited to: Wnt (e.g., Wnt1, Wnt3, Wnt3a, Wnt7a, and/or Wnt8), Norrin, R-spondin, PORCN, Wls, Frizzled, LRPS and LRP6, Tspan12, Lgr4, Lgr5, Lgr6, Dvl, β-Catenin, and TCF/LEF. In some embodiments, a subject Wnt signaling agonist is a positive regulatory component of the canonical Wnt signaling pathway (e.g., Wnt1, Wnt3, Wnt3a, Wnt7a, Wnt8, etc.).

In some embodiments, a subject Wnt signaling agonist is "specific for" or "specifically binds to" a component of the Wnt signaling pathway such that binding results in increased pathway output (i.e., transcription of target genes). The binding of an agonist can be mediated by covalent or non-covalent interactions or a combination of covalent and non-covalent interactions. When the interaction of the agonist with the component to which it specifically binds produces a non-covalently bound complex, the binding which occurs is typically electrostatic, hydrogen-bonding, or the result of lipophilic interactions. In particular, specific binding is characterized by the preferential binding of one member of a pair to a particular species relative to other species within the family of compounds to which the corresponding member of the binding member belongs. Thus, for example, a Wnt signaling agonist that is specific for the negative regulatory component GSK-3 preferably binds to GSK-3 relative to other proteins in the cell.

A subject Wnt signaling agonist is any molecule (e.g., a chemical compound; a non-coding nucleic acid, e.g., a non-coding RNA; a polypeptide; a nucleic acid encoding a polypeptide, etc.) that results in increased output (i.e., increased target gene expression) from the Wnt signaling pathway. For example, a Wnt signaling agonist can function by stabilizing, enhancing the expression of, or enhancing the function of a positive regulatory component of the pathway or by destabilizing, decreasing the expression of, or inhibiting the function of a negative regulatory component of the pathway. Thus, a Wnt signaling agonist can be a polypeptide positive regulatory component (e.g., Wnt3, wnt3a, Wnt1, and the like), and/or a nucleic acid encoding one or more positive regulatory components of the pathway. A Wnt signaling agonist can also be a small molecule or nucleic acid that stabilizes a positive regulatory component of the pathway either at the level of mRNA or protein.

In some embodiments, a Wnt signaling agonist functions by stabilizing β-Catenin, thus allowing nuclear levels of β-Catenin to rise. β-Catenin can be stabilized in multiple different ways. As multiple different negative regulatory components of the Wnt signaling pathway function by facilitating the degradation of β-Catenin, a subject Wnt signaling agonist can be a small molecule or nucleic acid inhibitor (e.g., microRNA, shRNA, etc.)(functioning at the level of mRNA or protein) of a negative regulatory component of the pathway. For example, in some embodiments, the Wnt signaling agonist is an inhibitor of GSK-3β. In some such embodiments, the inhibitor of GSK-3β is a small molecule chemical compound (e.g., TWS119, BIO, CHIR-99021, SB 216763, SB 415286, CHIR-98014 and the like). TWS119: 3-(6-(3-aminophenyl)-7H-pyrrolo[2,3-d]pyrimidin-4-yloxy)phenol (Ding et. al, Proc Natl Acad Sci USA. 2003 Jun. 24; 100(13):7632-7. Epub 2003 Jun. 6)

BIO: 6-bromo-3-[(3E)-1,3-dihydro-3-(hydroxyimino)-2H-indol-2-ylidene]-1,3-dihydro-(3Z)-2H-indol-2-one
or (2'Z,3'E)-6-Bromoindirubin-3'-oxime
(Meijer et. al, Chem Biol. 2003 Dec.; 10(12):1255-66)
CHIR-99021: 6-[[2-[[4-(2,4-dichlorophenyl)-5-(5-methyl-1H-imidazol-2-yl)-2-pyrimidinyl]amino]ethyl]amino]-3-pyridinecarbonitrile
(Bennett et al., J Biol Chem. 2002 Aug. 23; 277(34):30998-1004. Epub 2002 Jun. 7)
SB 216763: 3-(2,4-dichlorophenyl)-4-(1-methyl-1H-indol-3-yl)-1H-pyrrole-2,5-dione
(Cross et al., J Neurochem. 2001 April; 77(1):94-102)
SB 415286: 3-(3-chloro-4-hydroxyphenylamino)-4-(2-nitrophenyl)-1H-pyrrole-2,5-dione
(Cross et al., J Neurochem. 2001 April; 77(1):94-102)
CHIR-98014: N2-(2-(4-(2,4-dichlorophenyl)-5-(1H-imidazol-1-yl)pyrimidin-2-ylamino)ethyl)-5 nitropyridine-2,6-diamine
(Ring et al., Diabetes. 2003 March; 52(3):588-95)

Any convenient Wnt agonist may be used. In some embodiments, the Wnt agonist is Wnt3a. The amino acid sequence of human Wnt3a is:

```
                                        (SEQ ID NO: 17)
MAPLGYFLLLCSLKQALGSYPIWWSLAVGPQYSSLGSQPILCASIPG

LVPKQLRFCRNYVEIMPSVAEGIKIGIQECQHQFRGRRWNCTTVHDS

LAIFGPVLDKATRESAFVHAIASAGVAFAVTRSCAEGTAAICGCSSR

HQGSPGKGWKWGGCSEDIEFGGMVSREFADARENRPDARSAMNRHNN

EAGRQAIASHMHLKCKCHGLSGSCEVKTCWWSQPDFRAIGDFLKDKY

DSASEMVVEKHRESRGWVETLRPRYTYFKVPTERDLVYYEASPNFCE

PNPETGSFGTRDRTCNVSSHGIDGCDLLCCGRGHNARAERRREKCRC

VFHWCCYVSCQECTRVYDVHTCK.
```

In some cases, a subject stage 1 medium comprises Wnt3a at a concentration in a range of from about 20 ng/ml to about 80 ng/ml (e.g., from about 20 ng/ml to about 80 ng/ml, from about 25 ng/ml to about 75 ng/ml, from about 30 ng/ml to about 70 ng/ml, from about 35 ng/ml to about 65 ng/ml, from about 40 ng/ml to about 60 ng/ml, from about 45 ng/ml to about 55 ng/ml, from about 47.5 ng/ml to about 52.5 ng/ml, or about 50 ng/ml).

Stage 2 medium. "Stage 2 medium" is also referred to herein as a "second culture medium." A suitable stage 2 medium is a basal culture medium (e.g., hepatocyte culture medium (HCM™), advanced RPMI 1640, RPMI 1640, etc.) suitable for the culture of cells (e.g., differentiating ASCs, hepatocytes, etc.) supplemented with at least hepatocyte growth factor (HGF). In some cases, stage 2 medium includes a fibroblast growth factor (e.g., FGF4, e.g., 25 ng/ml).

In some embodiments, a stage 2 media further includes a component selected from: an FGF (e.g., FGF4, e.g., 25 ng/ml), oncostatinM (OSM, e.g., 30 ng/ml), dexamethasone (Dex, e.g., $2 \times 10^{-5}$ M), dimethyl sulfoxide (DMSO, e.g., 0.1%), and a combination thereof. In some cases, the basal culture media used for stage 2 media is CLONETICS™ (available, for example, from Lonza—Catalog number 3198) and it is supplemented with HGF (e.g., 150 ng/ml), an FGF (e.g., FGF4, e.g., 25 ng/ml), oncostatinM (e.g., 30 ng/ml), dexamethasone (e.g., $2 \times 10^{-5}$ M), and DMSO (e.g., 0.1%).

Hepatocyte growth factor (HGF) is a protein that functions as a potent mitogen, hepatotrophic factor, and/or a growth factor. The amino acid sequence of human HGF is:

```
                                        (SEQ ID NO: 18)
MWVTKLLPALLLQHVLLHLLLLPIAIPYAEGQRKRRNTIHEFKKSAK

TTLIKIDPALKIKTKKVNTADQCANRCTRNKGLPFTCKAFVFDKARK

QCLWFPFNSMSSGVKKEFGHEFDLYENKDYIRNCIIGKGRSYKGTVS

ITKSGIKCQPWSSMIPHEHSFLPSSYRGKDLQENYCRNPRGEEGGPW

CFTSNPEVRYEVCDIPQCSEVECMTCNGESYRGLMDHTESGKICQRW

DHQTPHRHKFLPERYPDKGFDDNYCRNPDGQPRPWCYTLDPHTRWEY

CAIKTCADNTMNDTDVPLETTECIQGQGEGYRGTVNTIWNGIPCQRW

DSQYPHEHDMTPENFKCKDLRENYCRNPDGSESPWCFTTDPNIRVGY

CSQIPNCDMSHGQDCYRGNGKNYMGNLSQTRSGLTCSMWDKNMEDLH

RHIFWEPDASKLNENYCRNPDDDAHGPWCYTGNPLIPWDYCPISRCE

GDTTPTIVNLDHPVISCAKTKQLRVVNGIPTRTNIGWMVSLRYRNKH

ICGGSLIKESWVLTARQCFPSRDLKDYEAWLGIHDVHGRGDEKCKQV

LNVSQLVYGPEGSDLVLMKLARPAVLDDFVSTIDLPNYGCTIPEKTS

CSVYGWGYTGLINYDGLLRVAHLYIMGNEKCSQHHRGKVTLNESEIC

AGAEKIGSGPCEGDYGGPLVCEQHKMRMVLGVIVPGRGCAIPNRPGI

FVRVAYYAKWIHKIILTYKVPQS.
```

In some embodiments, a subject stage 2 medium includes HGF at a concentration in a range of from 75 ng/ml to 250 ng/ml (e.g., from 100 ng/ml to 200 ng/ml, from 120 ng/ml to 180 ng/ml, from 125 ng/ml to 175 ng/ml, from 130 ng/ml to 170 ng/ml, from 135 ng/ml to 165 ng/ml, from 140 ng/ml to 160 ng/ml, from 145 ng/ml to 155 ng/ml, 120 ng/ml, 125 ng/ml, 130 ng/ml, 135 ng/ml, 140 ng/ml, 145 ng/ml, 150 ng/ml, 155 ng/ml, 160 ng/ml or 175 ng/ml).

In some embodiments, a subject stage 2 medium includes an FGF (e.g., FGF4) at a concentration in a range of from 5 ng/ml to 55 ng/ml (e.g., from 5 ng/ml to 45 ng/ml, from 10 ng/ml to 45 ng/ml, from 10 ng/ml to 35 ng/ml, from 15 ng/ml to 35 ng/ml, from 20 ng/ml to 30 ng/ml, from 22.5 ng/ml to 27.5 ng/ml, 15 ng/ml, 17.5 ng/ml, 20 ng/ml, 22.5 ng/ml, 25 ng/ml, 27.5 ng/ml, or 30 ng/ml).

Oncostatin M (OSM) is a polypeptide that functions as a cytokine and belongs to the interleukin 6 group of cytokines. The amino acid sequence of human OSM is:

```
                                        (SEQ ID NO: 19)
MGVLLTQRTLLSLVLALLFPSMASMAAIGSCSKEYRVLLGQLQKQTD

LMQDTSRLLDPYIRIQGLDVPKLREHCRERPGAFPSEETLRGLGRRG

FLQTLNATLGCVLHRLADLEQRLPKAQDLERSGLNIEDLEKLQMARP

NILGLRNNIYCMAQLLDNSDTAEPTKAGRGASQPPTPTPASDAFQRK

LEGCRFLHGYHRFMHSVGRVFSKWGESPNRSRRHSPHQALRKGVRRT

RPSRKGKRLMTRGQLPR
```

In some embodiments, a subject stage 2 medium includes oncostatinM (OSM) at a concentration in a range of from 10 ng/ml to 50 ng/ml (e.g., from 15 ng/ml to 45 ng/ml, from 20 ng/ml to 40 ng/ml, from 22.5 ng/ml to 37.5 ng/ml, from 25 ng/ml to 35 ng/ml, from 27.5 ng/ml to 32.5 ng/ml, 25 ng/ml, 27.5 ng/ml, 30 ng/ml, 32.5 ng/ml, or 35 ng/ml).

Dexamethasone (Dex) is a synthetic member of the glucocorticoid class of steroid drugs that has anti-inflammatory and immunosuppressant properties. Dex is also known as (11β,16α)-9-Fluoro-11,17,21-trihydroxy-16-methylpregna-1,4-diene-3,20-dione, 9α-Fluoro-16α-methyl-11β,17β,21-trihydroxy-1,4-pregnadiene-3,20-dione, 9α-Fluoro-16α-methylprednisolone, and Prednisolone F. Dex has the CAS number 50-02-2 and the chemical structure:

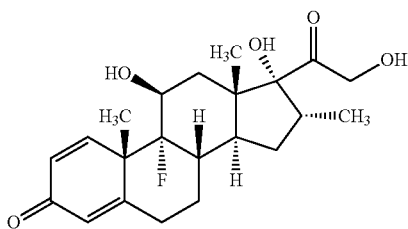

In some embodiments, a subject stage 2 medium comprises dexamethasone (Dex) at a concentration in a range of from $1 \times 10^{-6}$ M to $1 \times 10^{-4}$ M (e.g., from $5 \times 10^{-6}$ to $5 \times 10^{-5}$ M, from $1 \times 10^{-5}$ M to $3 \times 10^{-5}$ M, from $1.5 \times 10^{-5}$ M to $2.5 \times 10^{-5}$ M, or $2 \times 10^{-5}$ M).

Dimethylsulfoxide (DMSO) is an organosulfur compound with the formula $(CH_3)_2SO$ that is a colorless liquid and is a polar aprotic solvent that dissolves both polar and nonpolar compounds. DMSO is also known as Methyl sulfoxide, has the CAS number 67-68-5, and has the chemical structure:

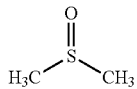

In some embodiments, a subject stage 2 medium comprises DMSO at a concentration in a range of from 0.01% to 1% (e.g., from 0.025% to 0.5%, from 0.05% to 0.2%, or 0.1%).

Hepatocyte-like cells. The term "hepatocyte-like cell" as used herein refers to a cell (e.g., of a cell population, e.g., a cell that is induced according to the subject methods) that is positive for (i.e., exhibits) one or more hepatocyte characters. Hepatocyte characters (i.e., characteristics of hepatocyte-like cells) include, but are not limited to:

(i) expression of (i.e., positive for) one or more hepatocyte markers (e.g., glucose-6-phosphatase, albumin (ALB), alpha-1-antitrypsin (AAT, also known as SERPINA1), cytokeratin 8 (CK8), cytokeratin 18 (CK18), cytokeratin 8/18 (CK8/18), asialoglycoprotein receptor 1 (ASGR1), alcohol dehydrogenase 1, arginase Type I, cytochrome p450 3A4 (CYP3A4), liver-specific organic anion transporter (LST-1), forkhead box protein A2 (FoxA2), alpha-fetoprotein (AFP), tryptophan 2,3-dioxygenase (TDO2), or a combination thereof);
(ii) activity of liver enzymes such as glucose-6-phosphatase, CYP3A4, and/or CYP1A1;
(iii) production and/or secretion of liver products (e.g., as measured in bodily fluids such as blood, serum, plasma, etc.)(e.g., bile, urea, and/or albumin);
(iv) exhibition of a hepatocyte metabolic properties (e.g., ability to detoxify xenobiotics; endocytosis of LDL, synthesis of glycogen, cytochrome P450 1A2 detoxification activity, and the like);
(v) exhibition of hepatocyte morphological features;

(vi) ability to engraft into the liver of an immunodeficient indidual (e.g., a mouse, a human, etc.); and
(vii) lack of expression of (negative for) one or more non-hepatocyte markers (e.g., adipocyte markers, e.g., CD37, CD29, etc.; ASC markers, e.g., CD105; and the like).

A subject hepatocyte-like cell does not have to be positive for all tested hepatocyte characters in order for the cell to be considered a hepatocyte-like cell. For example, in some cases, a subject hepatocyte-like cell is positive for all tested hepatocyte characters. However, in some cases, a subject hepatocyte-like cell is positive for one or more hepatocyte character; and is also negative for one or more hepatocyte characters. In some cases (described below in more detail), a hepatocyte-like cell is transplanted into an individual. In such cases, the hepatocyte-like cell can be (i) positive for all tested hepatocyte characters; or (ii) positive for one or more hepatocyte character(s); and negative for one or more hepatocyte character(s).

Thus, in some cases, hepatocyte-like cells do not express all known hepatocyte markers and/or test positive for all hepatocyte functional tests. For example, in some cases, hepatocyte-like cells that are induced according to the subject methods do not express ASGR1. However, as demonstrated in the examples section below (e.g., FIG. 3C), in some cases, hepatocyte-like cells exhibit a hepatocyte character (e.g., express a hepatocyte marker such as ASGR1) after transplantation (e.g., into an individual such as a mouse and/or a human) that they did not exhibit prior to transplantation. For example, in some cases, hepatocyte-like cells that are induced according to the subject methods do not express the hepatocyte marker ASGR1 prior to transplantation into an individual, but do express ASGR1 after transplantation. Thus, in some cases, it is not required that hepatocyte-like cells induced according to the subject methods exhibit all known hepatocyte characters (e.g., production of a liver product, expression of a hepatocyte marker, etc.) or even exhibit all tested hepatocyte characters prior to the use of the cells for transplantation. For example, in some cases, hepatocyte-like cells that are induced according to the subject methods are positive for one or more hepatocyte characters, and are negative for one or more hepatocyte characters, but are still considered hepatocyte-like cells and can still be transplanted into an individual.

In some embodiments, the subject methods include the step of verifying the presence of induced hepatocyte-like cells (iHeps) in the induced cell population. Verifying can rely on cellular phenotypes (e.g., gene or protein expression, drug metabolism profile, responsiveness to particular drugs, etc.) known in the art to be characteristic of hepatocytes. For example, verifying can be performed by testing for any one or more of the hepatocyte characters listed above (e.g., expression of a hepatocyte marker, lack of a expression of a non-hepatocyte marker, production and/or secretion of a liver product, activity of a liver enzyme, exhibition of to hepatocyte metabolic property, etc.). In some cases, verifying comprises determining the percentage of cells of the induced cell population that are iHeps.

In some embodiments, verifying includes contacting cells of the induced cell population with a specific binding agent (e.g., a nucleic acid probe, an antibody, etc.) specific for a hepatocyte marker (e.g., mRNA, protein, etc.), and determining the percentage of cells positive for expression, wherein cells positive for expression are iHeps. Suitable markers are listed above. In some embodiments, verifying includes contacting the induced cell population with a binding agent (e.g., a nucleic acid probe, an antibody, etc.)

specific for a non-hepatocyte marker (e.g., mRNA, protein, etc.), and determining the percentage of cells negative for expression, wherein cells negative for expression are iHeps. Suitable markers are listed above. In some cases, 10% or more of the cells of the induced cell population are determined to be iHeps (e.g., 10.5% or more, 11% or more, 12.5% or more, 15% or more, 17.5% or more, 20% or more, 22.5% or more, 25% or more, 27.5% or more, 30% or more, 32.5% or more, 35% or more, 37% or more, 40% or more, 45% or more, 50% or more, 55% or more, 60% or more, 65% or more, 70% or more, 75% or more, 80% or more, 85% or more, 90% or more, 95% or more, 98% or more, 99% or more, or 100%). In some embodiments, the percent of cells of the induced cell population that are determined to be iHeps is in a range of from 10% to 100% (e.g., from 10% to 90%, from 10% to 80%, from 10% to 70%, from 10% to 60%, from 10% to 50%, from 10% to 45%, from 10% to 100%, from 40% to 100%, from 10% to 37.5%, from 10% to 37%, from 15% to 90%, from 15% to 80%, from 15% to 70%, from 15% to 60%, from 15% to 50%, from 15% to 45%, from 15% to 100%, from 40% to 100%, from 15% to 37.5%, from 15% to 37%, from 20% to 90%, from 20% to 80%, from 20% to 70%, from 20% to 60%, from 20% to 50%, from 20% to 45%, from 20% to 100%, from 40% to 100%, from 20% to 37.5%, from 20% to 37%, from 25% to 90%, from 25% to 80%, from 25% to 70%, from 25% to 60%, from 25% to 50%, from 25% to 45%, from 25% to 100%, from 40% to 100%, from 25% to 37.5%, from 25% to 37%, from 30% to 90%, from 30% to 80%, from 30% to 70%, from 30% to 60%, from 30% to 50%, from 30% to 45%, from 30% to 100%, from 40% to 100%, from 30% to 37.5%, or from 30% to 37%).

It will be understood by those of skill in the art that expression levels reflect detectable amounts of the marker (e.g., nucleic acid or protein) on and/or in the cell. A cell that is negative for staining (e.g., the level of binding of a marker specific reagent is not detectably different from a matched control) may still express minor amounts of the marker. And while it is commonplace in the art to refer to cells as "positive" or "negative" for a particular marker, actual expression levels are quantitative traits. The number of detected molecules can vary by several logs, yet still be characterized as "positive".

When a protein marker is used, the staining intensity (e.g., of a marker-specific antibody) can be monitored by flow cytometry, where lasers detect the quantitative levels of fluorochrome (which is proportional to the amount of cell marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining brighter than that of an isotype matched control, but is not as intense as the most brightly staining cells normally found in the population. An alternative control may utilize a substrate having a defined density of marker on its surface, for example a fabricated bead or cell line, which provides the positive control for intensity.

Enrichment of hepatocyte-like cells. To increase the fraction of obtained cells that are iHeps, it is sometimes advantageous to enrich for (i.e., purify) the produced iHeps. In particular aspects, the hepatocyte-like cells provided herein may be selected or enriched by using a screenable or selectable reporter expression cassette comprising a mature hepatocyte-specific transcriptional regulatory element operably linked to a reporter gene, or by cell sorting (e.g., magnetic cell sorting, Fluorescence Activated Cell Sorting (FACS), and the like) using an antibody against a hepatocyte-specific marker (e.g., a cell surface antigen such as ASGR1).

To aid selection or enrichment, the ASCs, may comprise a selectable or screenable reporter expression cassette comprising a reporter gene. The reporter expression cassette may comprise a hepatocyte-specific transcriptional regulatory element operably linked to a reporter gene (e.g., any of the fluorescent proteins, e.g., blue, yellow, red, green, etc.). Non-limiting examples of hepatocyte-specific transcriptional regulatory element include a promoter of glucose-6-phosphatase, albumin (ALB), alpha-1-antitrypsin (AAT, also known as SERPINA1), cytokeratin 8 (CK8), cytokeratin 18 (CK18), asialoglycoprotein receptor 1 (ASGR1), alcohol dehydrogenase 1, arginase Type I, cytochrome p450 3A4 (CYP3A4), liver-specific organic anion transporter (LST-1), forkhead box protein A2 (FoxA2), alpha-fetoprotein (AFP), and tryptophan 2,3-dioxygenase (TDO2).

Enrichment using antibodies (e.g., magnetic cell sorting, FACS, and the like) specific for cell surface markers of ASCs (e.g., CD29, CD34, CD36, CD49f, CD73, CD90 (Thy-1), CD105, CD133, c-kit, c-met, and the like), endodermal precursor cells (e.g., SOX17), hepatocyte precursor/progenitor cells (e.g., N-cadherin, E-cadherin, EpCAM, and NCAM), and/or hepatocytes (e.g., ASGR1) have the advantage of not requiring genetic modification of the cells to be enriched. Magnetic cell sorting and FACS have the ability to analyze multiple surface markers simultaneously, and they can be used to sort ASCs, endodermal precursor cells, hepatocyte precursor/progenitor cells, and/or hepatocytes (e.g., iHeps) based on the expression of a cell surface marker. In some cases, iHeps do not express ASGR1. However, in some cases, e.g, if they are cultured longer and/or are further differentiated, iHeps do express ASGR1. In cases where cells that (i) do not express ASGR1; and/or (ii) express markers of hepatocyte precursor cells and/or endodermal precursor cells, are administered to an individual, the cells can further differentiate after administration into the individual (as demonstrated in the examples section below).

In some cases, cells that are produced by the subject methods can be enriched (e.g., sorted) by using an expressed cell surface marker. For example, cells of the precursor cell population (e.g., ASCs that have been contacted by a stage 1 medium) and/or cells of the induced cell population (e.g., cells of the precursor cell population that have been contacted with stage 2 medium) can be enriched using any marker that is expressed by hepatocyte precursor/progenitor cells (e.g., N-cadherin, E-cadherin, EpCAM, and NCAM) and/or endodermal precursor cells (e.g., SOX17). Cells of the induced cell population (e.g., cells of the precursor cell population that have been contacted with stage 2 medium) can be enriched using any marker that is expressed by hepatocyte precursor/progenitor cells (e.g., N-cadherin, E-cadherin, EpCAM, NCAM, etc.), endodermal precursor cells (e.g., SOX17), and/or hepatocytes (e.g., ASGR1) prior to further culture (e.g., to facilitate for further differentiation) and/or prior to administration to an individual. A cell population that includes ASCs (e.g., a population of cells from liposuction) can be enriched for ASCs using ASC cell surface markers (e.g., CD29, CD34, CD36, CD49f, CD73, CD90 (Thy-1), CD105, CD133, c-kit, c-met, and the like).

Cryopreservation. In some embodiments, subject cells (e.g., iHeps) are preserved for future use. Specifically, iHeps can be cryopreserved by performing the following steps: (i) Detach cells from growth cell surface, (ii) rinse cells (e.g., wash with PBS via centrifugation), (iii) resuspend cells (e.g., cell pellet) in media with 10% DMSO, and (vi) freeze cells and store in liquid nitrogen using standard tissue culture techniques commonly used in the art to preserve cells. Cells can be frozen at 1-50 million cells per vial. When ready for use, iHeps should be thawed in a manner as commonly known in the art for thawing frozen cultured cells.

Methods of Treatment

Aspects of the disclosure include methods of treating an individual. The subject methods of treatment generally include producing a population of hepatocyte-like cells from a population of adipose-derived stem cells (e.g., using the methods described above), and administering (e.g., injecting, transplanting, etc.) an effective number of hepatocyte-like cells into an individual. The ASCs can be from any source and can be derived by any convenient method. Exemplary methods of isolating/extracting/obtaining ASCs are described above. In some cases the ASCs are autologous (i.e., from the same individual into which the iHeps will be administered) (e.g., to reduce the possibility and/or severity of an immune response). In some cases, the ASCs are from a related individual (e.g., to reduce the possibility and/or severity of an immune response). In some cases, the ASCs are from an unrelated individual. In some cases, the ASCs are from an individual of another species (e.g., human ASCs administered to a mouse).

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted (e.g., those with liver malfunction, liver disease, liver damage, etc.) as well as those in which prevention is desired.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human.

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

In some embodiments, the individual to be treated is an individual with reduced liver function (e.g., an individual with liver damage). The term "liver damage" as used herein refers to any damage (e.g., caused by disease, trauma, unexplained, etc.) resulting in reduced liver function. An individual with reduced liver function (e.g., reduced relative to the individual's basal level of function; reduced relative to a healthy individual of comparable age, weight, sex, etc.; and the like) is referred to herein as an individual with a damaged liver (i.e., an individual with liver damage). Thus, the terms "liver damage" and "reduced liver function" are used synonymously herein. In some cases, an individual with "liver damage" is an individual with liver disease.

The cause for reduced liver function may be known or unknown. How to determine whether a given individual has reduced liver function (and therefore also how to determine whether an individual receiving treatment is recovering or has recovered liver function) will be known to one of ordinary skill in the art. Liver function tests can include liver enzyme tests, also known as liver function tests (LFTs), a group of blood tests that detect inflammation and damage to the liver. Blood protein markers of liver damage may include, for example: increased aspartate aminotransferase (AST), also known as SGOT; increased alanine aminotransferase (ALT), also known as SGPT; increased alkaline phosphatase; increased 5' nucleotidase; decreased albumin; decreased globulin; and increased gamma-glutamyl transpeptidase (GGT). If, for example, elevated amounts (and/or activity) of the above protein markers (or a decreased level for albumin and/or globulin) are detected in the blood, liver damage may be present. Additional liver function tests include: (i) prothrombin time (PT), a test of the time it takes for a blood sample to clot (e.g., if low levels of clotting factors are present, the prothrombin time is longer), which can be reported as international normalized ratio (INR) (a standardized way for laboratories to report PT so that results can be compared accurately across laboratories); and (ii) a bilirubin test: bilirubin blood levels may be elevated in people with impaired bile flow, which can occur in severe liver disease, gallbladder disease, or other bile system conditions.

Examples of symptoms, illnesses, and/or diseases that can be considered to indicate "liver damage" (and that can be treated by transplanting subject induced hepatocyte-like cells into an individual having the symptoms, illness, and/or disease), include, but are not limited to: acute liver failure, alcohol-related liver disease, Alagille syndrome, alpha 1-antitrypsin deficiency, alveolar hydatid disease, autoimmune hepatitis, bacillary peliosis, biliary atresia, Budd-Chiari syndrome, chronic liver disease, cirrhosis, congenital hepatic fibrosis, congestive hepatopathy, fatty liver, galactosemia, gastric antral vascular ectasia, Gilbert syndrome, hemochromatosis, hepatitis (A, B, and/or C), hepatic encephalopathy, hepato-biliary diseases, hepatolithiasis, hepatopulmonary syndrome, hepatorenal syndrome, hepatosplenomegaly, hepatotoxicity, hepatocellular carcinoma, hepatic encephalopathy, jaundice, Laennec's cirrhosis, liver abscess, liver cysts, liver cancer, liver failure, Lyngstadaas syndrome, non-alcoholic fatty liver disease, pediatric end-stage liver disease, peliosis hepatis, polycystic liver disease, primary biliary cirrhosis, primary sclerosing cholangitis (PSC), progressive familial intrahepatic cholestasis, Reye syndrome, type I glycogen storage disease, viral hepatitis, Wilson disease, Zahn infarct, and Zieve's syndrome.

In some cases, iHeps are cultured for a period of time prior to transplantation (e.g., in HCM™ for 2 days). Cells (e.g., iHeps) can be provided to the individual (i.e., administered into the individual) alone or with a suitable substrate or matrix, e.g. to support their growth and/or organization in the tissue to which they are being transplanted (e.g., liver). In some embodiments, the matrix is a scaffold (e.g., an organ scaffold). In some embodiments, $1\times10^3$ or more cells will be administered (e.g., transplanted), for example $5\times10^3$ or more cells, $1\times10^4$ or more cells, $5\times10^4$ or more cells, $1\times10^6$ or more cells, $5\times10^5$ or more cells, $1\times10^6$ or more cells, $5\times10^6$ or more cells, $1\times10^7$ or more cells, $5\times10^7$ or more cells, $1\times10^8$ or more cells, $5\times10^8$ or more cells, $1\times10^9$ or more cells, $5\times10^9$ or more cells, or $1\times10^{10}$ or more cells. In some embodiments, subject cells are administered into the individual on microcarriers (e.g., cells grown on biodegradable microcarriers).

The cells induced by the subject methods (iHeps) may be administered in any physiologically acceptable excipient (e.g., William's E medium), where the cells may find an appropriate site for survival and function (e.g., organ reconstitution). The cells may be introduced by any convenient method (e.g., injection, catheter, or the like).

The cells may be introduced to the subject (i.e., administered into the individual) via any of the following routes: parenteral, subcutaneous, intravenous, intracranial, intraspinal, intraocular, or into spinal fluid. The cells may be introduced by injection (e.g., direct local injection), catheter, or the like. Examples of methods for local delivery (e.g., delivery to the liver) include, e.g., by bolus injection, e.g. by a syringe, e.g. into a joint or organ; e.g., by continuous infusion, e.g. by cannulation, e.g. with convection (see e.g. US Application No. 20070254842, incorporated here by reference); or by implanting a device upon which the cells have been reversably affixed (see e.g. US Application Nos. 20080081064 and 20090196903, incorporated herein by reference).

In some cases, iHeps are administered into an individual by ultrasound-guided liver injection. In this way, cells can be placed directly into a liver lobe (e.g., in humans, or even in mice using a small animal ultrasound system). Brightness mode (B-mode) can be used to acquire two-dimensional images for an area of interest with a transducer and cells can be injected in solution (e.g., 100 μl to 300 μl, e.g., 200 μl of, for example, William's E medium) into one site or many sites (e.g., 1-30 sites) in the liver using, for example, a 30G needle.

The number of administrations of treatment to a subject may vary. Introducing cells into an individual may be a one-time event; but in certain situations, such treatment may elicit improvement for a limited period of time and require an on-going series of repeated treatments. In other situations, multiple administrations of iHeps may be required before an effect is observed. As will be readily understood by one of ordinary skill in the art, the exact protocols depend upon the disease or condition, the stage of the disease and parameters of the individual being treated.

A "therapeutically effective dose" or "therapeutic dose" is an amount sufficient to effect desired clinical results (i.e., achieve therapeutic efficacy). A therapeutically effective dose can be administered in one or more administrations. For purposes of this disclosure, a therapeutically effective dose of iHeps is an amount that is sufficient, when administered to (e.g., transplanted into) the individual, to palliate, ameliorate, stabilize, reverse, prevent, slow or delay the progression of the disease state (e.g., liver damage) by, for example, providing functions normally provided by a healthy liver. In some cases, transplanted iHeps integrate into the individual's liver and become part of the liver. In some cases, transplanted iHeps do not integrate into the individual's liver, but can still provide functions normally provided by a healthy liver.

In some embodiments, a therapeutically effective dose of iHeps is about $1\times10^3$ or more cells (e.g., $5\times10^3$ or more, $1\times10^4$ cells, $5\times10^4$ or more, $1\times10^5$ or more, $5\times10^5$ or more, $1\times10^6$ or more, $5\times10^6$ or more, $1\times10^7$ cells, $5\times10^7$ or more, $1\times10^8$ or more, $5\times10^8$ or more, $1\times10^9$ or more, $5\times10^9$ or more, or $1\times10^{10}$ or more). In some embodiments, a therapeutically effective dose of iHeps is in a range of from about $1\times10^3$ cells to about $1\times10^{10}$ cells (e.g, from about $5\times10^3$ cells to about $1\times10^{10}$ cells, from about $1\times10^4$ cells to about $1\times10^{10}$ cells, from about $5\times10^4$ cells to about $1\times10^{10}$ cells, from about $1\times10^5$ cells to about $1\times10^{10}$ cells, from about $5\times10^5$ cells to about $1\times10^{10}$ cells, from about $1\times10^6$ cells to about $1\times10^{10}$ cells, from about $5\times10^6$ cells to about $1\times10^{10}$ cells, from about $1\times10^7$ cells to about $1\times10^{10}$ cells, from about $5\times10^7$ cells to about $1\times10^{10}$ cells, from about $1\times10^8$ cells to about $1\times10^{10}$ cells, from about $5\times10^9$ cells to about $1\times10^{10}$, from about $5\times10^3$ cells to about $5\times10^9$ cells, from about $1\times10^4$ cells to about $5\times10^9$ cells, from about $5\times10^4$ cells to about $5\times10^9$ cells, from about $1\times10^5$ cells to about $5\times10^9$ cells, from about $5\times10^5$ cells to about $5\times10^9$ cells, from about $1\times10^6$ cells to about $5\times10^9$ cells, from about $5\times10^6$ cells to about $5\times10^9$ cells, from about $1\times10^7$ cells to about $5\times10^9$ cells, from about $5\times10^7$ cells to about $5\times10^9$ cells, from about $1\times10^8$ cells to about $5\times10^9$ cells, from about $5\times10^8$ cells to about $5\times10^9$, from about $5\times10^3$ cells to about $1\times10^9$ cells, from about $1\times10^4$ cells to about $1\times10^9$ cells, from about $5\times10^4$ cells to about $1\times10^9$ cells, from about $1\times10^5$ cells to about $1\times10^9$ cells, from about $5\times10^5$ cells to about $1\times10^9$ cells, from about $1\times10^6$ cells to about $1\times10^9$ cells, from about $5\times10^6$ cells to about $1\times10^9$ cells, from about $1\times10^7$ cells to about $1\times10^9$ cells, from about $5\times10^7$ cells to about $1\times10^9$ cells, from about $1\times10^8$ cells to about $1\times10^9$, from about $5\times10^3$ cells to about $5\times10^8$ cells, from about $1\times10^4$ cells to about $5\times10^8$ cells, from about $5\times10^4$ cells to about $5\times10^8$ cells, from about $1\times10^5$ cells to about $5\times10^8$ cells, from about $5\times10^5$ cells to about $5\times10^8$ cells, from about $1\times10^6$ cells to about $5\times10^8$ cells, from about $5\times10^6$ cells to about $5\times10^8$ cells, from about $1\times10^7$ cells to about $5\times10^8$ cells, from about $5\times10^7$ cells to about $5\times10^8$ cells, or from about $1\times10^8$ cells to about $5\times10^8$ cells).

The cells of this disclosure can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types.

Cells of the subject methods may be genetically altered in order to introduce genes useful in the differentiated hepatocytes, e.g. repair of a genetic defect in an individual, selectable marker, etc. Cells may also be genetically modified to enhance survival, control proliferation, and the like. Cells may be genetically altered by transfection or transduction with a suitable vector, homologous recombination, or other appropriate technique, so that they express a gene of interest. In some embodiments, a selectable marker is introduced, to provide for greater purity of the desired differentiating cell.

The cells of this disclosure can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in hepatocytes.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells (see Uchida et al. (1998) *P.N.A.S.* 95(20): 11939-44).

Combinations of retroviruses and an appropriate packaging line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) *Mol. Cell. Biol.* 5:431-437); PA317 (Miller et al. (1986) *Mol. Cell. Biol.* 6:2895-2902) GRIP (Danos et al. (1988) *PNAS* 85:6460-6464). Retroviruses packaged with xenotropic envelope protein, e.g. AKR env, are capable of infecting most mammalian cell types, except murine cells.

The vectors may include genes that must later be removed, e.g. using a recombinase system such as Cre/Lox, or the cells that express them destroyed, e.g. by including genes that allow selective toxicity such as herpesvirus TK, bcl-xs, etc. Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold.

Utility

The results described in the Examples below demonstrate that functioning human liver tissue can be generated in vivo after direct implantation of hepatocyte-like cells, derived from ASCs using the subject methods, into the liver. The SCi-Heps (iHeps induced using the subject methods) were produced from ASCs by in vitro differentiation for a short period in chemically defined media. SCi-Heps exhibited many of the in vitro functional properties of mature hepatocytes, and they were able to stably reconstitute functioning human liver in vivo in a murine model system, and implantation studies demonstrated that SCi-Heps have a very low malignant potential. Thus, readily-accessible stem cells were used to rapidly build functioning human liver tissue in vivo. The time to generate iHeps from ASCs is greatly reduced by the subject methods to under 13 days (e.g., 9 days). In addition, the efficiency of iHep production is greatly increased by the subject methods to greater that 10% (e.g., 37%). Both of these features facilitate treatment methods because liver damage (e.g., liver failure, e.g., due to acetaminophen toxicity) can rapidly cause death (e.g., in 2 weeks or less).

These procedures can be scaled to enable autologous liver regeneration in humans. Since there are ~140×$10^6$ hepatocytes per gram of human or mouse liver tissue; a 1500 gram adult human liver has ~2×$10^{11}$ hepatocytes, while a 1.8 gram mouse liver has 2.5×$10^6$ cells. After 1 million human hepatocytes are transplanted into a TK-NOG mouse, ~50% replacement of the mouse hepatocytes is routinely obtained, which amounts to ~1.2×$10^6$ functioning human hepatocytes in the mouse liver. This represents a 120-fold increase (or 7 population doublings) in the number of human hepatocytes generated in vivo relative to the number of transplanted cells. If a similar regeneration efficiency is achieved in humans, 800 million SCi-Heps ($10^{11}$/120) would be transplanted to replace 50% of the cells in a human liver. Of relevance to this question, 1 liter (1000 g) of lipo-aspirate can easily be obtained from a single liposuction procedure. This volume is estimated to contain 2-10×$10^9$ cells, of which 1-10% are estimated to be ASCs. Thus, one liter of lipo-aspirate contains between 2×$10^7$ and $10^9$ ASCs, which can provide a sufficient number of cells to enable autologous human liver replacement. Human liver regenerative procedures, including ultrasound-guided direct liver Implantation (used in the examples below), are scalable and appropriate for human clinical use.

The examples below demonstrate that spherical culture coupled with a chemical differentiation process can increase the yield of SCi-Heps by 7-fold compared to other known methods. Thus, the spherical culture method helps to ensure that a sufficient number of SCi-Heps can be obtained to enable liver regeneration in a human subject. The spherical culture method also reduces the culture volume by 12-fold and decreases the time in culture by 40%; these factors dramatically reduce the cost of differentiating ASC into iHeps. The estimated cost of the medium and growth factors required for producing Chi-Heps is ~$49,000 per liter of lipo-aspirate processed, but the subject method reduces these costs by over 20-fold (to ~$2400 per liter of lipo-aspirate processed).

The fact that implanted SCi-Heps did not form tumors (see the Examples below) indicates that these cells have a markedly reduced risk of causing tumors. In contrast to the results obtained with SCi-Heps, readily palpable tumors were noted within 3 weeks after implantation of iPS-Heps. The rapid tumor onset should not be surprising, since this iPS-derived cell population has a large percentage of un-differentiated cells. However, ~$10^9$ cells must be transplanted to regenerate a human liver, but even as few as 100-1000 cells with malignant potential in this population could cause tumor formation. These numbers create a very significant hurdle for any selective method used to prepare iPS-derived cells for liver regeneration. The fact that implanted SCi-Heps did not form tumors indicates that these cells have a markedly reduced risk of causing tumors to form. Since gancyclovir-induced liver damage in genetically engineered TK-NOG mice resembles the acute liver failure in humans that is caused by exogenous toxicants or drug overdose, methods disclosed here can provide cells that can be used to treat a damaged liver (e.g., a patient with acute liver failure).

Hepatocyte-like cells produced by the subject methods provide a source of donor cells for cell replacement in damaged livers. As such, the hepatocyte-like cells may be used for tissue reconstitution or regeneration in a human patient, an individual in need of such treatment, and/or for the reconstitution of human liver tissue in a non-human animal (e.g., a mouse, which can then be used, for example, for research purposes including drug screening, drug testing, etc.). The cells are administered in a manner that permits them to graft or migrate to the intended tissue site and reconstitute or regenerate the functionally deficient area.

The differentiated cells of this disclosure can also be used to prepare antibodies that are specific for markers of hepatocytes. Polyclonal antibodies can be prepared by injecting a vertebrate animal with cells of this disclosure in an immunogenic form. Production of monoclonal antibodies is described in such standard references as U.S. Pat. Nos. 4,491,632, 4,472,500 and 4,444,887, and Methods in Enzymology 736:3 (1981). Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

Gene expression may be examined before, during, and/or after the production of hepatocyte-like cells by the subject methods. The expressed set of genes may be compared against other subsets of cells, against progentior cells, against terminally differentiated hepatocytes, against ASCs, and the like, as known in the art. Any suitable qualitative or quantitative methods known in the art for detecting specific mRNAs can be used. mRNA can be detected by, for example, hybridization to a microarray, next-generation sequencing, in situ hybridization, by reverse transcriptase-polymerase chain reaction (rtPCR), or in Northern blots containing poly A mRNA. One of skill in the art can readily use these methods to determine differences in the size or amount of mRNA transcripts between two samples.

Any suitable method for detecting and comparing mRNA expression levels in a sample can be used in connection with the methods of the disclosure. For example, the mRNA from a sample can be sequenced via next-generation sequencing methods known in the art such as nanopore sequencing (e.g. as described in Soni et al Clin Chem 53: 1996-2001 2007, or as described by Oxford Nanopore Technologies), Illumina's reversible terminator method, Roche's pyrosequencing method (454), Life Technologies' sequencing by ligation (the SOLID platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps.

Alternatively, gene expression in a sample can be detected using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry).

Hybridization to arrays may be performed, where the arrays can be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an array are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., *Genome Res.* (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

In vitro induced hepatocyte-like cells (iHeps) produced by the subject methods provide also provide a source of cells for novel hepatic drug discovery, development, and safety testing. The use of in vitro iHeps produced by the subject methods offers the pharmaceutical industry an invaluable tool for preclinical screening of candidate drugs to treat cardiomyopathy, arrhythmia, and heart failure, as well as therapeutics to combat secondary cardiac toxicities. The development of new screens using In vitro iHeps produced by the subject methods should reduce the time and cost of bringing new drugs to market.

In screening assays for biologically active agents (e.g., small molecule compounds, peptides, viruses, etc.) of the subject hepatocyte-like cells, usually a culture comprising the subject hepatocyte-like cells, is contacted with the agent of interest, and the effect of the agent assessed by monitoring output parameters, such as expression of markers, cell viability, drug metabolism, and the like.

Agents of interest for screening include known and unknown compounds that encompass numerous chemical classes, primarily organic molecules, which may include organometallic molecules, inorganic molecules, genetic sequences, etc. An important aspect of the disclosure is to evaluate candidate drugs, including toxicity testing; and the like.

In addition to complex biological agents, such as viruses, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this disclosure are those described in, "The Pharmacological Basis of Therapeutics," Goodman and Gilman, McGraw-Hill, New York, New York, (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include manufacturing samples, pharmaceuticals, libraries of compounds prepared for analysis, and the like. Samples of interest include compounds being assessed for potential therapeutic value, i.e. drug candidates.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

The cells may be freshly isolated, cultured, genetically altered as described above, or the like. The cells may be environmentally induced variants of clonal cultures: e.g. split into independent cultures and grown under distinct conditions, for example with or without virus; in the presence or absence of other biological agents. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

For further elaboration of general techniques useful in the practice of this disclosure, the practitioner can refer to standard textbooks and reviews in cell biology, tissue culture, and embryology. With respect to tissue culture and stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

Kits

Also provided are kits for use in the subject methods. The subject kits include any combination of components for used in stage 1 and/or stage 2 media. For example, in some cases, a kit includes a Wnt signaling agonist (e.g., Wnt3a), activin A, an FGF (e.g., FGF4, FGF5, FGF6, etc.), and HGF. In some embodiments, a kit can further include oncostatinM, dexamethasone, and/or dimethyl sulfoxide. In some embodiments, a subject kit includes a basal media (e.g., RPMI 1640). In some embodiments, a subject kit includes an antibody specific for a hepatocyte marker protein for use in a verifying step (or an enrichment step). In some such embodiments, the hepatocyte marker protein is selected from the group consisting of: glucose-6-phosphatase, albumin (ALB), alpha-1-antitrypsin (AAT, also known as SERPINA1), cytokeratin 8 (CK8), cytokeratin 18 (CK18), cytokeratin 8/18 (CK8/18), asialoglycoprotein receptor 1 (ASGR1), alcohol dehydrogenase 1, arginase Type I, cytochrome p450 3A4 (CYP3A4), liver-specific organic anion transporter (LST-1), forkhead box protein A2 (FoxA2), alpha-fetoprotein (AFP), tryptophan 2,3-dioxygenase (TDO2), and a combination thereof. In some embodiments, a subject kit includes assay reagents (e.g, for measuring bile, albumin, and/or urea; for performing hepatocyte assays such as LDL endocytosis assays, glycogen synthesis assays, cytochrome P450 1A2 detoxification activity assays; and the like) for use in a verifying step.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (ph; seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM), millimolar (mM); molar (M); amino acids (aa); kilobases (kb); base pairs (bp); nucleotides (nt); intramuscular (i.m.); intraperitoneal (i.p.); subcutaneous (s.c.); and the like.

Disclosed here is an efficient, high-yield, cost-effective method for producing hepatocyte-like cells from adipose-derived stem cells. The hepatocyte-like cells produced by this method have many of the functional properties of mature hepatocytes in vitro, and can stably reconstitute a functioning human liver in vivo in a murine model system. The following materials and methods were used for Examples 1 and 2 below.

Materials and Methods

ASC preparation and differentiation. Lipo-aspirates were obtained as de-identified samples from human donors undergoing liposuction at Stanford University Medical Center according to protocol that was approved by the Stanford University Medical Center IRB. ASC were prepared from these samples as described (Banas et al, J Gastroenterol Hepatol. 2009 Jan.; 24(1):70-7, which is hereby incorporated by reference in its entirety). The ASC were cultured in MESENPRO RSTM Medium (Gibco, 12746-012), passaged at 90% confluence at a 1:4 ratio, and the medium was changed every other day. For preparation of Chi-Heps, after 2-5 passages, the ASC cells were plated on Martrigel (BD Biosciences, Cat: 354277) coated dishes. After the cells reached 50% confluence, endodermal trans-differentiation was induced over 3 days of culture in the stage 1 medium: RPM11640 (Gibco, Cat: 12633-012) supplemented with 100 ng/mL ActivinA (R&D, 338-AC-010), 50 ng/mL Wnt3a (StemRD, Cat: W3A-H-100), 20 ng/mL FGF4 (PeproTech, Cat: 100-31) and 20% B27 (Gibco Cat: 17504-044). Hepatic differentiation was then induced over a 13-15 day period by culture in the stage 2 medium: hepatocyte culture medium (HCM) (Lonza, Cat: cc-3198) supplemented with 150 ng/mL hepatocyte growth factor (HGF) (PeproTech, Cat: 100-39), 25 ng/mL FGF4, 30 ng/mL oncostatinM (OSM, PeproTech, Cat: 300-10), $2 \times 10^{-5}$ M dexamethasone (Dex, Sigma, Cat: D4902), and 0.1% DMSO (Sigma, Cat: C6164). The cells were then cultured in HCM alone for 2 days prior to transplantation into TK-NOG mice.

Preparation of SCi-Hep. Primary ASC were isolated from lipo-aspirates and suspended in MesenPRO RSTM Medium (Gibco, Cat: 12746-012) at $5 \times 10^4$ cells/ml. Then, the cells were cultured by the hanging drop method, which resulted in the formation of spherical cellular aggregates (spheres') that resembled embryoid bodies. Briefly, ASC were plated as individual drops (each ~40 ul) in rows on 150 mm petri dishes (BD Biosciences, Cat 354551) using an 8-channel pipette. After two days, the dishes were rinsed with PBS, and the spheres were collected by centrifugation at 150×g at 37° C., re-suspended at 30 spheres/ml in the stage 1 medium, and seeded on matrigel-coated dishes (BD Biosciences, Cat: 354262). The sphere derived cells were then induced to differentiate into hepatocytes by a 2-stage process. Endodermal transdifferentiation was induced over a 2-day period by culturing the spheres in the stage 1 medium. Hepatic differentiation was induced over the subsequent 2-9 day period by culture in the stage 2 medium. The cells were then cultured in HCM alone for 2 days prior to transplantation into TK-NOG mice.

Preparation of iPS-Heps. ASCs were transfected with Lentivirus encoding Oct4, Sox2, Klf4 and c-MYC to generate iPS cells. Four days after infection, the cells were re-plated at 5×104 cells per 100-mm matrigel (BD Biosciences, Cat: 354277) coated dish in mTeSR-1 medium (StemCell Technologies Inc, Cat: 05850), and the media was changed every other day. Fifteen days after infection, individual colonies were manually picked, and passaged onto new matrigelcoated dishes. After the cells reached 50% confluence, a three-stage hepatic differentiation protocol was then used. (i) iPS cells were cultured for 4 days in the stage 1 medium. (ii) Over the next 7 days, the cells were induced in hepatocyte progenitor (HP) medium containing RPMI1640 (Gibco, Cat: 12633-012) with 20% B27, 20 ng/ml BMP4 (Pepro Tech, Cat: 120-05ET) and 20 ng/ml FGF4 (PeproTech, Cat: 100-31). (iii) The cells were then placed for 15 days in a hepatocyte maturation (HM) medium, which had hepatocyte growth medium (Lonza, Cat: cc-3198) with 10 ng/ml HGF (PeproTech, Cat: 100-39), 10 ng/ml Oncostatin M (OSM, PeproTech, Cat: 300-10) and 0.1 uM dexamethasone (Dex, Sigma, Cat: D4902). The iPS cells used for differentiation were between passages 10 and 20.

Immunofluorescence staining. Cells were fixed in 4% paraformaldehyde for 10 min, followed by blocking with 10% chicken serum for 30 min. After washing 3 times in PBS with 0.05% Triton X-100) (TPBS), the cells were incubated with anti-human albumin (Bethyl Laboratories, Cat: A80-129A, 1:100) or anti-human CK8/18 (abcam, Cat: ab17139, 1:100) primary antibodies overnight at 4° C., and then washed three times with TPBS. Alexa Fluor 488 (Invitrogen, Cat: A21200, 1:1000) or Alexa Fluor 594 (Invitrogen, Cat: A21201, 1:1000)-conjugated secondary antibodies were then applied for one hour in the dark. Nuclear staining was assessed using 4,6-diamidino-2-phenylindole (DAPI, Sigma, Cat: D9542). The images were acquired using a Nikon Eclipse Ni-E imaging system.

For assessment of ASGR1 expression in vitro, the cells were permeablized with 0.2% Triton X-100 for 10 min followed by washing three times in PBS with 0.05% Triton X-100 (TPBS). The cells were pre-incubated with 10% chicken serum for 30 min, followed by incubation with a 1:50 dilution of Anti-ASGR1 antibody (Sigma-Aldrich cat #: HPA012852) primary antibody overnight at 4° C., and then washed three times with TPBS. Then, a 1:1000 dilution of Alexa Fluor 488 (Invitrogen, Cat #: A21200,)-conjugated secondary antibody was applied for one hr in the dark. Nuclear staining was assessed using 4,6-diamidino-2-phenylindole (DAPI, Sigma-Aldrich, Cat #: D9542). The images were acquired using a Nikon Eclipse Ni-E imaging system.

Periodic Acid-Schiff (PAS) Staining. PAS staining was performed according to the manufacturer's (Sigma, 395B) instructions. Briefly, the cells were fixed with 4% paraformaldehyde for 1 min. After rinsing with distilled water, the cells were stained with PAS solution for 5 min, then washed with distilled water, and stained using Schiff's reagent for 15 min. The cells were then washed once with water and counter-stained in hematoxylin solution for 90 sec; followed by rinsing 3 times with distilled water prior to analysis.

LDL endocytosis. LDL uptake was assessed using the Dil-LDL assay (Biomedical Technologies Inc., BT-904) according to the manufacturer's instruction. The cells were pre-incubated in serum-free medium with 1% BSA for 24 hr. Then 10 ug/mL Dil-LDL was added for at least five hours at 37° C. After washing 3 times with DPBS, the cells were imaged using were imaged using Nikon Eclipse Ni-E imaging system.

Flow cytometry. CK8/18 expression was analyzed by flow cytometry (FACS, Aida, Software Flowjo). The cells were first blocked with an Fc receptor-blocking reagent (Miltenyi Biotech, Germany) according to the manufacturer's instructions, and then stained with primary antibody anti-human CK8/18 (abcam, Cat: ab17139, 1:200) for 30 min at 4° C., which was followed by incubation with a secondary antibody Alexa Fluor 488 (Invitrogen, Cat: A21200, 1:1000). Appropriately diluted isotype-matched antibodies (Ebioscience) were used as controls. The data from 10,000 analyzed events were stored and analyzed.

Human albumin production. Human albumin production was evaluated using enzyme linked immunosorbent assay (ELISA, E80-129; Bethyl Laboratories, Montgomery, Tex., USA), which uses a human-specific antibody that does not cross-react with mouse albumin. Briefly, cell culture supernatants were collected on day 0 and every three days afterwards. The supernatants were concentrated using Amicon® Ultra-4 centrifugal filter units (EMD Millipore, UFC810024). Blood samples were first centrifuged at 2000 g for 5 min to isolate sera, and then diluted at 1:10000 for assay. Each data point is the mean±SE of 4 biologically independent samples analyzed.

Urea production and CYP450 activity. Cellular urea production was detected in un-diluted cell culture supernatants using a urea assay kit (abcam, ab83362) according to the manufacturers instructions. Cellular CYP450 activity was measured using the P450-Glo™ CYP3A4 assay (Promega, Cat: V9002) according to the manufacturers instructions. In brief, the cells were cultured with medium containing a luminogenic CYP substrate at 37° C. for 60 min. Then, 25 μl of supernatant was transferred to 96-well opaque white luminometer plate at room temperature, and 25 μl of luciferin detection reagent was added to initiate the luminescent reaction. After a 20 min incubation, luminescence was measured using an IVIS 100 Imaging System.

RT-PCR analysis. Total RNA was extracted using RNeasy Plus kit (Qiagen, Cat: 74134) and (0.5 µg) was reverse-transcribed using the SuperScript III Reverse Transcriptase (Invitrogen, Cat #11754-050) according to the manufacturer's guidelines. PCR analyses were performed using the following TaqMan gene expression assays: FOXA2 (Hs00232764_m1), AFP (Hs00173490_m1), ALB (Hs99999922_s1), AAT (Hs01097800_m1), A1AT (Hs00165475_m1), TDO2 (Hs00194611_m1), CD37 (Hs01099648_m1), and CD29 (Hs00559595_m1), and CD105 (Hs00923996_m1). For statistical analysis of the RT-PCR data, the measured expression levels for each of the analyzed genes on the indicated day were normalized relative to its level of expression in ASC. Then, a one-sample t-test was applied using the log-transformed expression level to assess the statistical significance of the expression changes.

Microarray analysis of gene expression. Total RNA was harvested and separately processed from 3 independently prepared cultures of each cell type according to the manufacturer's instructions. In brief, cells were detached from the dish using the StemPro Accutase® Cell Dissociation Reagent (Invitrogen, Cat: A11105-01). RNA was extracted using the RNeasy Mini Kit (QIAGEN, Cat: 74104), and 10 ug RNA was labeled, and hybridized to Affymetrix Human Genome U219 Arrays, and processed according to the manufacturer's instructions. The resulting image files were analyzed using Affymetrix Microarray Analysis Suite version 5.0 software. Three biological replicates were analyzed for ASC, Chi-Hep, SCi-Hep, iPS-Hep and hepatocyte cells. The probe intensity data generated from all arrays were read into the R software environment ("""www." followed by "R-project.org", version 2.15.1) directly from the .CEL files using the R/affy package (Gautier et al, Bioinformatics. 2004 Feb. 12; 20(3):307-15), which was also used to extract and manipulate probe level data to assess data quality and to create expression summary measures. Normalization was carried out using the robust multiarray average (RMA) method (Irizarry et al, Biostatistics. 2003 Apr.; 4(2):249-64) to generate one expression measure for each probe set on each array. Student's t-test was applied to identify the expression changes in iHep, iPS-Hep and hepatocyte cells as compared to the ASC cells. The empirical Bayes method (Smyth et al, Stat Appl Genet Mol Biol. 2004; 3: Article3) was applied to adjust the standard deviation estimation for each probe, and a multipletesting adjustment was applied to generate the final the p-values using the R/limma package. Gene expression changes meeting pre-determined criteria (fold-change>2 and adjusted pvalue <0.01) were selected for further analysis.

For illustration of the spatial relationship of the gene expression profiles of these cells, we defined the distance between any pair of array data as the squared root of the sum of the squares of the difference in the level of expression for each gene on the microarray:

$$\text{Dist}(\text{Array1}, \text{Array2}) = \sqrt{\sum_{i=1}^{N} (E_{1i} - E_{2i})^2}$$

where N represents the total number of probes on the array and $E_{1i}$ and $E_{2i}$ present the log 2 of the normalized expression level for probe i on array 1 and 2, respectively. In other words, the distance for a pair of profiles is the Euclidean distance between the two profiles treated as a vector of size N. Since there are 3 replicated arrays for each cell type, we defined the distance between any two cell types as the average of the distances measured when each of the 3 arrays for one cell type was compared with each of the 3 arrays for the other cell type (which produces a total of 9 array pairs) The 2-dimensional illustration of the spatial relationship among the 4 cell types was created by putting two triangles, which share the common ASC-hepatocyte axis next to each other. The length of each side of a triangle is proportional to the distance between the cell types at the indicated vertices.

Principle component analysis (PCA) was also used to visualize the relatedness of the overall patterns of the gene expression in the different types of cells analyzed. In brief, the dimension that explained the largest amount of the variation in the profiles was identified, and this became the 1st principle component (PC) shown on the x-axis. Then the dimension that was orthogonal to PC 1 and explained the largest amount of the remaining variation was identified, which became the 2nd PC shown on the y-axis. As a result, the first two components captured the majority of the variation in the data. Therefore, visualization could be focused on these components to reduce dimension without losing a significant amount of information present in the original data.

Preparation of TK-NOG mice. All animal experiments were performed according to protocols approved by the Stanford Institutional Animal Care and Use Committee. To prepare TK-NOG mice for transplantation, 8-10 week old TK-NOG mice were treated (i.p.) with 25 mg/kg ganciclovir (GCV) on day −7 and −5 prior to transplantation. Then, a 20 µl blood sample was collected 6 days after the 1st GCV treatment, diluted 1:3 into water, and 10 µl of the diluted sample was used to measure the serum ALT level using a Fuji dry-chem 7000 instrument as described (Hasegawa et al, Biochem Biophys Res Commun. 2011 Feb. 18; 405(3): 405-10, which is hereby incorporated by reference in its entirety). Only mice with an ALT level >200 U/L were used for cellular transplantation on day 7. Mice with ALT levels <200 U/L were treated with an additional dose of 25 mg/kg GCV on day 7, the ALT level was re-examined on day 13, only mice whose repeat ALT level was >200 U/L were used for cell transplantation on day 14.

Ultrasound-guided liver injection. Transplanted cells were directly placed into a liver lobe under ultrasound-guided injection using a small animal ultrasound system Vevo 2100 (Visualsonics Canada). Brightness mode (B-mode) was used to acquire two-dimensional images for an area of interest with MS550s transducer. The mice were placed under 1.5% isofluorane anesthesia during this procedure using a single animal vaporizer unit (EZ-Systems Corp, EZ-108SA). Then, $5 \times 10^6$ cells were suspended in 200 µl of William's E medium (Invitrogen, A12176-01), which was injected into 10 distinct sites in the liver using a 30G needle.

Analysis of tumor formation. To assess tumor formation, $5 \times 10^4$ Chi-Hep, SCi-Hep or iPS-Hep were harvested and mixed with 50 µl of matrigel (BD Biosciences, Cat: 354277). NOG mice were anesthetized using 1.5% isoflurane using individual vaporizer unit (EZ-Systems Corp, EZ-108SA). An incision was made, and a slight pressure to both sides of the incision was applied to expose the kidney. The cells were then injected under the kidney capsule using a syringe with a 27-gauge needle. After slowly delivering the cells, a dry swab was placed over the injection site to prevent leakage. During the procedure, the kidney was kept moist by application of saline with a cotton-tipped swab. After three to 8 weeks, the mice were sacrificed and the injected kidney was harvested for histological analysis.

Results

Example 1

Production of Hepatocyte-Like Cells from Adipocyte-Derived Stem Cells

Figure 1B:
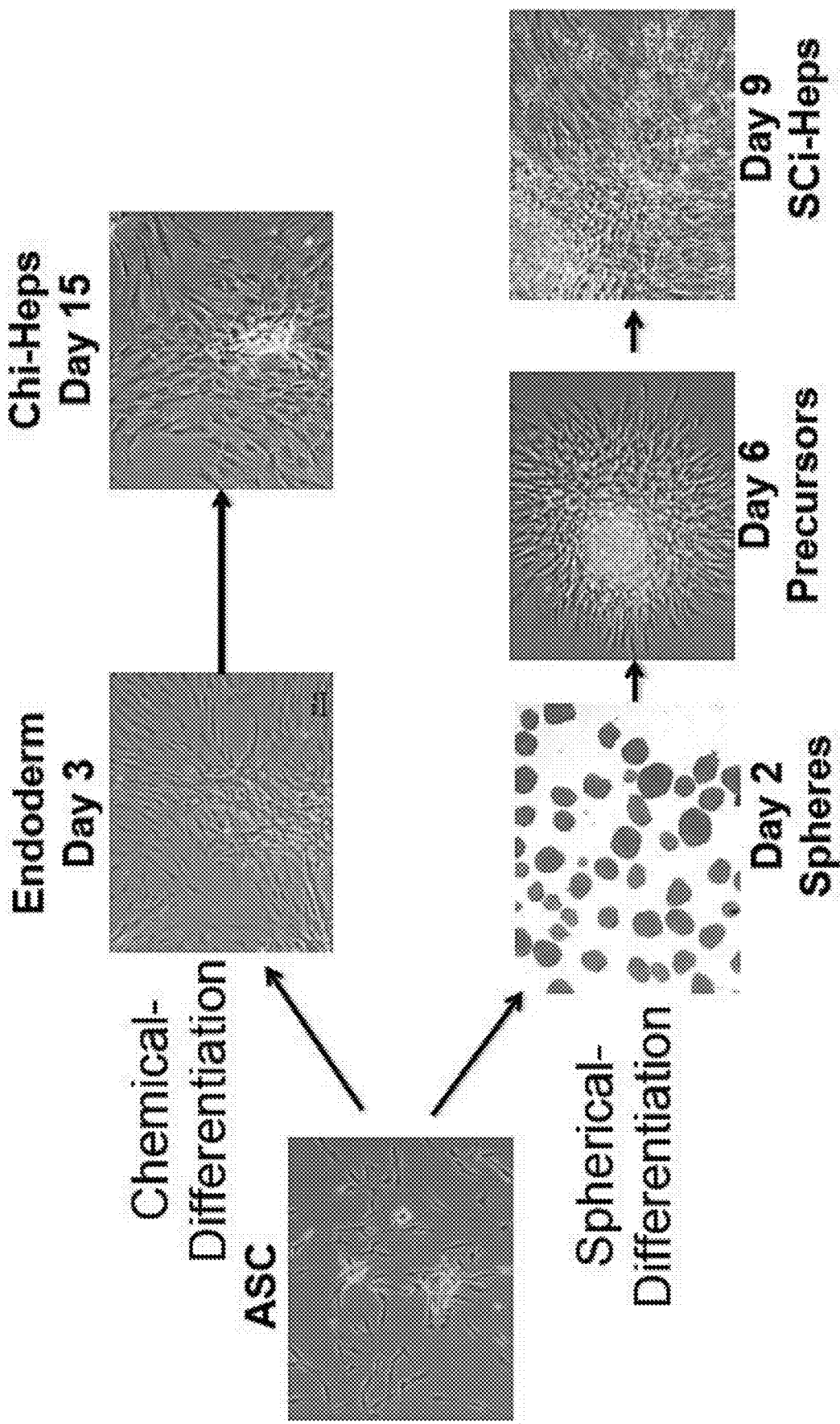
Figure 1C:
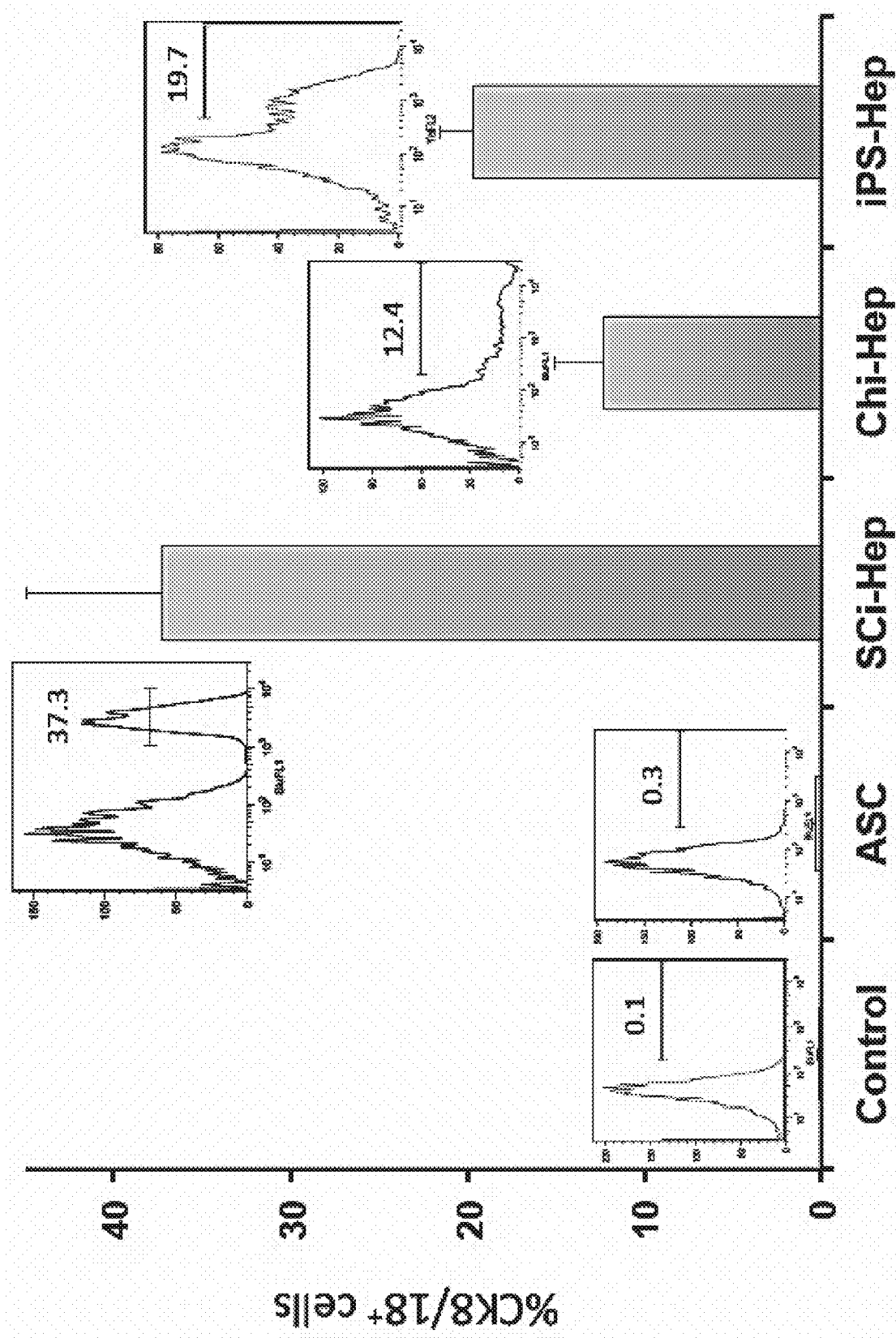
Figure 1D:
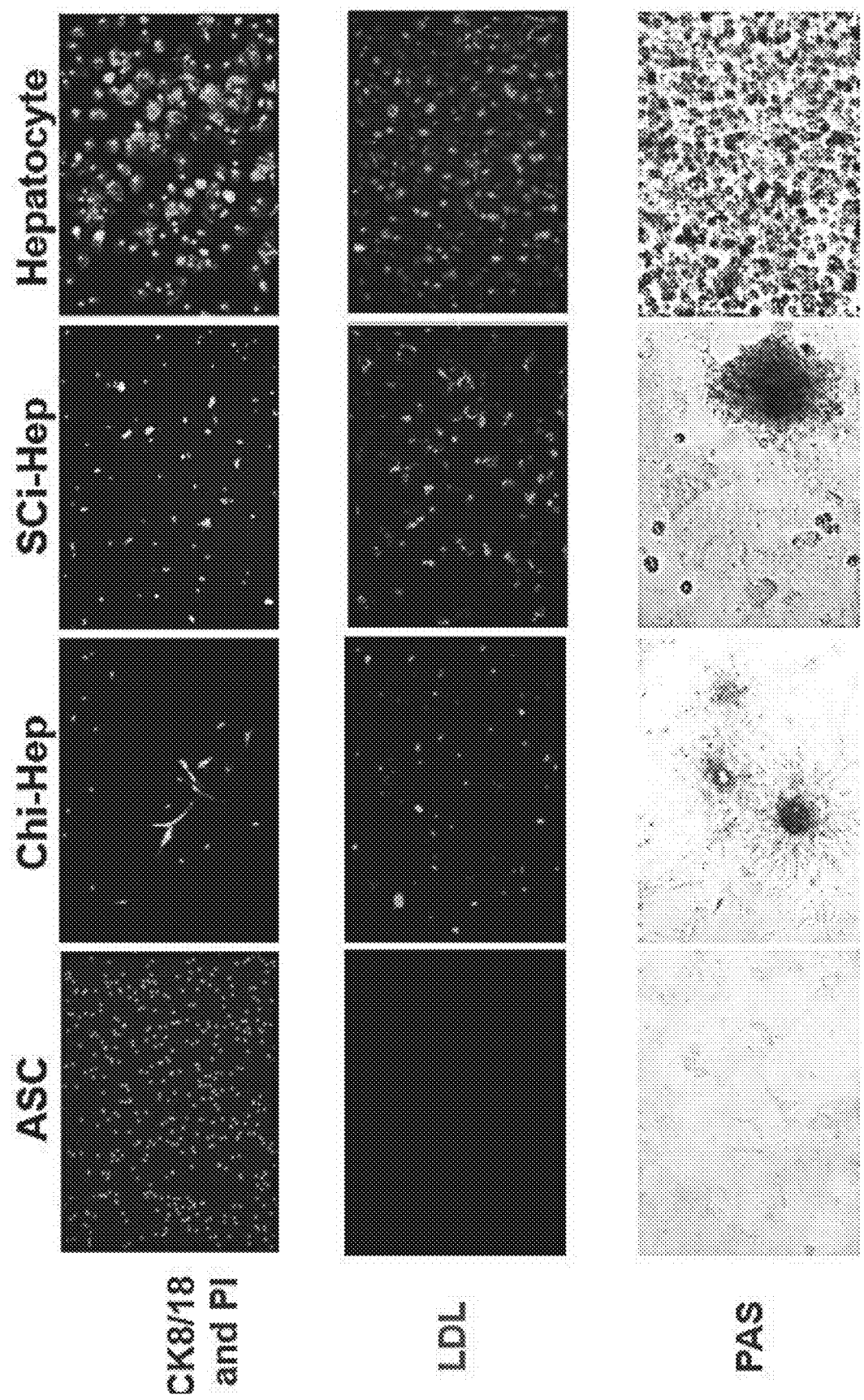
Figure 1E:
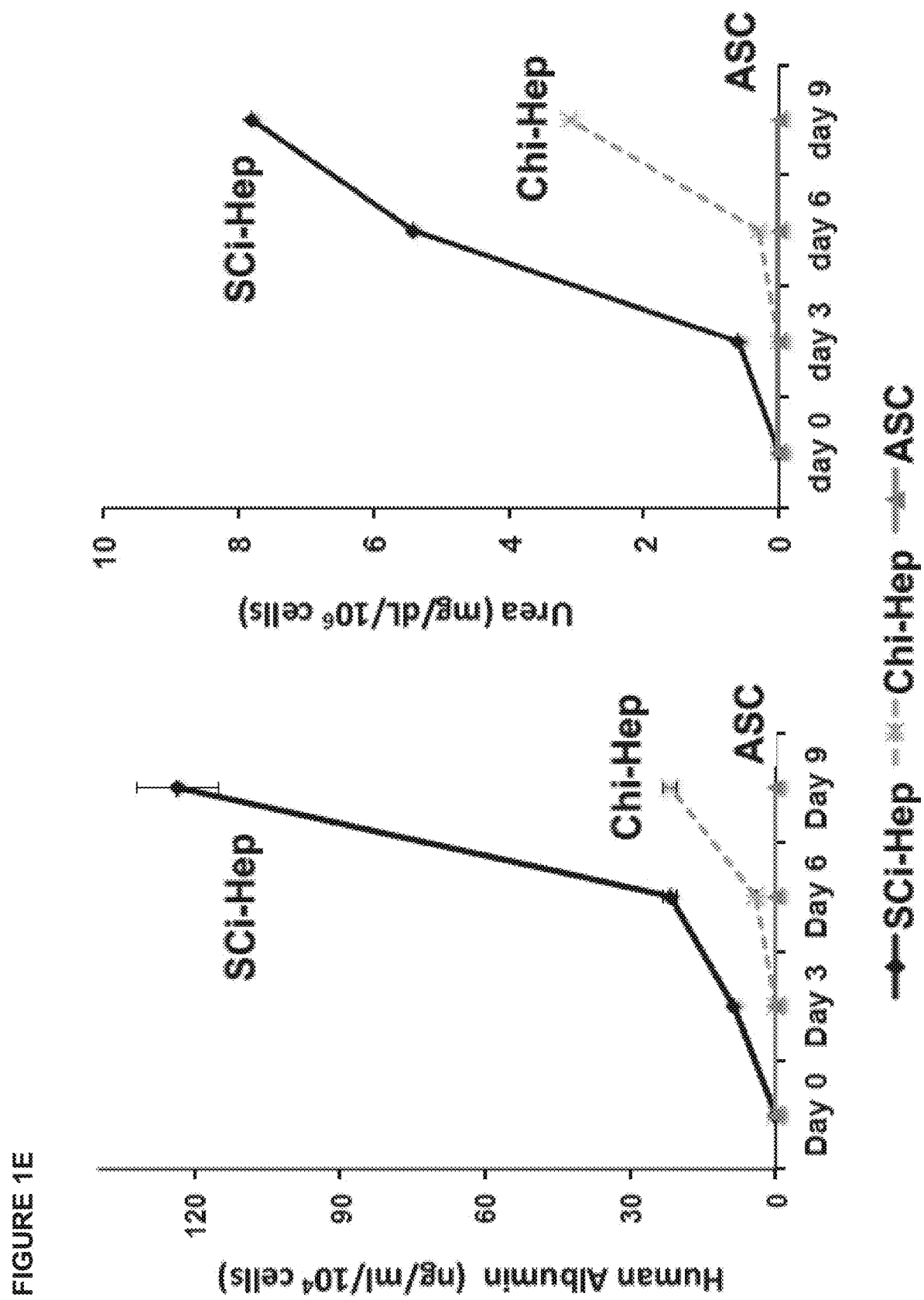
Figure 2A:
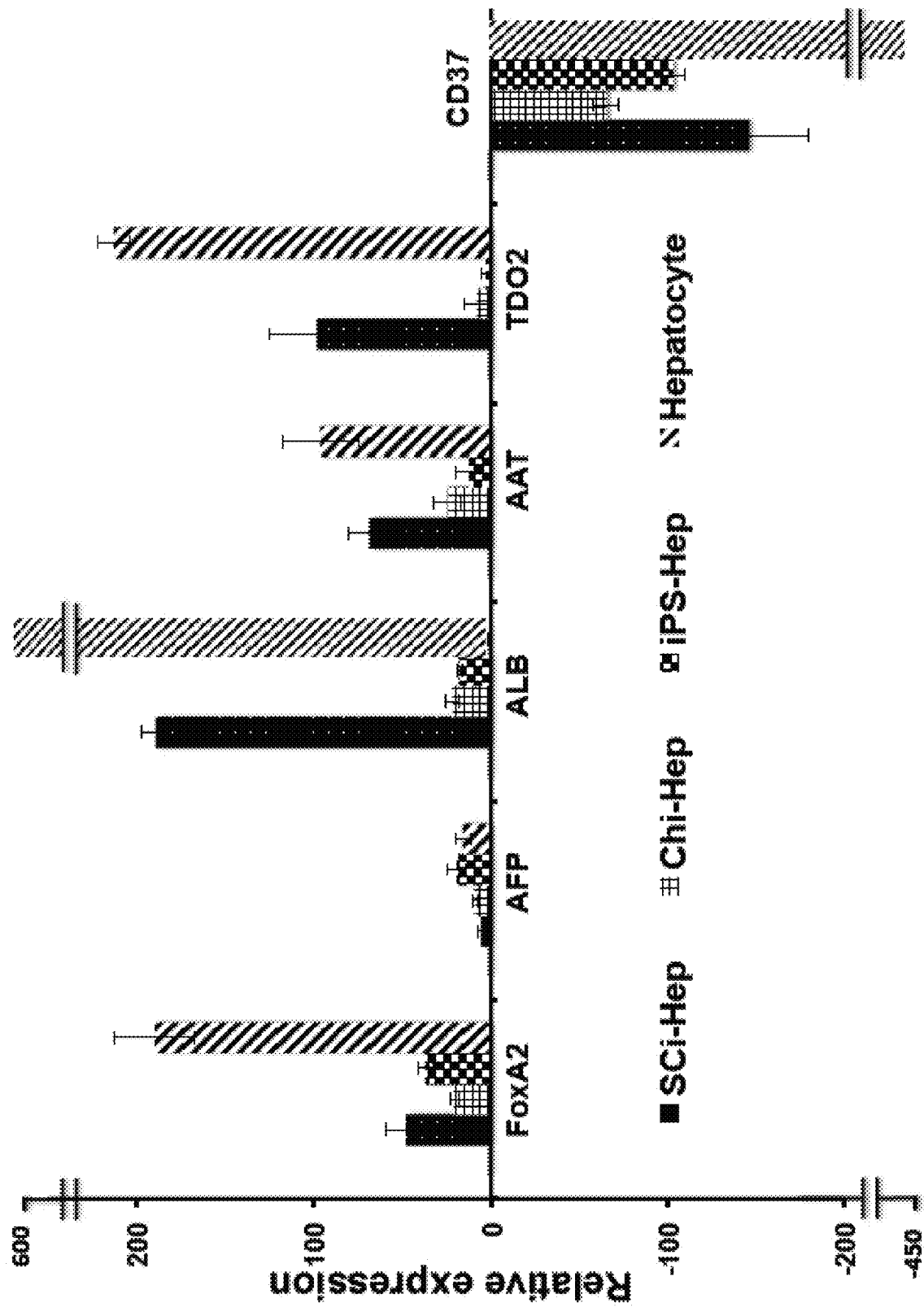
FIGS. 2A-2C depict gene expression in Chi-Heps, SCi-Heps and adipocytes.
Figure 5A:
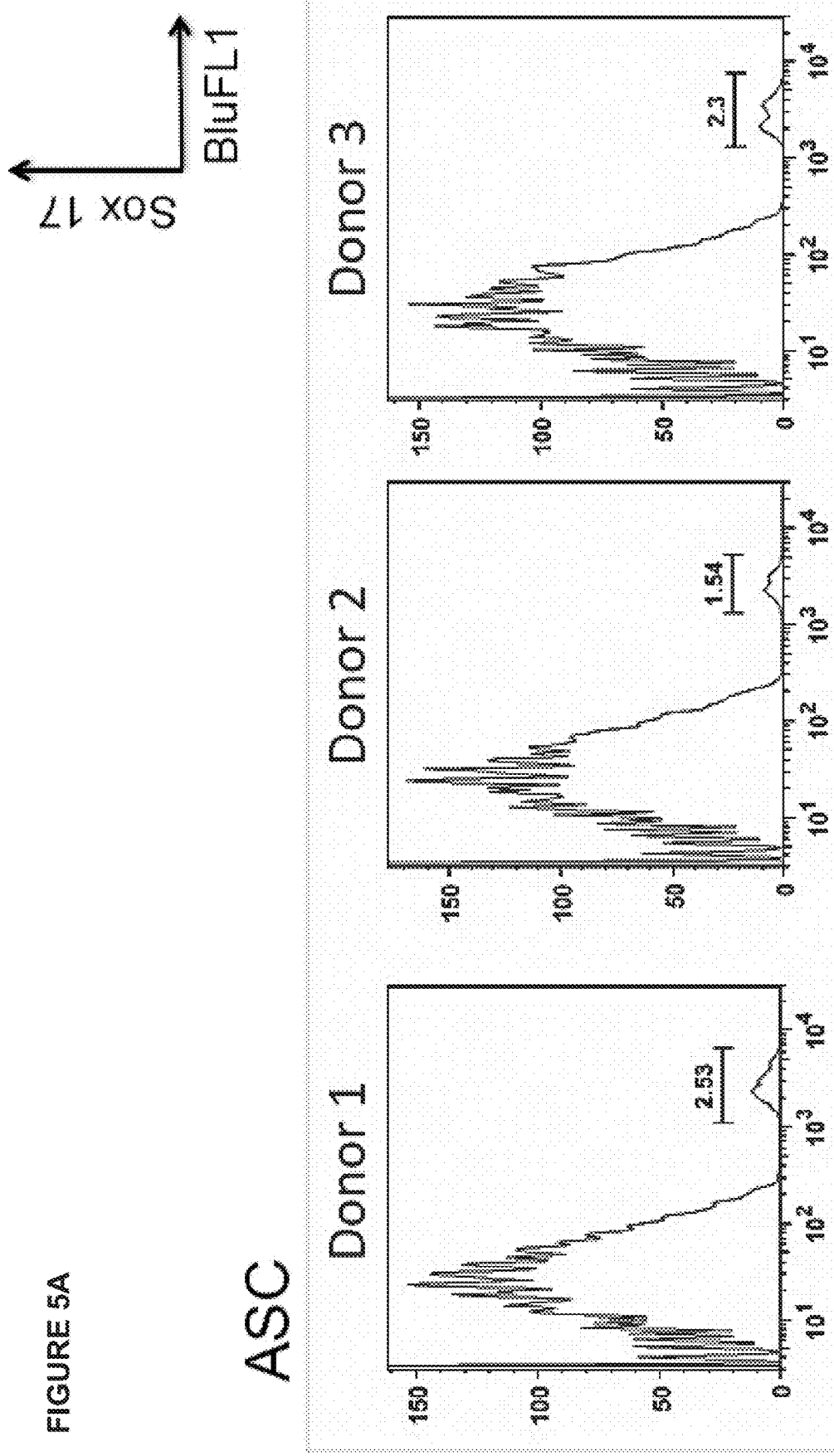
FIGS. 5A-5C provide FACS analysis performed using an anti-Sox 17 antibody, which recognizes to a marker for endodermal cells. ASC were isolated from three different donors and induced to differentiate using the standard (Chi-Hep) or spherical culture (SCi-Heps) methods. After 4 days of differentiation, FACS was performed using an anti-Sox 17 antibody, which recognizes to a marker for endodermal cells. The percentage of ASC differentiating into endodermal cells after spherical culture (61.2±2.4) more than doubled that obtained using the standard method (25.7±1.3).
Figure 5B:
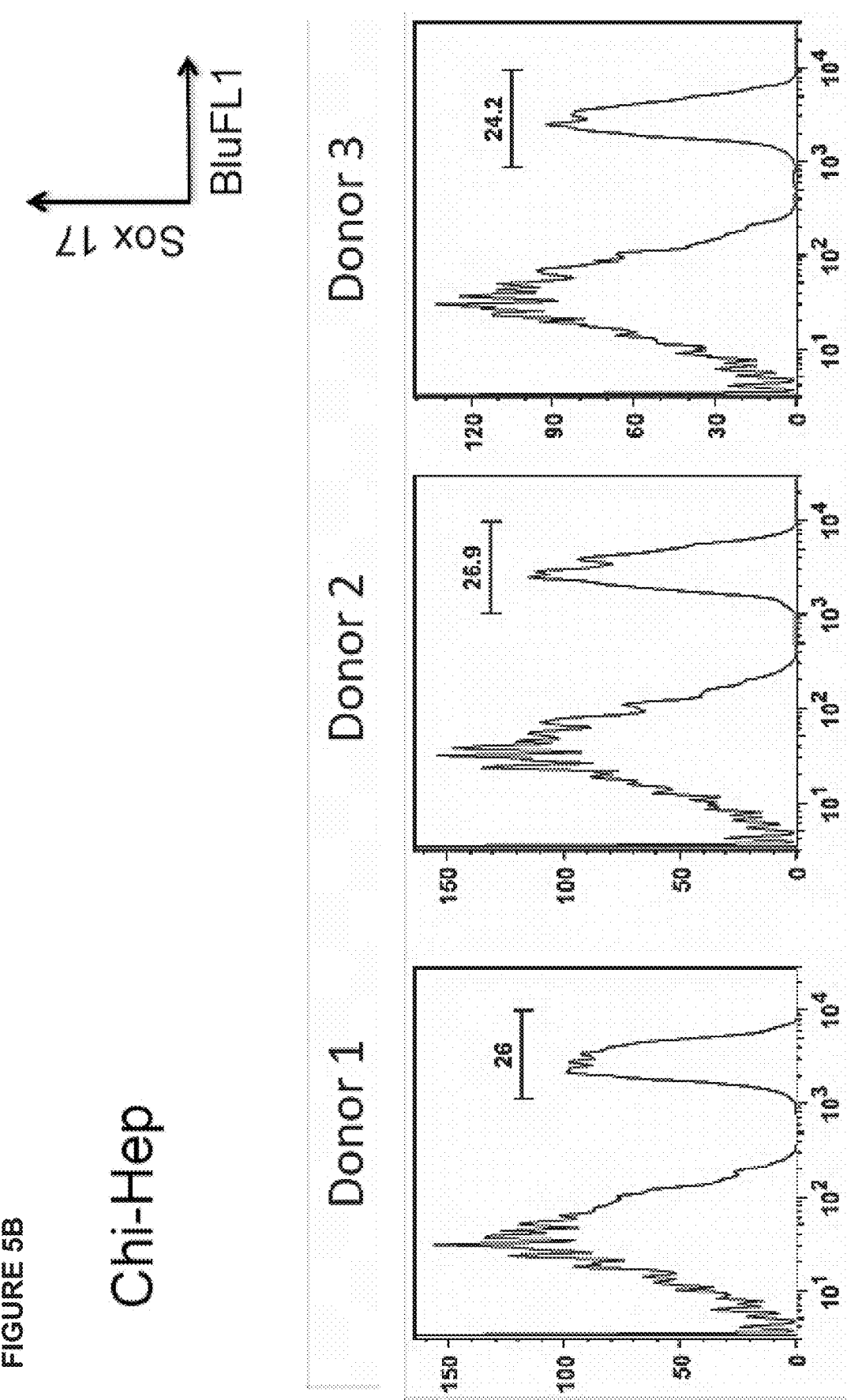
Figure 5C:
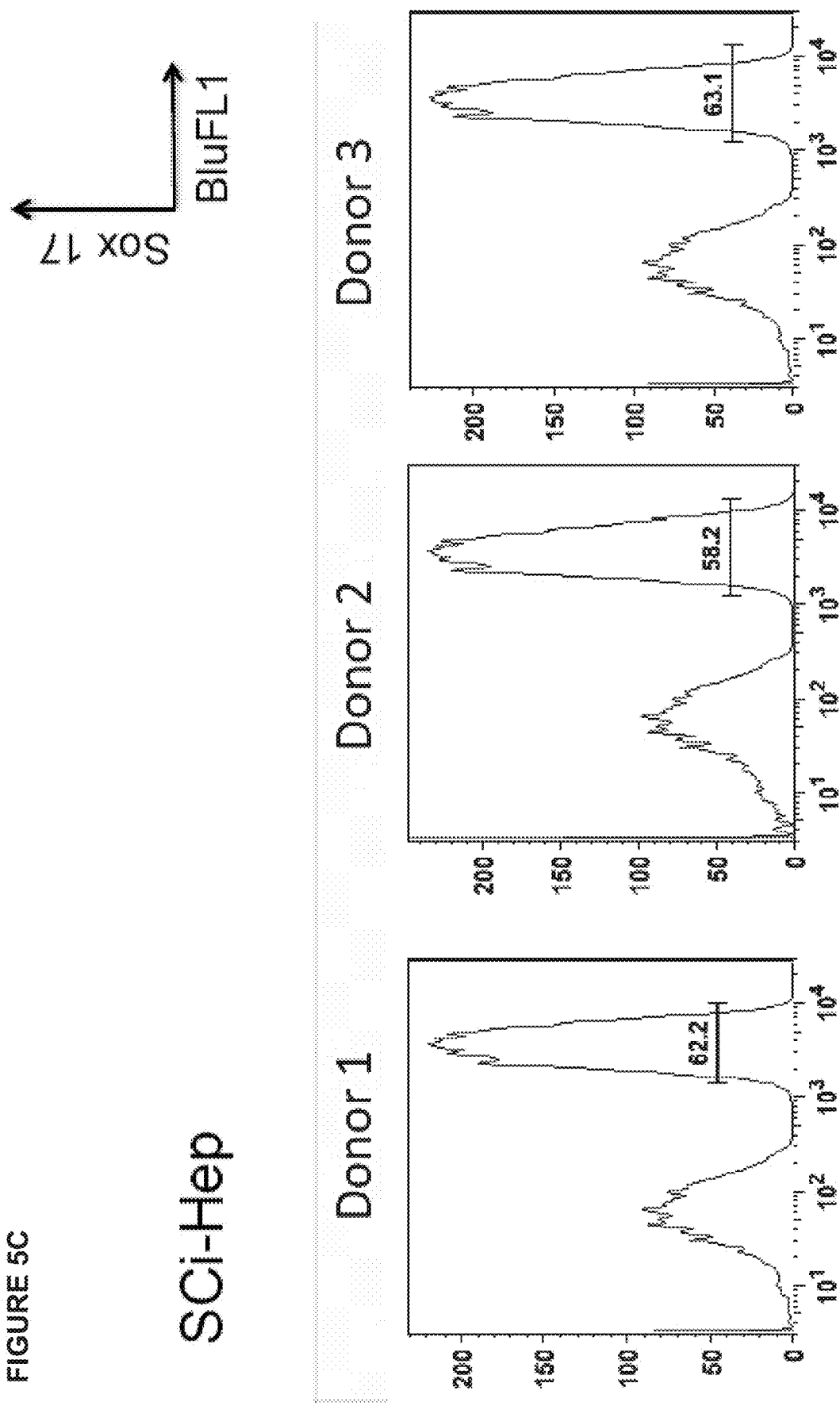
Figure 6A:
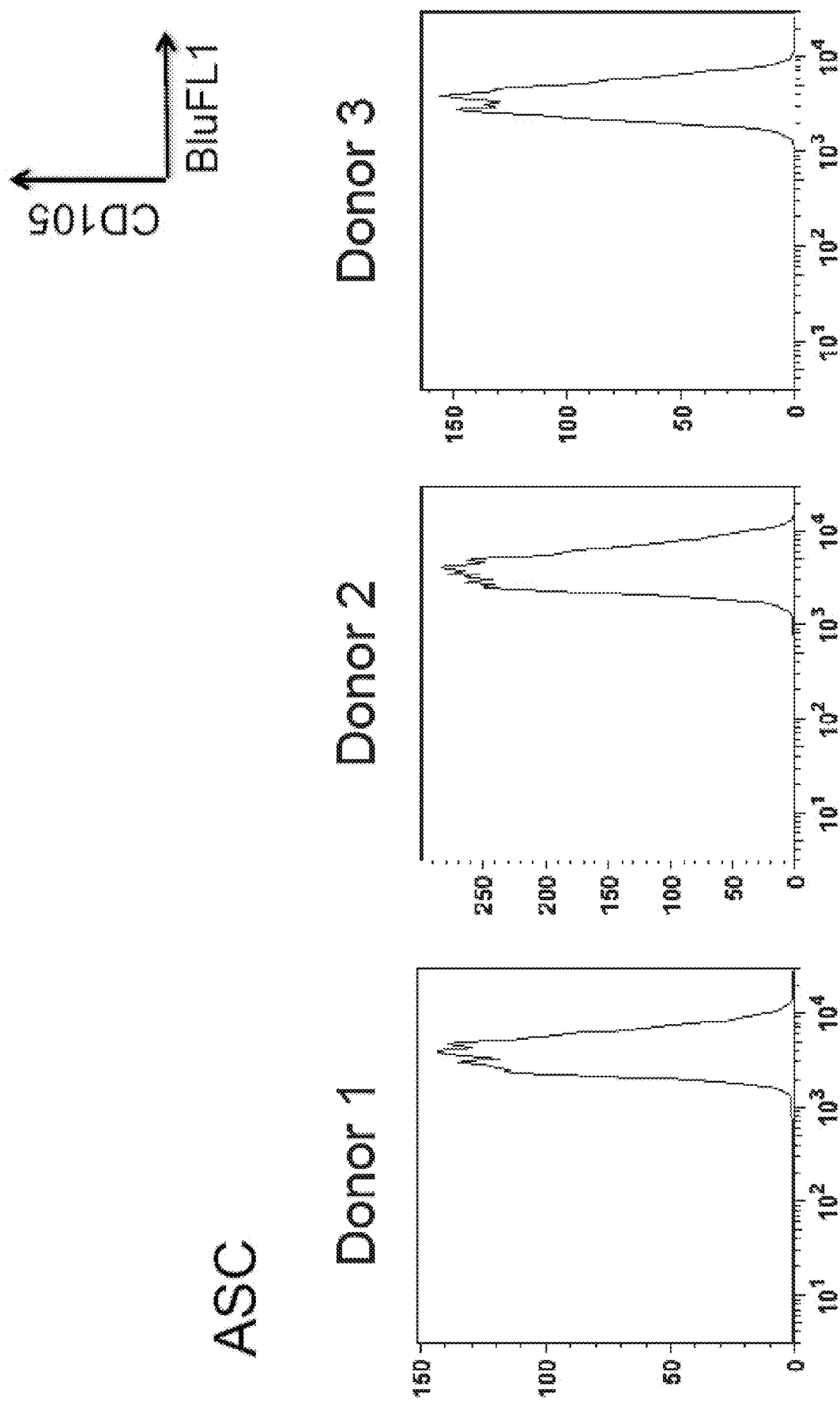
FIGS. 6A-6B provides FACS analysis performed using an anti-CD105 antibody, which binds to a marker for ASC. ASC were isolated from three different donors and induced to differentiate into SCi-Heps using the spherical culture method. After 9 days of differentiation, FACS was performed using an anti-CD105 antibody, which binds to a marker for ASC. While 98.6±0.5% of ASC expressed CD105, the percentage of SCi-Heps expressing this ASC marker was only 9.0±0.5%.
Figure 6B:
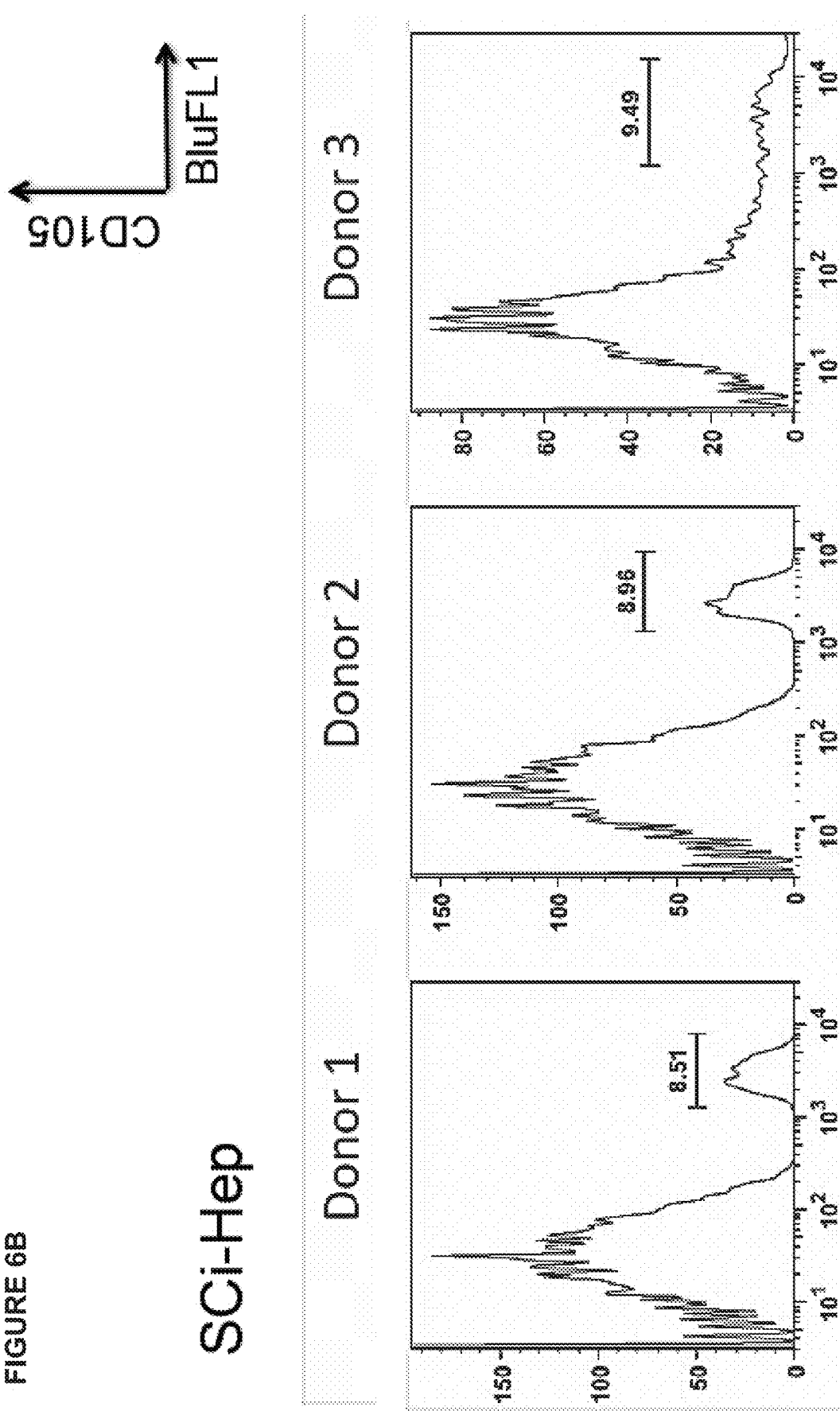

Provided is a method for differentiating adipocyte-derived stem cells (ASCs) into hepatocyte-like cells (iHeps) (FIG. 1A). ASCs are first cultured using the 'hanging drop' method to produce spherical cellular aggregates (spheres') (FIG. 1B). As shown by analysis of SRY-related HMGbox transcription factor 17 (Sox17) expression, spherical culture doubles the number of ASCs in a lipo-aspirate that differentiate into endodermal precursor cells (FIG. 5). Since the ability of mesenchymal-derived ASCs to differentiate into endoderm may be rate limiting for hepatocyte generation, wnt3a was added to the (stage 1) differentiation medium. Relative to a previous described method of generating iHeps (Banas et al., J Gastroenterol Hepatol. 2009 Jan.; 24(1):70-7), the subject method produces a 2.3-fold increase in the number of ASCs obtained from a lipo-aspirate and a 3-fold increase in the efficiency (% of hepatocyte-like cells obtained, as assayed using the CK8/18 marker) after the 2-stage differentiation process is completed (FIG. 1C and Table 1). This method increases the number of iHeps obtained from a liter of lipo-aspirate by 7-fold and reduces the period of in vitro culture required to obtain biochemically defined hepatocytes at >37% purity to 9 days or less. Like Chi-Heps, the cells produced by spheroid culture, which we refer to as SCi-Heps, developed a hepatocyte-like morphology (FIG. 1B), and exhibited many properties of mature hepatocytes. They expressed proteins (CK8/18) that are found on hepatocytes (FIG. 1C), and had multiple metabolic properties of hepatocytes, including: LDL endocytosis, glycogen synthesis (FIG. 1D), albumin secretion, and urea production (FIG. 1E). Moreover, SCi-Heps expressed multiple hepatocyte specific mRNAs, and had markedly reduced levels of expression of multiple adipocyte-specific mRNAs (FIG. 2A), along with reduced expression of an ASC-specific cell surface protein (CD105) (FIG. 6; FIG. 12).

Table 1. ASCs prepared from 3 different donors were induced to differentiate into Chi-Heps using a previous method (Banas et al., J Gastroenterol Hepatol. 2009 Jan.; 24(1):70-7) or into SCi-Heps (Spherical Culture iHeps) using the subject method. The number of ASCs obtained after 3 days (±SEM), the percentage of cells (±SEM) expressing a hepatocyte marker (CK8/18+) after differentiation for 12 (Chi-Hep) or 9 (SCi-Hep) days, the number of days required to complete the hepatocyte differentiation process and the estimated number of iHeps obtained per liter of lipo-aspirate are shown.

TABLE 1

| Method | Day 3 Cell # | % CK8/18+ | Days of Differentiation | Days Total | Estimated Cells/Liter |
|---|---|---|---|---|---|
| Chi-Hep | $(2.7 \pm 0.3) \times 10^4$ | $12.3 \pm 2.8$ | 12 | 18-30 | $3.3 \times 10^8$ |
| SCi-Hep | $(6.1 \pm 0.2) \times 10^4$ | $37.7 \pm 7.7$ | 9 | 12 | $2.3 \times 10^9$ |

Figure 2B:
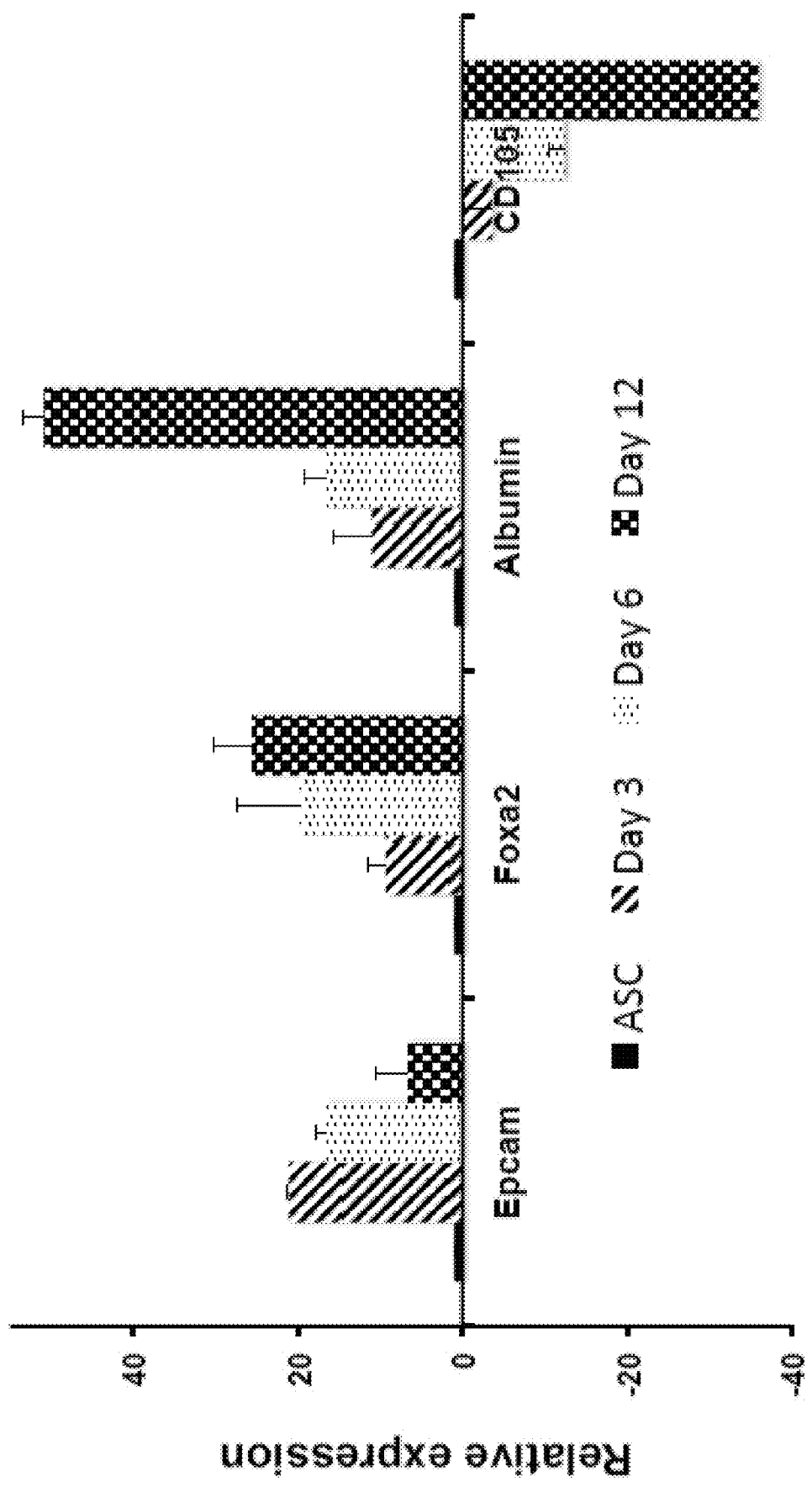
Figure 7:
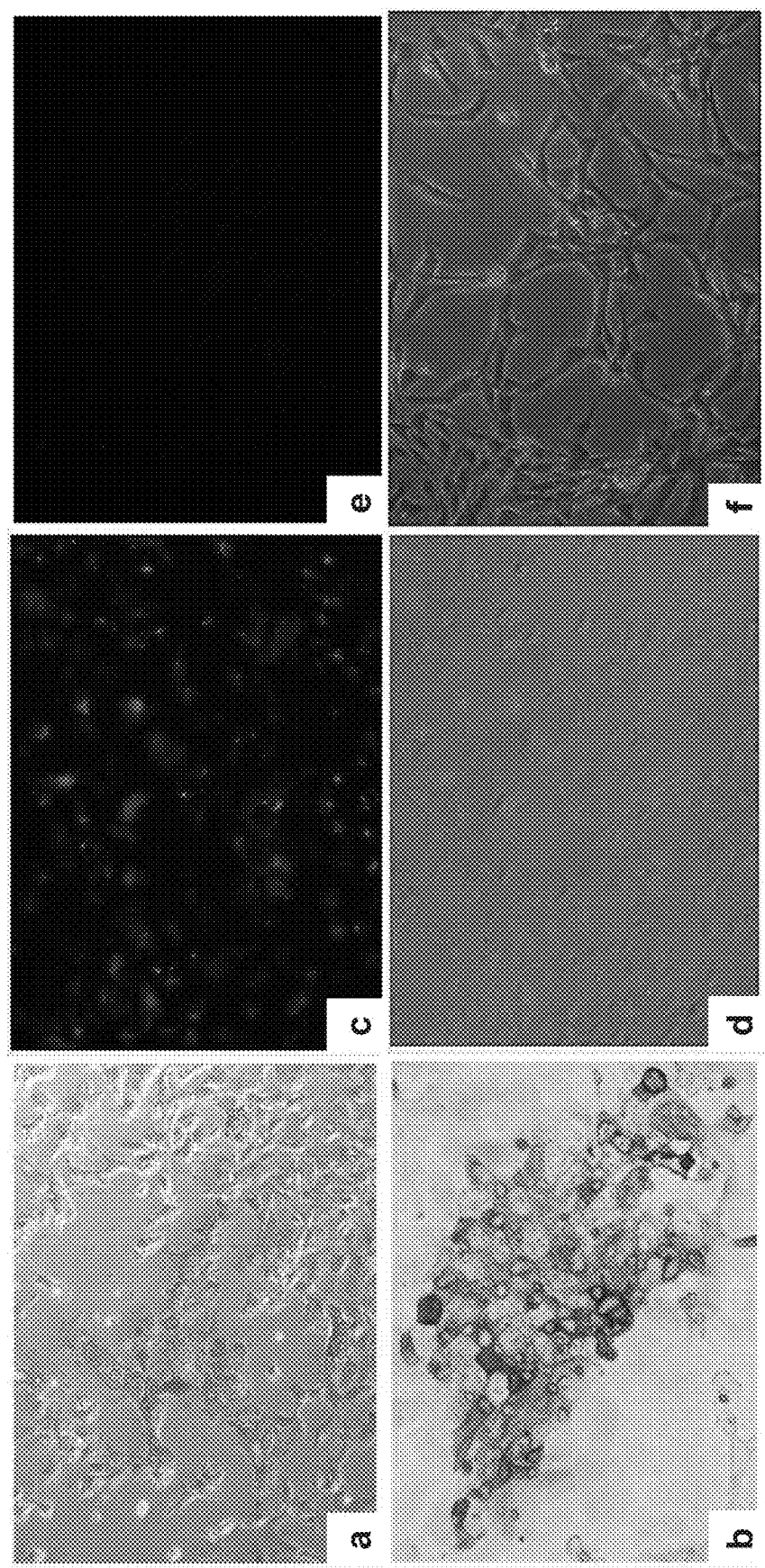
FIG. 7 demonstrates that iPS-Heps can synthesize glycogen (a,b) and endocytose low-density lipoproteins (LDL) (c,d). The LDL immunofluorescence and PAS stained images are shown at 100× (a, c) and 400× magnification (b, d). In contrast, ASC could not endocytose LDL (e, 100×), nor did they stain with PAS (f, 100×).
Figure 8A:
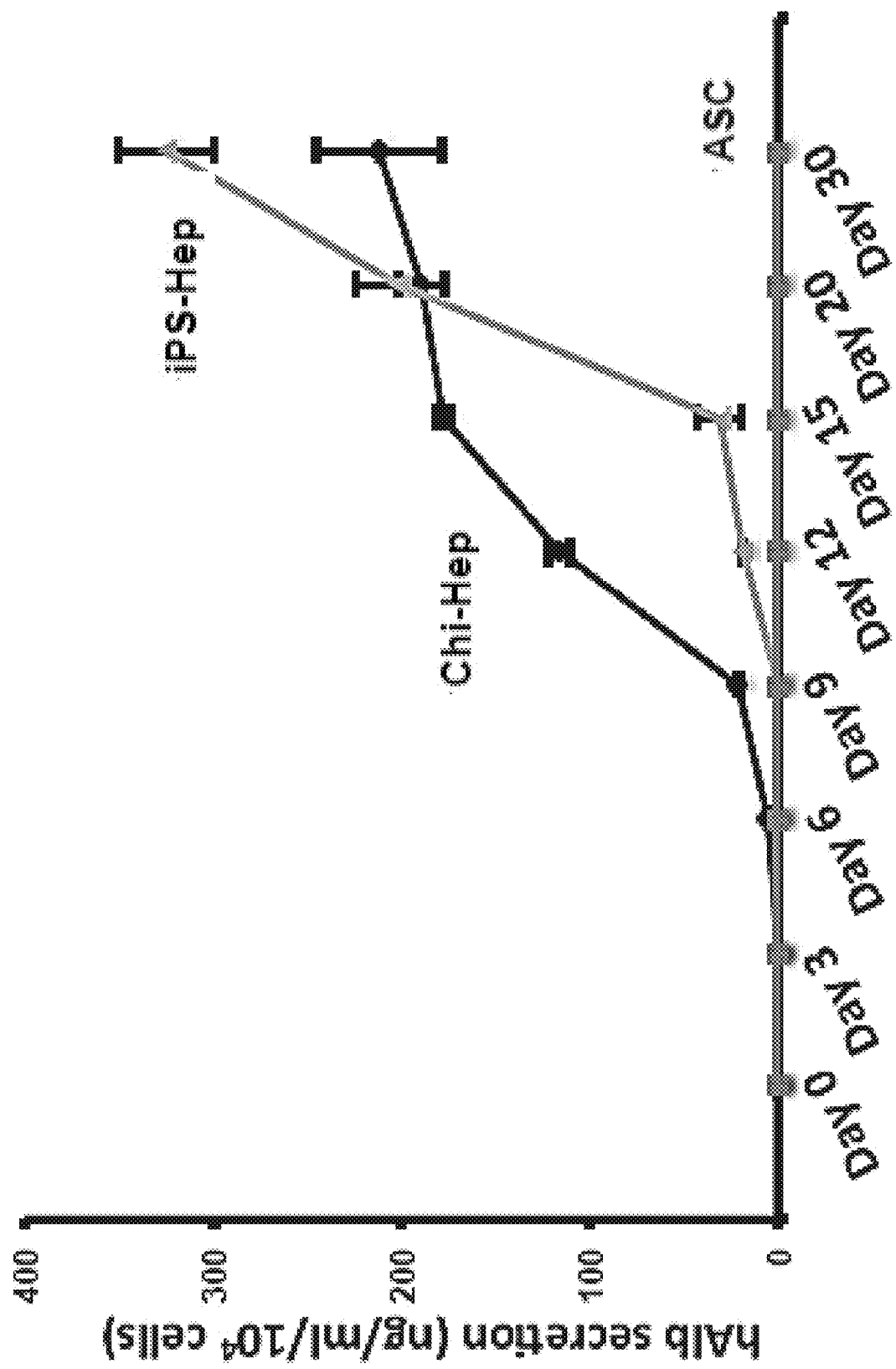
FIGS. 8A-8D demonstrate that iPS-Heps have hepatocyte properties. The amount of human albumin (FIG. 8A) or urea nitrogen (FIG. 8B) secreted into the supernatant by Chi-Heps, iPS-Heps and ASCs are shown at the indicated time points. Chi-Heps produced albumin and urea well before iPS-Heps produced detectable amounts of these analytes, while control ASCs did not produce albumin or urea.
Figure 8B:
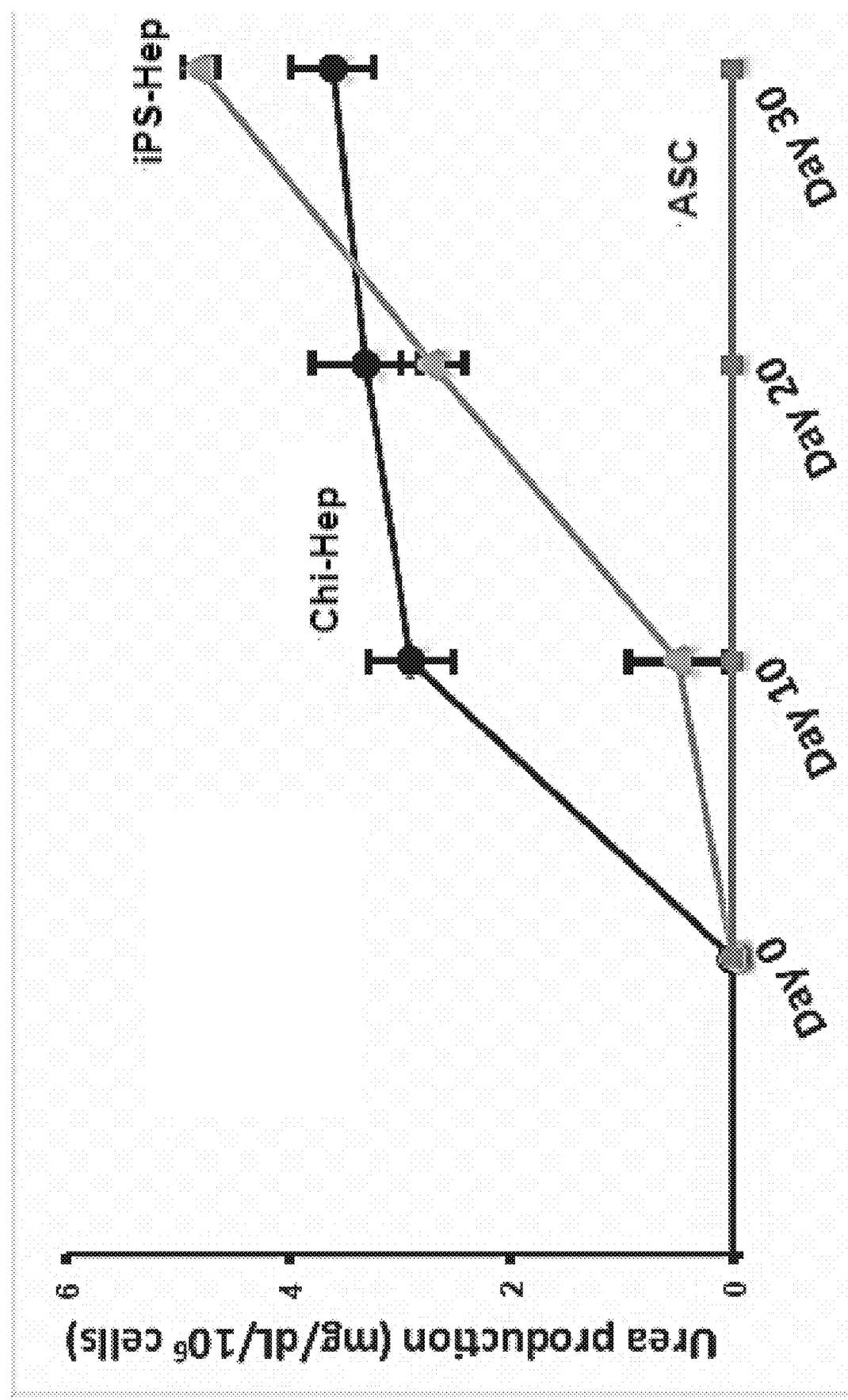
Figure 8C:
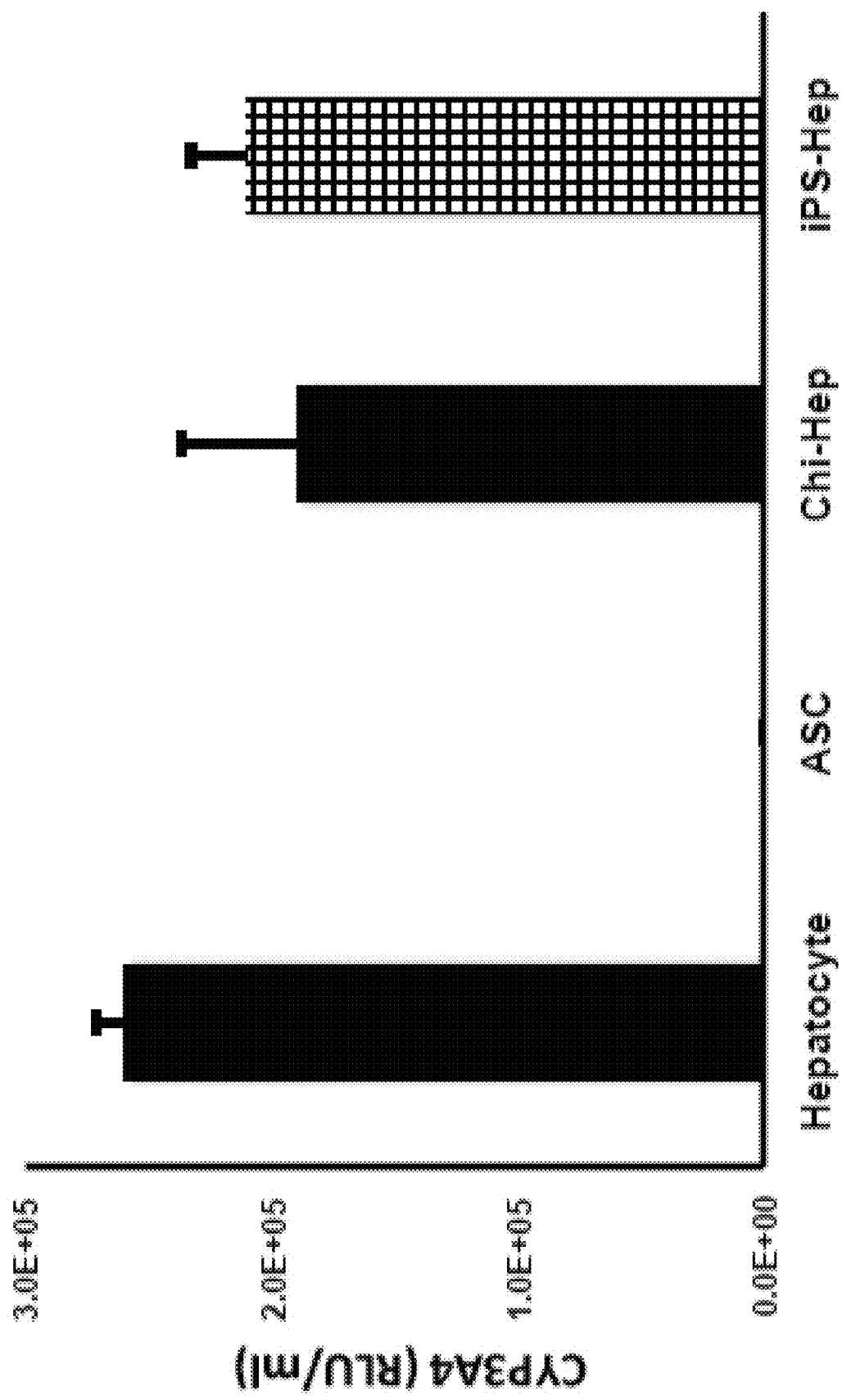
Figure 8D:
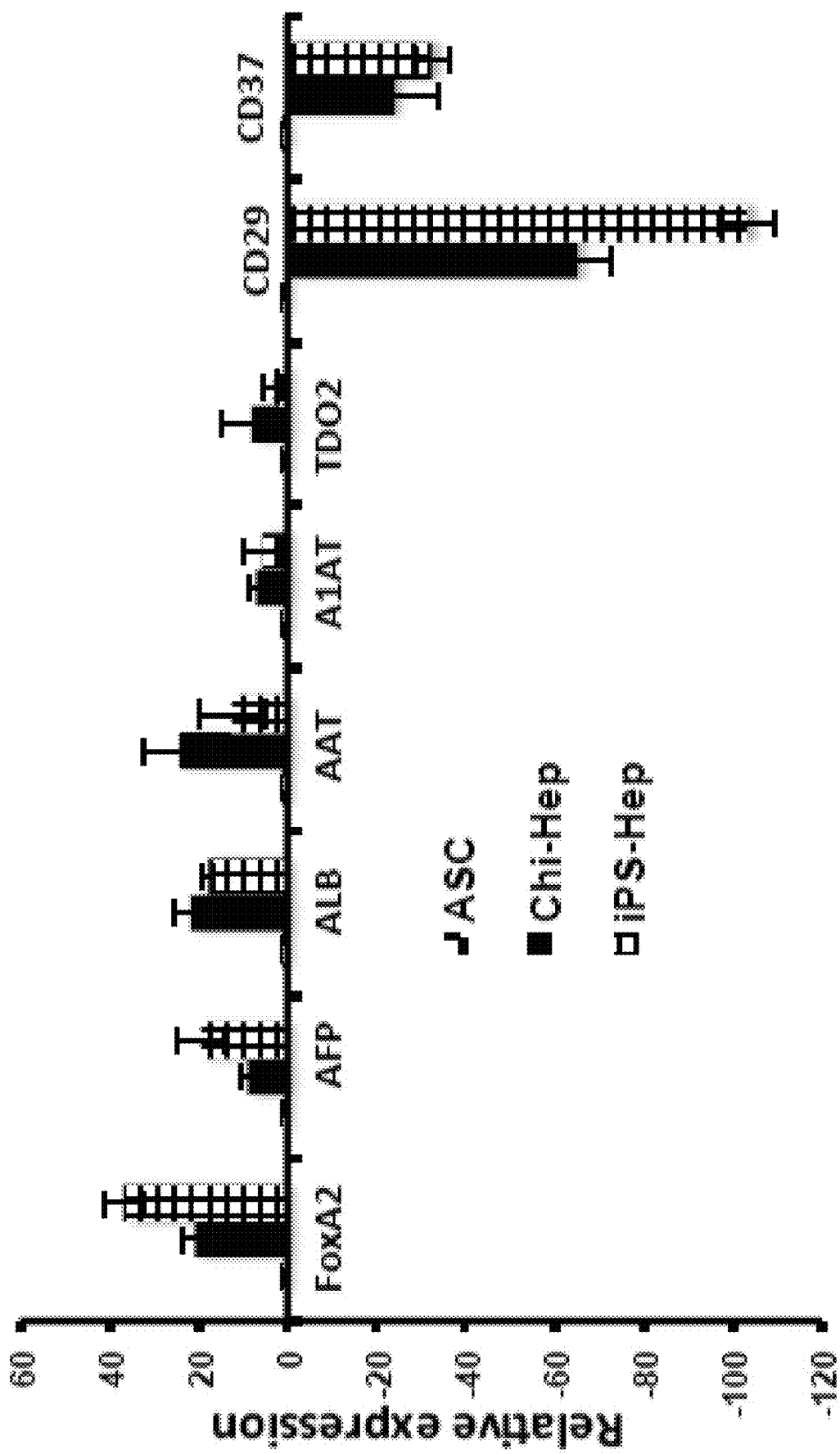

We also compared the properties of Chi- and SCi-Heps with iPS-Heps, which are ASCs (obtained from the same donor) that were re-programed into iPS cells after transfection of four genes (Oct4, Sox2, Klf4 and c-Myc), and then induced to differentiate into hepatocytes using the Ochiya protocol (Banas et al., J Gastroenterol Hepatol. 2009 Jan.; 24(1):70-7). The iPS-Heps expressed a protein (CK8/18) found on hepatocytes (FIG. 1C); could endocytose LDL, synthesize glycogen (FIG. 7) secrete albumin, produce urea, and had CYP450 activity (FIG. 8). Of importance, SCi-Heps produced albumin and urea after only 3 days of in vitro differentiation, which was 3-6 days before Chi-Heps (FIG. 1E) and 12 days before iPS-Heps (FIG. 8) produced these analytes. ASCs must first be reprogramed into and then exit from the pluripotent state before they can differentiate into iPSHeps. In contrast, SCi-Heps are produced by direct differentiation of ASCs into endoderm, which explains why they can more quickly produce these analytes. Consistent with the more rapid differentiation process, SCi-Heps expressed mRNAs for endodermal (epithelial cell adhesion molecule, Epcam) and hepatocyte-specific (Albumin, Foxa2) genes within 3 days after initiation of hepatic differentiation (FIG. 2B). Also, SCi-Heps had the highest level of albumin production (on a per cell basis) among the 3 types of ASC-derived cells tested. Their increased level of albumin production is consistent with the FACS results indicating that 37% of SCi-Heps expressed a mature hepatocyte marker, while only ~12% and 20% of Chi-Heps and iPS-Heps, respectively, expressed this marker (FIG. 1C). Thus, the SCi-Heps method produces an increased number of hepatocyte like cells from a lipoaspirate, and the cells are prepared within a timeframe that makes it possible that they could be used in an acute clinical situation, such as would occur after an overdose of acetaminophen.

Figure 2C:
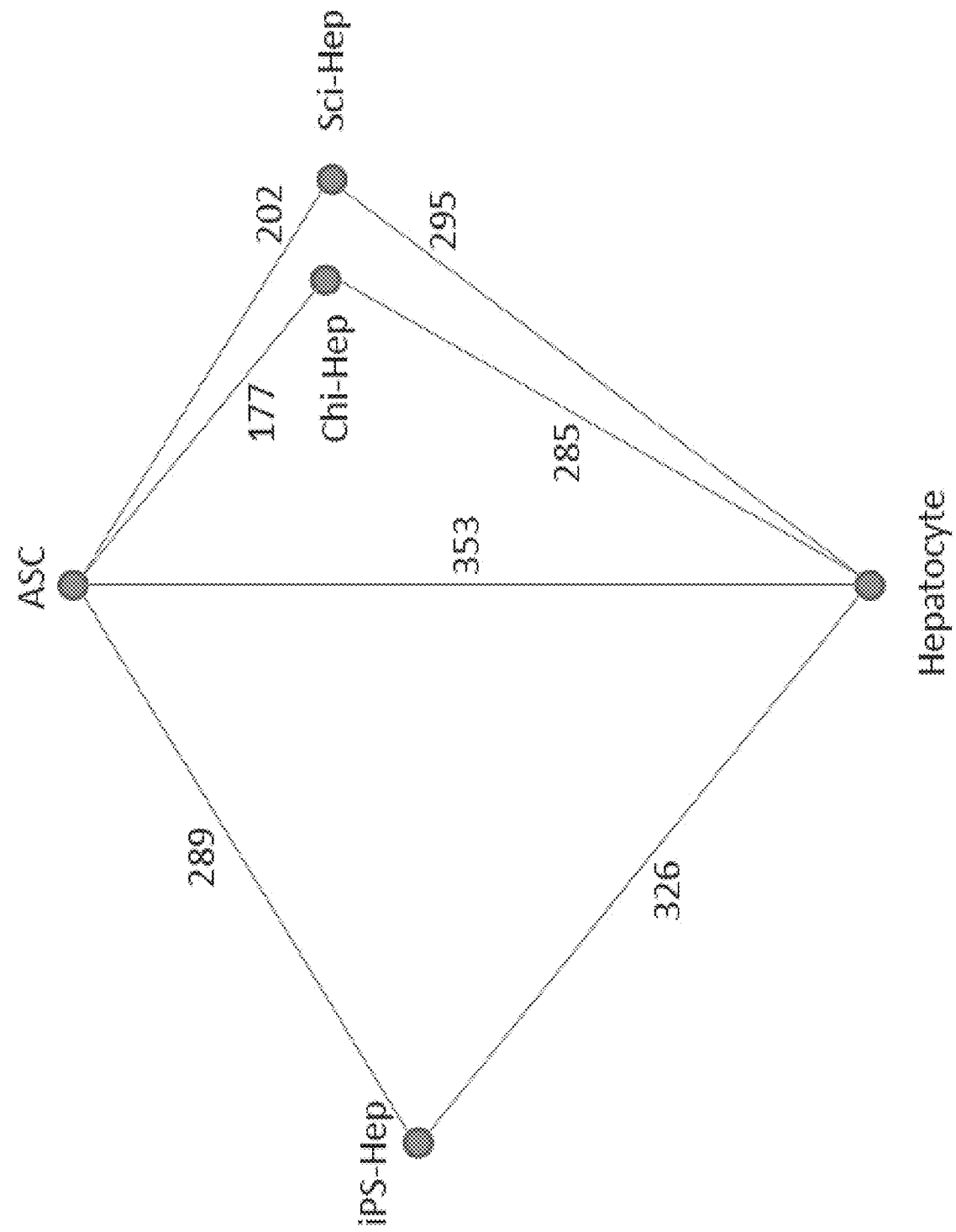
Figure 9:
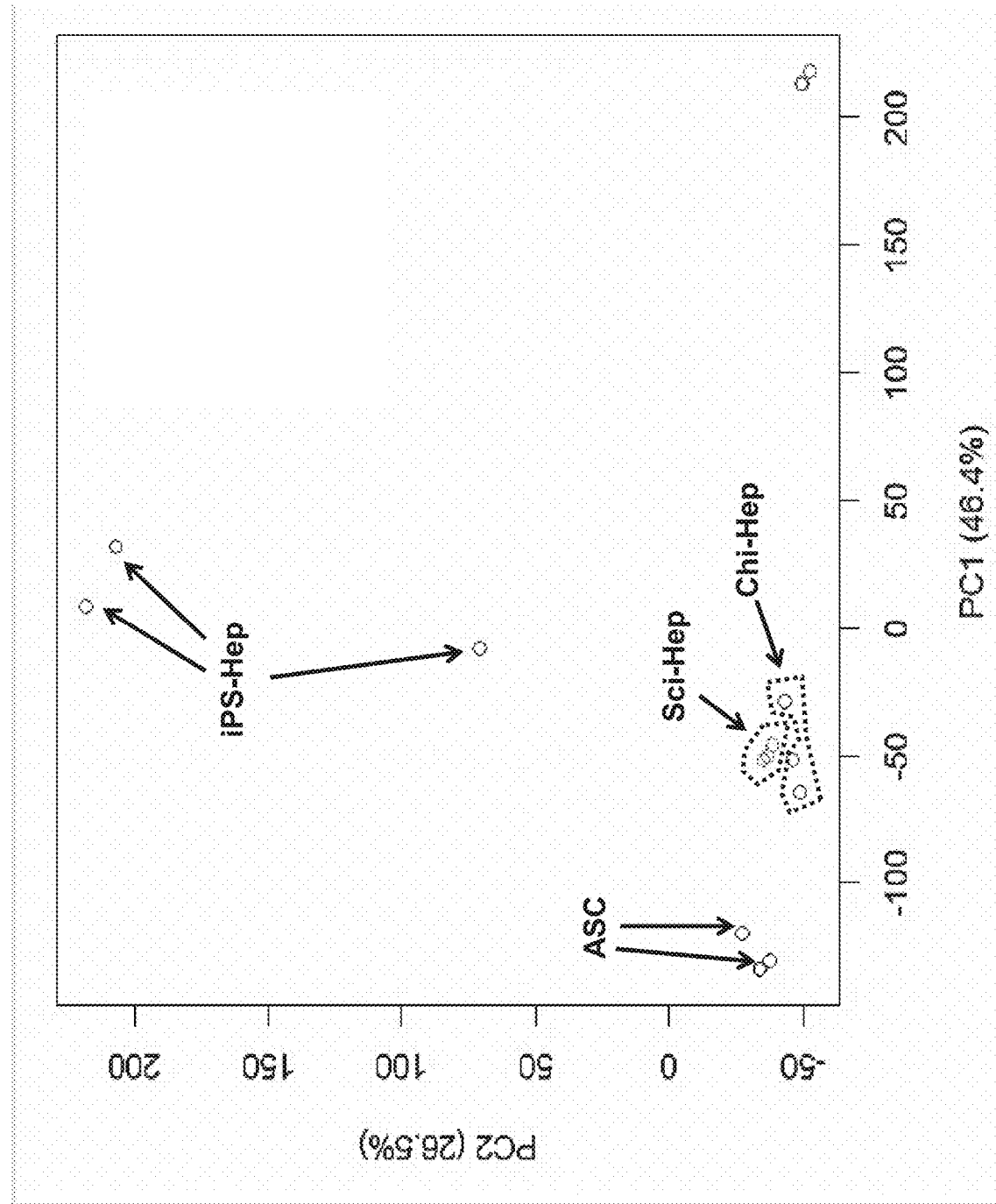
FIG. 9 provides principal component analysis for the gene expression data obtained from ASC, Chi-Hep, SCi-Hep, iPS-Hep and hepatocytes. The first (x-axis) and the second (y-axis) principle components (PC) explained 46.4% and 26.5%, respectively, of the total variance in the expression profile. Of note, iPS-Heps had a large amount of deviation along PC2 relative to ASCs and hepatocytes, while Chi-Heps and SCi-heps were right in between the ASCs and hepatocytes. Consistent with other analyses (including the analysis shown in FIG. 2C), this graph indicates that iPS-Heps had a large number of gene expression changes that were not present in hepatocytes (relative to ASCs).

To further characterize these cells, gene expression profiling was performed in ASCs, Chi-Heps, SCi-Heps, iPS-Heps and hepatocytes using microarrays, and the data analysis is described in the supplemental information. In brief, multiple comparisons indicated that in vitro differentiation significantly altered the gene expression pattern in ASCs, and that Chi- and SCi-Heps expressed a very large number of hepatocyte-specific genes (e.g., as published in Table S2 in Xu et al., Cell Transplantation, 2013 Oct. 21; DOI: 10.3727/096368913X673432; "Enabling Autologous Human Liver Regeneration With Differentiated Adipocyte Stem Cells"; the entirety of which, including figures, tables, supplementary figures, supplementary tables, etc., is hereby incorporated by reference). Moreover, two analyses (a space diagram of the gene expression differences (FIG. 2C) and principal component analysis (FIG. 9)) indicate that the Chi- and SCi-Heps had a gene expression profile that was closer to that of hepatocytes than the iPS-Hep profile. iPS-Heps expressed a larger number of genes that were not expressed in adipocytes or hepatocytes (FIG. 11). In summary, SCi-Heps have a gene expression pattern that resembles, but it does not fully mirror, that of hepatocytes. Since only 37% of the Sci-Hep cells expressed a mature hepatocyte marker (FIG. 1C), it is possible that the gene expression pattern in fully differentiated SCi-Heps could more closely resemble that of hepatocytes than is suggested by this analysis, since some of the gene expression changes could be masked (diluted) by the preponderance of less differentiated cells in the population. Although SCi-Heps were produced by a different method and were cultured for a much shorter time period than were Chi-Heps, their gene expression profiles were extremely similar: 48165 of 49395 probes did not show a significant expression difference (adjusted p-value>0.01 or fold-change <2) between these two types of iHeps. The level of expression of 306 genes (0.6%) had a >3-fold (adjusted p<0.01) and only 44 genes (0.08%) had a >10-fold (adjusted p<0.01) difference in expression in these two cell types (e.g., as published in Table S4 in Xu et al., Cell Transplantation, 2013 Oct. 21; DOI: 10.3727/096368913X673432; "Enabling Autologous Human Liver Regeneration With Differentiated Adipocyte Stem Cells"; the entirety of which, including figures, tables, supplementary figures, supplementary tables, etc., is hereby incorporated by reference). Although a few liver-specific genes (e.g. CYP3A4) were differentially expressed, the vast majority of genes had a similar level of expression in Chi-Heps and SCi-Heps, which indicates that both types of cells have a similar liver-specific gene expression profile.

Analysis of gene expression data. A micro-array-based analysis of global gene expression was performed on ASCs, Chi-Heps, SCi-Heps, iPS-Heps and hepatocytes. To eliminate the effect that inter-individual differences could have on the gene expression profile, ASCs, Chi-Heps, SCi-Heps and iPS-Heps were prepared from the same individuals. For our initial analysis, the hepatocyte and ASC gene expression profiles were compared to enable the selection of a set of genes that met pre-determined criteria (fold-change>5 and adjusted p value<0.01) for differential expression. To ensure that the subsequent comparisons were evaluating robust expression differences between ASCs and hepatocytes, we selected genes whose expression differences were greater than 5-fold. Based upon these criteria, this analysis identified 1,129 and 1,437 genes whose expression was increased or decreased, respectively, in hepatocytes relative to ASCs (e.g., as published in Table S2 in Xu et al., Cell Transplantation, 2013 Oct. 21; DOI: 10.3727/096368913X673432; "Enabling Autologous Human Liver Regeneration With Differentiated Adipocyte Stem Cells"; the entirety of which, including figures, tables, supplementary figures, supplementary tables, etc., is hereby incorporated by reference). To quantitatively assess the similarity between the 3 different types of iHeps and hepatocytes, we investigated how many of these selected genes also had an altered expression pattern after ASCs underwent the 3 different differentiation processes. For example, we found that the expression of 494 (or 44%) and 341 (or 24%) of the selected up- or down-regulated genes, respectively, were similarly altered in Chi-Heps (fold change >2 and adjusted p value<0.01) (FIG. 11). However, this result indicates that the level of expression of 1731 (or 67%) of these selected 2566 genes was either not significantly changed in Chi-Heps (relative to ASCs) or changed in a different direction (compared to hepatocytes). Similarly, we found using the same criteria that the expression of 565 (or 50%) and 449 (or 31%) of the selected up- or down-regulated genes, respectively, were similarly altered in SCi-Heps (FIG. 11); which indicates that the level of expression of 1552 (or 60%) of the selected 2566 genes was either not significantly changed in SCi-Heps or changed in a different direction. These results indicate that Chi- and SCi-Heps have a similar gene expression profile, which resembles, but certainly does not fully mirror, that of hepatocytes. Similar results emerged when this type of comparison was made using the iPS-Hep gene expression profile (FIG. 11). We also used a second approach to compare the global gene expression profiles measured in the 3 different types of iHeps. This time, we directly compared the gene expression profiles in Chi-Heps, SCi-Heps and iPS-Heps with that in ASCs, and examined the number of gene expression changes that were also consistently present in hepatocytes (relative to ASCs). This approach differs from that used above, since this comparison examines all genes that are differentially expressed in iHeps relative to ASCs. Out of 1487 genes that were differentially expressed (fold-change >2 and adjusted p value<0.01) in Chi-Heps relative to ASCs, 835 (56%) genes also showed consistent (and significant) expression changes in hepatocyte cells relative to ASCs (fold change >5 and p value<0.01). Similarly, out of 2372 genes that were differentially expressed in SCi-Heps, 1014 (43%) of these genes also showed consistent (and significant) expression changes in hepatocyte cells relative to ASCs. However, the same comparison performed using the iPS-Hep expression data revealed that only 31% (1372 out of 4456) of the differentially expressed genes in iPS-Heps showed consistent changes in hepatocytes. The differences in the iPS-Hep gene expression pattern are also exemplified by analysis of the genes whose expression pattern was not changed in hepatocytes relative to ASCs. Of the 16446 genes whose expression pattern was unchanged in hepatocytes relative to ASCs, the expression of 96% and 92% of these genes were also unchanged in Chi- and SCi-Heps, respectively (FIG. 11). However, the level of expression of 18% (or 2969) of these 16446 genes was altered in iPS-Heps. In summary, these analyses indicate that although their expression pattern does not fully reflect that of hepatocytes, Chi- and SCi-Heps have a gene expression pattern that better resembles that of hepatocytes than iPS-Heps. Moreover, there are a significant number of gene expression changes in iPS-Heps that are not reflective of that associated with hepatocyte differentiation.

Example 2

Human Liver Regeneration Using SCi-Heps

Figure 3A:
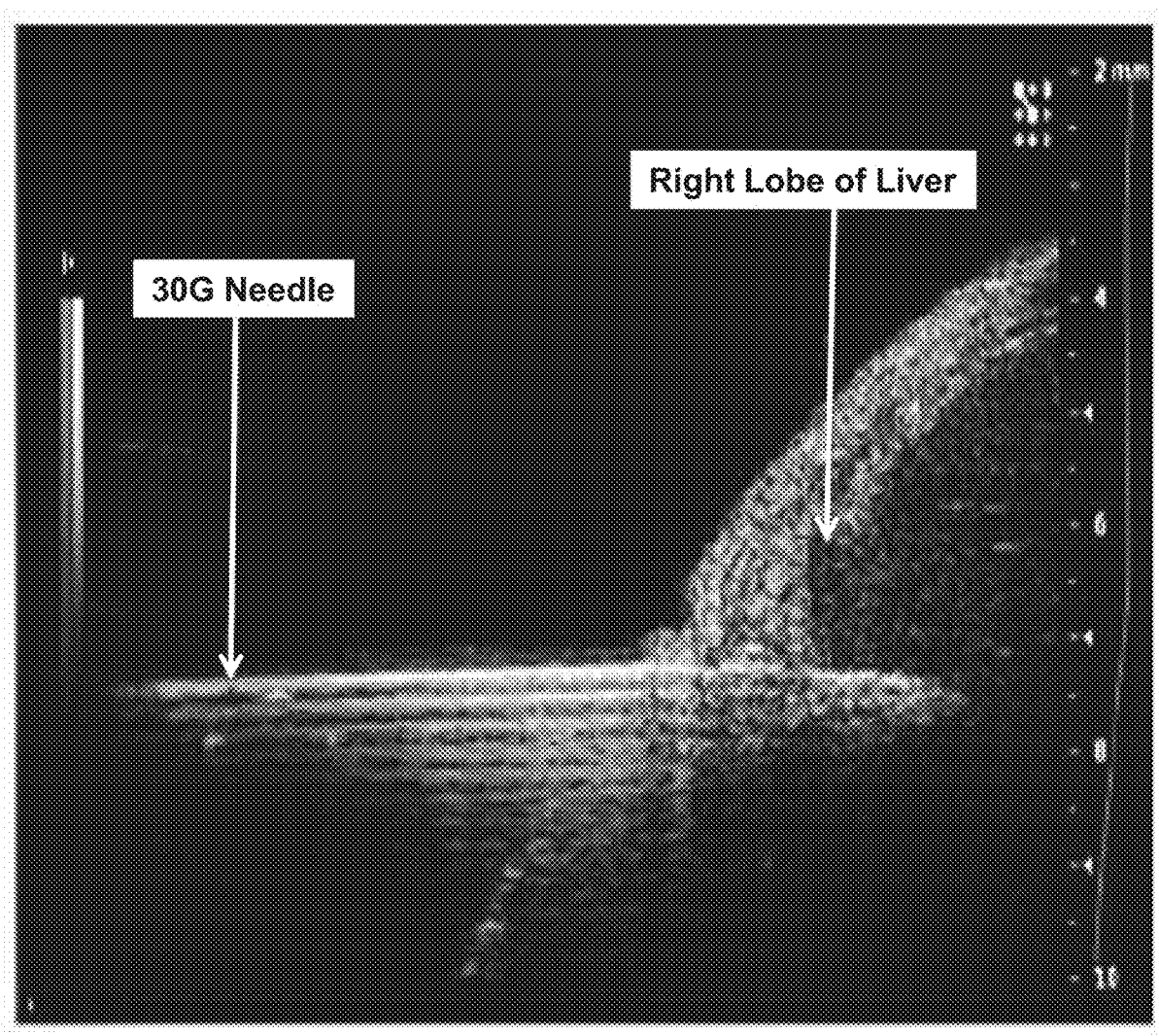
FIGS. 3A-3D demonstrate the implantation (via injection) of SCi-Heps into the mouse liver.
Figure 3B:
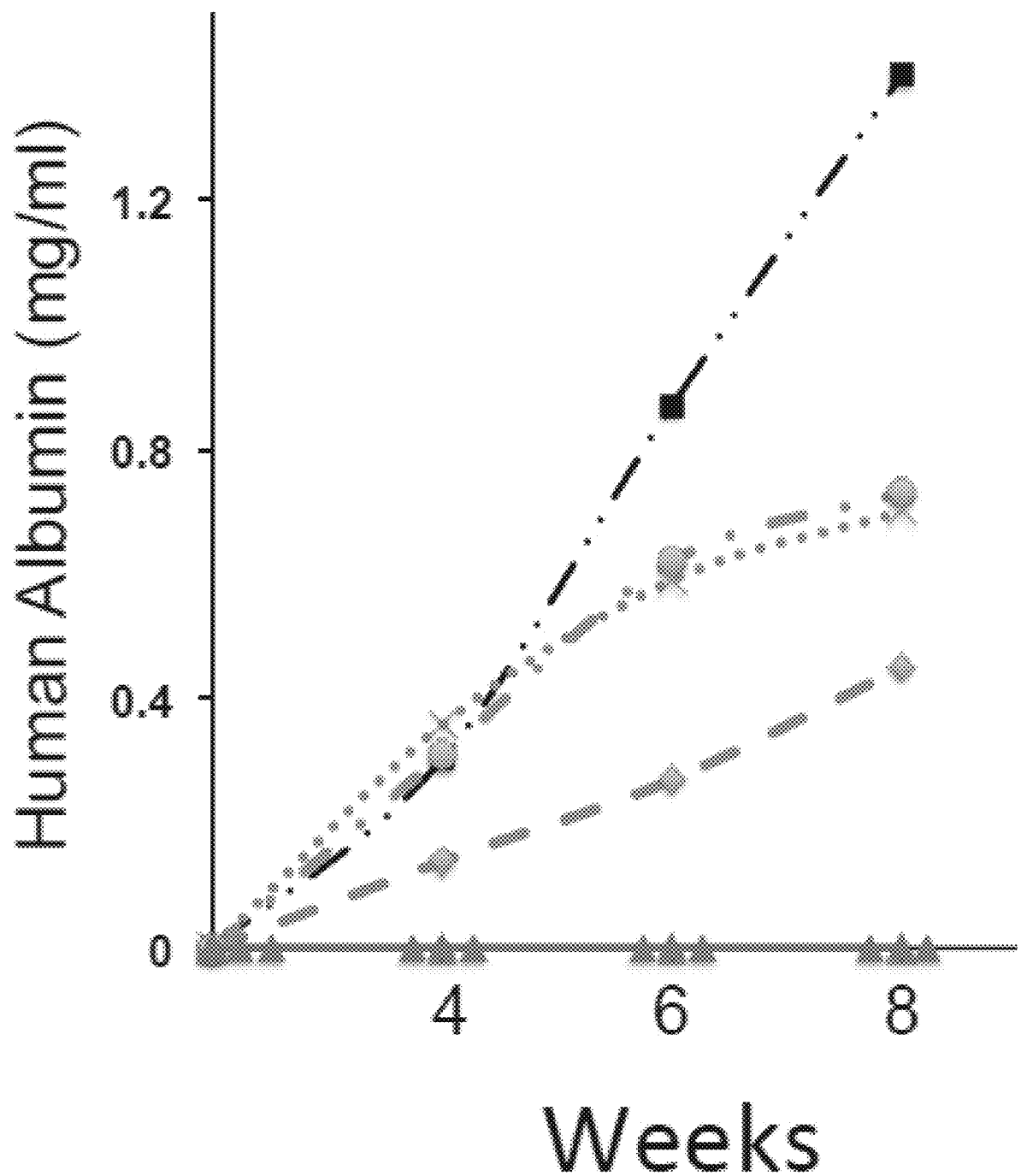

To determine whether SCi-Heps could reconstitute human liver in vivo, 5×106 SCi-Heps were transplanted by ultrasound-guided injection directly into the liver of four gancyclovir-conditioned TK-NOG mice (FIG. 3A). We previously demonstrated that the amount of human albumin in the sera of chimeric mice is an indicator of the extent of liver humanization (Hasegawa et al, Biochem Biophys Res Commun. 2011 Feb. 18; 405(3):405-10), so the serum human albumin level was serially assessed over an 8-week period after SCi-Heps transplantation. All four of these mice produced substantial and increasing amounts of human serum albumin when monitored over an 8-week period after transplantation. They had an average human albumin concentration of 0.29 (±0.09) mg/ml in their sera at 4 weeks, which increased to 0.82 (±0.41) at 8 weeks after SCi-Heps transplantation (FIG. 3B). In contrast, none of the 3 mice that were transplanted with the same number of undifferentiated ASCs produced detectable human serum albumin.

Figure 3C:
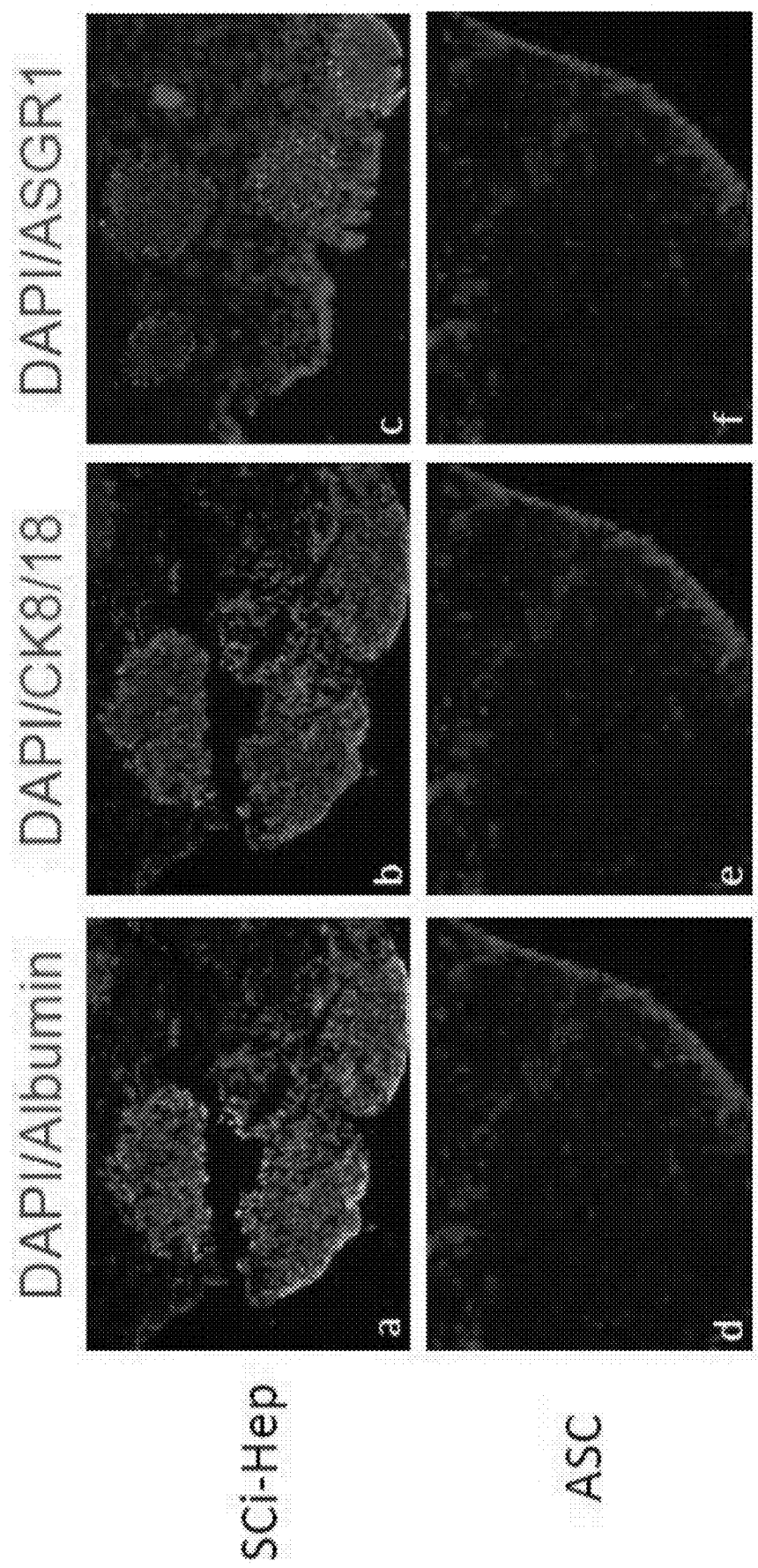
Figure 3D:
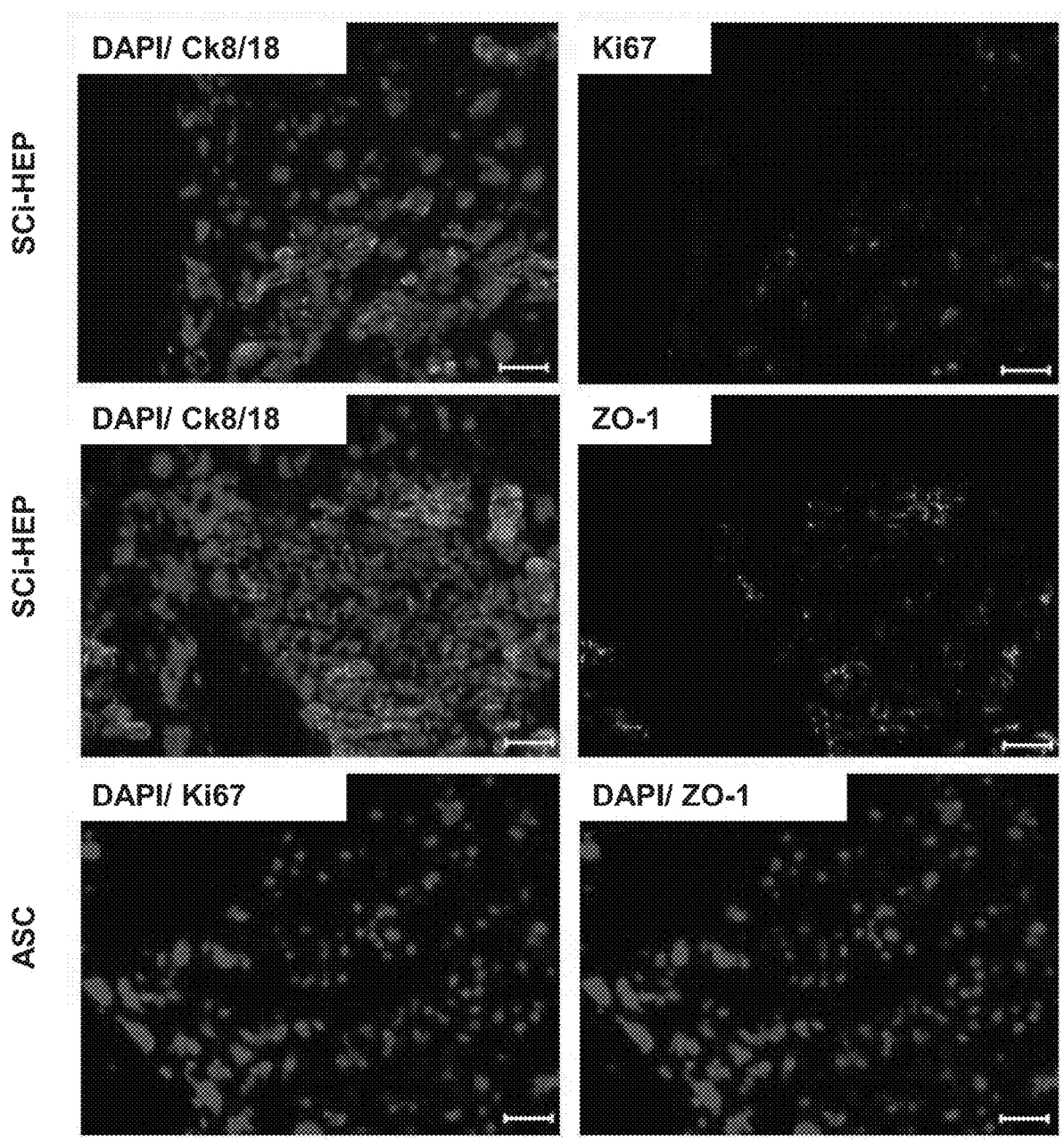
Figure 10:
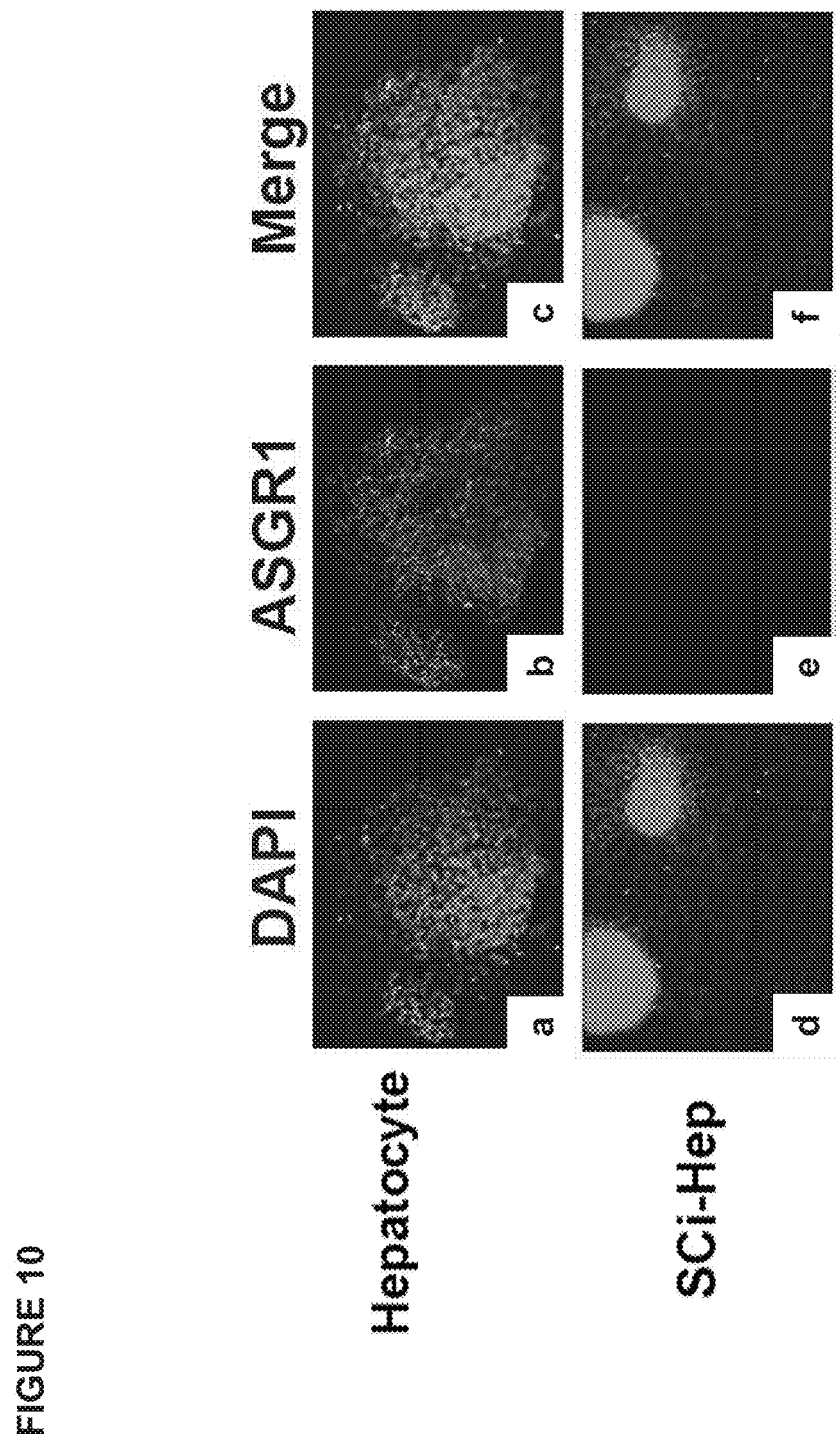
FIG. 10 demonstrates that SCi-Heps do not express ASGR-1 in vitro. Permeabilized human hepatocytes (a-c) or SCi-Heps (d-f), which were analyzed after 9 days of in vitro differentiation, were stained with an anti-human ASGR-1 antibody and counter-stained with DAPI. The immunofluorescence images (200× magnification) show that human hepatocytes, but not SCi-Heps expressed ASGR-1. The scale bars shown are 50 µm.

Liver histology revealed that the transplanted SCi-Heps integrated into the liver, produced human albumin, and expressed markers found on mature human hepatocytes (ASGR1, CK8/18) (FIG. 3C). Since SCi-Heps did not express ASGR1 in vitro just prior to transplantation (FIG. 10), ASGR1 expression indicated that the SCi-Heps continued to differentiate after liver engraftment. Since it was important to determine if the engrafted SCi-Heps would proliferate in the liver, we investigated whether the SCi-Heps expressed the Ki67 nuclear protein, which is a specific marker for cellular proliferation. A significant percentage of the engrafted SCi-Heps were Ki67 positive (FIG. 3D), which indicates that they proliferate in situ in the liver. In addition, a significant percentage of the engrafted SCi-Heps cells also expressed tight junction protein ZO-1 (FIG. 3D). This indicates that they have established tight junction interactions with one another, which is required for human bile duct formation. In contrast, livers obtained from mice that were transplanted with undifferentiated ASCs did not have any Ki67 or ZO-1 positive cells (FIG. 3D).

Figure 4A:
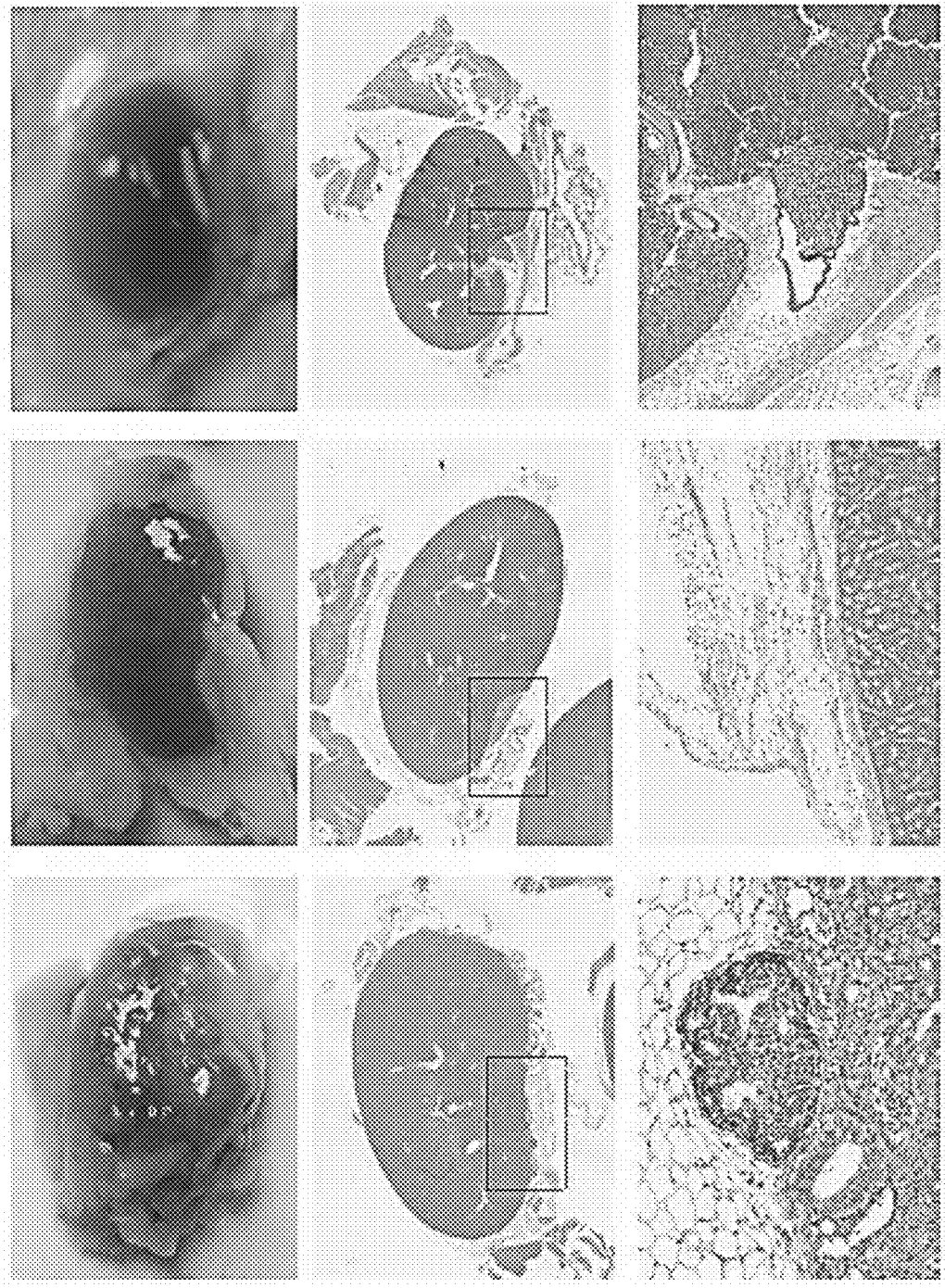
FIGS. 4A-4B demonstrate that SCi-Heps do not form tumors in immunocompromised mice, but iPS-Heps do.
Figure 4B:
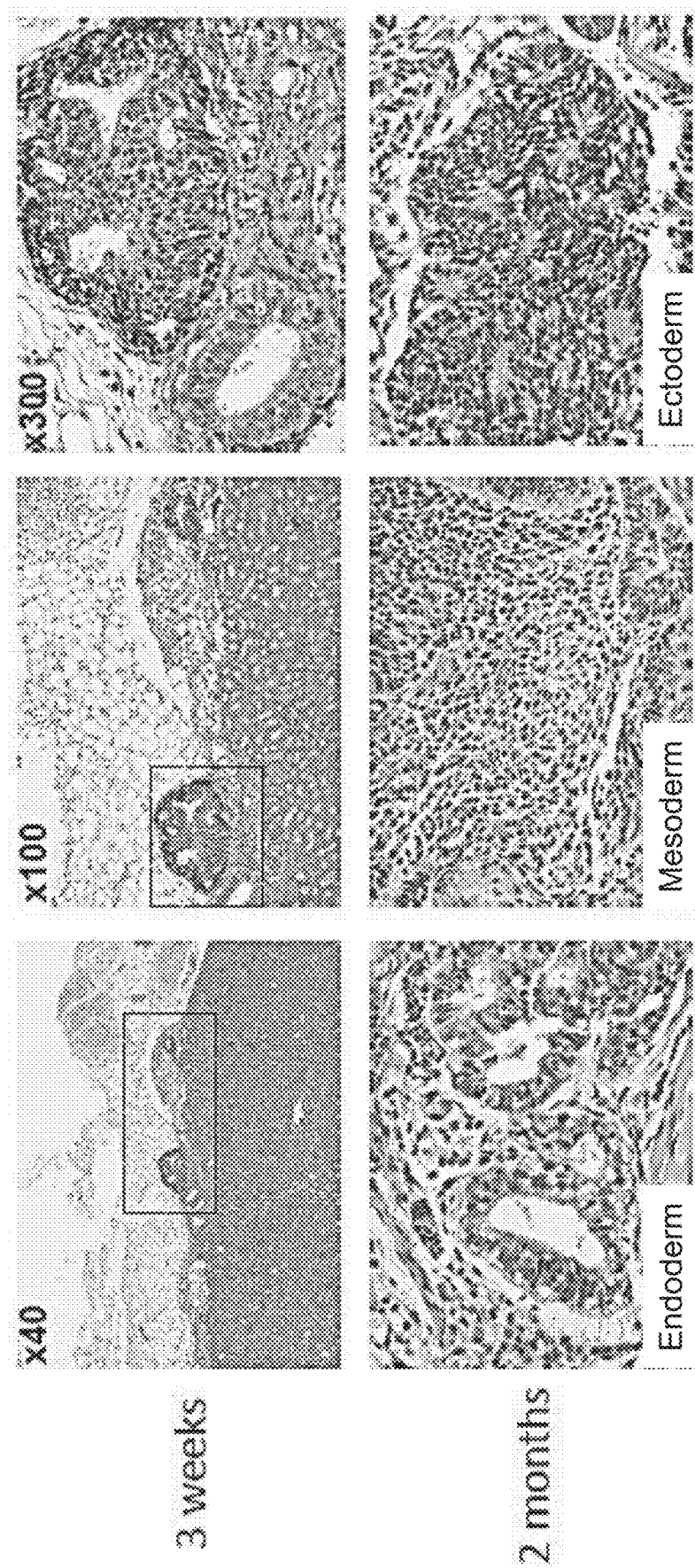

SCi-Heps do not form tumors. Because malignant potential is a critical determinant of whether SCi-Heps could be used for liver regeneration in human subjects, we examined whether SCi-Heps would form tumors after implantation under the kidney capsule of immunocompromised NOG mice. No tumors were formed over a 2-month observation period after $5 \times 10^4$ Chi- or SCi-Heps were implanted into each of 5 NOG mice. Moreover, analysis of tissue sections indicated that only normal tissue was present in the area of implantation. In contrast, implantation of the same number of iPS-Heps into each of 4 NOG mice resulted in the formation of multiple tumors within 3 weeks, which could be palpated through the body wall (FIG. 4A). Analysis of the tumor tissue obtained two months after iPS-Heps transplantation revealed that the tumors contained tissue derived from all 3 germ cell layers from all 4 mice (FIG. 4B).

Example 3

ASC Culture and iHep Formation Using Stirred Suspension Culture

ASCs were placed in spinner flask culture (in the absence of microcarriers) using numerous different rates of rotation, ranging from 0 to 150 rotations per minute (rpm). Culture conditions were identified that allowed ASCs to form aggregates and to proliferate. After 24 hours in the spinner flask system, the number of ASCs increased from $5 \times 10^5$ (starting cell number) to $7.7 \pm 0.3 \times 10^6$ (n=4 independent replicates) which is approximately a 14-fold increase in the number of cells. In contrast, a 6-fold increase in the number of ASCs (from $1 \times 10^4$ to $6.1 + 0.2 \times 10^4$) was obtained when ASCs were cultured for a 48-hour period using the hanging drop method (i.e., hanging drop suspension culture). Moreover, the morphology of the ASC cellular aggregates in the spinner flasks resembled the 'spheres' formed using the hanging drop method (FIG. 13).

Furthermore, the cellular aggregates were able to be differentiated to endoderm at similar efficiency as using the hanging drop method. These results indicate that high density culture (e.g., stirred suspension culture, e.g., spinner flask culture, bioreactor culture, etc.) will support the growth and proliferation of ASCs, that ASCs form cellular aggregates (e.g., spheres) even in the absence of microcarriers, and that ASCs can proliferate at a substantially greater rate in stirred suspension culture (e.g., spinner flasks). Thus, stirred suspension culture can provide a greater starting number of ASCs (e.g., prior to contact with a differentiation media), and a similar (or greater) differentiation efficiency as seen with hanging drop suspension culture (e.g., spinner flask culture, bioreactor culture, etc.), thereby producing a much larger total number of iHeps.

Figures 14A, 14B:
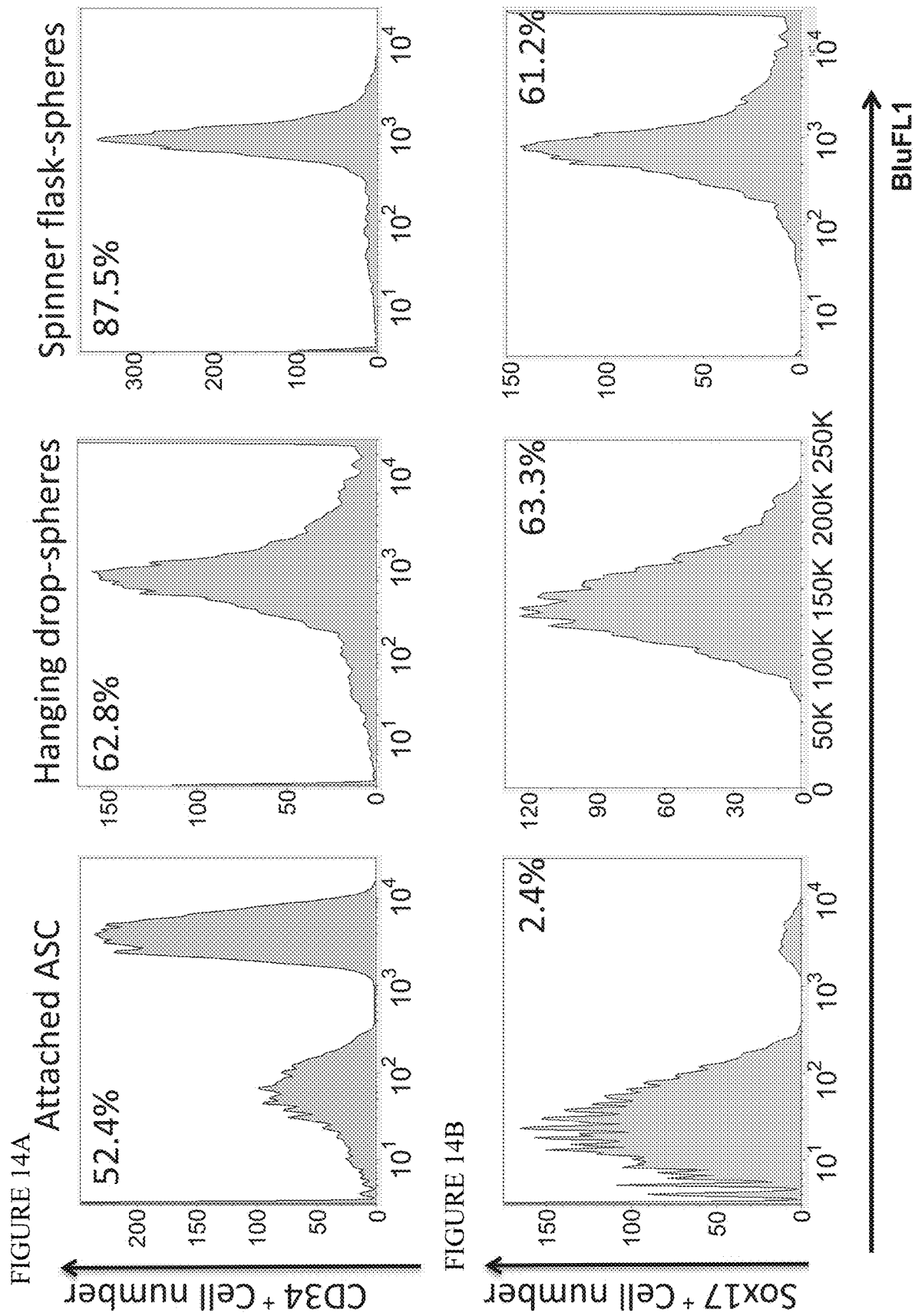
FIGS. 14A-14B demonstrate that ASCs cultured by stirred suspension culture (spinner flask culture in this case) form a greater percentage (FIG. 14A) of CD34+ cells (adipose stem cells) and a roughly equal percentage (FIG. 14B) of SOX17+ cells (endodermal precursor cells) compared to ASCs cultured by the hanging-drop method. X-axis is the intensity of signal detected.

ASCs cultured by attachment, and cellular aggregates (spheres) produced using (i) spinner flask culture (one day culture, in the absence of microcarriers), or (ii) hanging drop suspension culture (two days culture), were either: (1) stained with the ASC surface marker CD34, then analyzed for CD34 positive cells using fluorescent activated cell sorting (FACS) (FIG. 14A, Table 4); or (2) cultured in stage 1 medium for two days, them stained with endoderm marker Sox17 and analyzed for positive cells using FACS (FIG. 14B, Table 4). FIGS. 14A-B demonstrate that ASCs cultured by stirred suspension culture (in this case, spinner flask culture in the absence of microcarriers) form a greater percentage (A) of CD34+ cells (adipose stem cells) and a roughly equal percentage (B) of SOX17+ cells (endodermal precursor cells) compared to ASCs cultured by the hanging-drop method.

Table 4. This table demonstrates that ASCs cultured by stirred suspension culture (spinner flask culture in this case) form a greater percentage of CD34+ cells (adipose stem cells) and a roughly equal percentage of SOX17+ cells (endodermal precursor cells) compared to ASCs cultured by the hanging-drop method. Percentage is the percent of cells positive for expression of the marker.

TABLE 4

|  | Attached ASC | Hanging Drop | Spinner flask |
| --- | --- | --- | --- |
| CD34+ cells | 52.4% | 62.8% | 87.5% |
| SOX17+ cells | 2.4% | 63.3% | 61.2% |

Figure 15A:
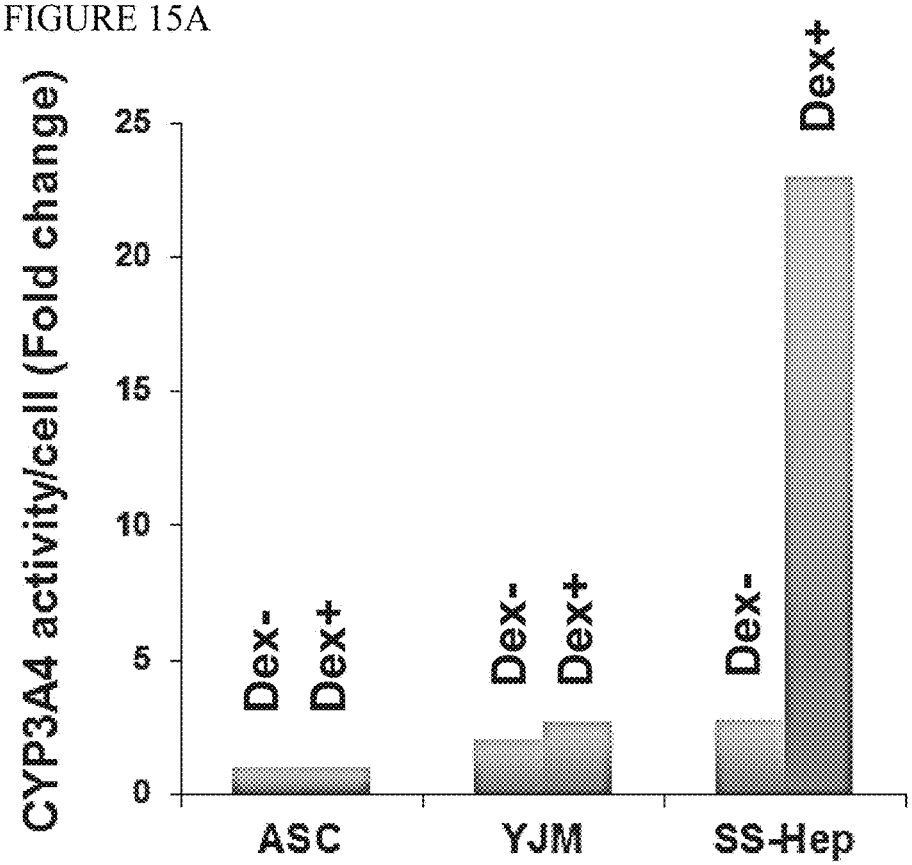
FIGS. 15A-15B demonstrate that iHeps produced using spinner flask culture (SS-Hep) had the specific cytochrome CYP enzymes CYP3A4 and CYP1A1, and the activity of CYP3A4 was strongly induced by dexamethasone (Dex) treatment. YJM is a human hepatocyte cell line. CYP activity was normalized to cell viability. Results are presented with (+) and without (−) Dex induction.
Figure 15B:
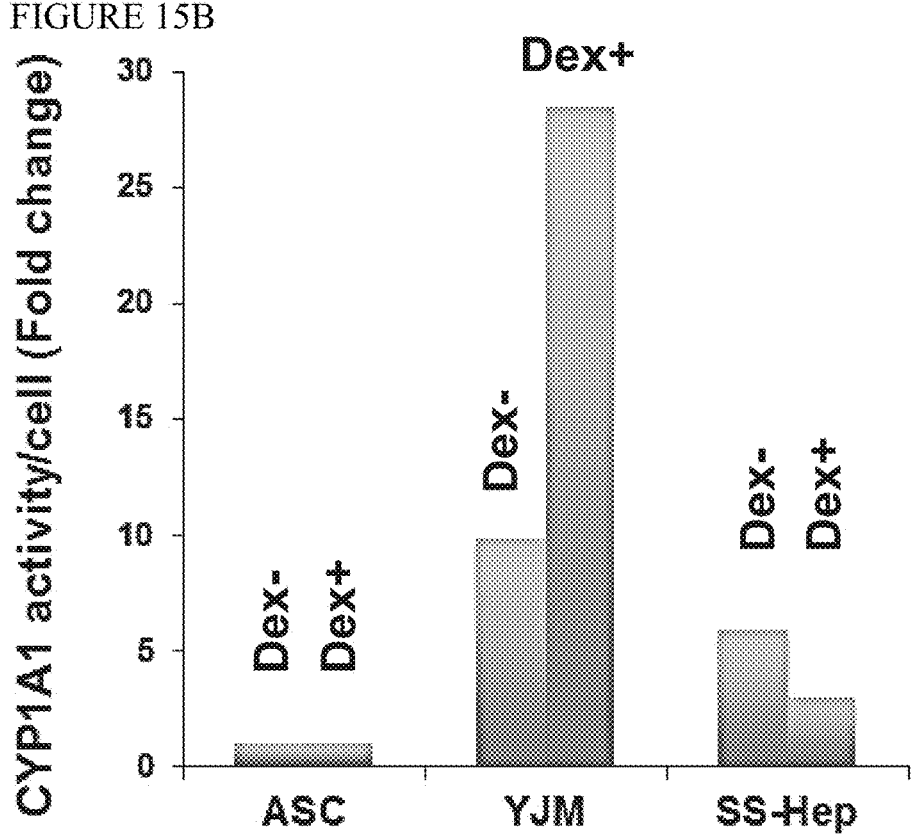

FIGS. 15A-B demonstrate that iHeps produced using spinner flask culture (SS-Hep) had the specific cytochrome CYP enzymes CYP3A4 and CYP1A1, and the activity of CYP3A4 was strongly induced by dexamethasone (Dex) treatment. YJM is a human hepatocyte cell line. CYP activity was normalized to cell viability. Results are presented with (+) and without (−) Dex induction.

Figure 16:
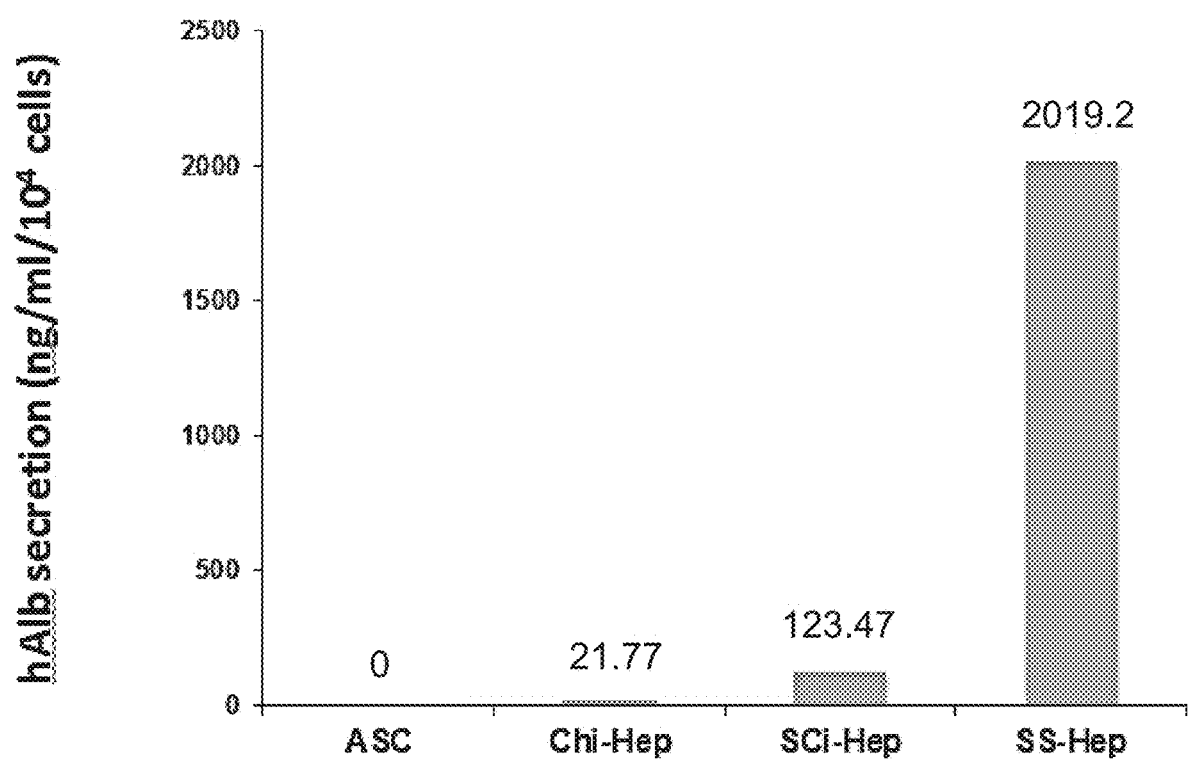
FIG. 16 demonstrates that iHeps produced using spinner flask culture (SS-Hep) secreted an increased level of human albumin (hAlb) compared to Chi-Heps and SCi-Heps (approximately 16-fold relative to SCi-Heps and approximately 96-fold relative to Chi-Heps).

FIG. 16 and Table 5 demonstrate that iHeps produced using spinner flask culture (SS-Hep) secreted an increased level of human albumin (hAlb) compared to Chi-Heps and SCi-Heps (approximately 16-fold relative to SCi-Heps and approximately 96-fold relative to Chi-Heps).

Table 5. This table demonstrates that iHeps produced using spinner flask culture (SS-Hep) secreted an increased level of human albumin (hAlb) compared to Chi-Heps and SCi-Heps (hAlb is in units of $ng/ml/10^4$ cells).

TABLE 5

|  | ASCs | Chi-Heps | SCi-Heps | SS-Heps |
| --- | --- | --- | --- | --- |
| hAlb secretion | 0 | 22 | 124 | 2019 |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A population of hepatocyte-like cells wherein the hepatocyte-like cells express CK8/18, albumin, alpha-antitrypsin 1 and Epcam but do not express CD105 and ASGR1.

2. A population of cells wherein at least 38% of the cells are hepatocyte-like cells and about 9% or less of the cells are adipose stem cells.

3. The population of cells of claim 2, wherein the hepatocyte-like cells are identified by expression of CK8/18.

4. The population of cells of claim 2, wherein the adipose stem cells are identified by expression of CD105.

5. The population of cells of claim 2, wherein the population of cells are derived from a population of adipose stem cells.

6. The population of cells of claim 2, wherein the hepatocyte-like cells further express albumin.

7. The population of cells of claim 2, wherein the hepatocyte-like cells do not express ASGR1.

8. A population of hepatocyte-like cells derived from adipocyte stem cells, wherein the cells express CK8/CK18, albumin, FoxA2, anti-alpha trypsin and Epcam.

9. The population of hepatocyte-like cells of claim 8, wherein greater than 20% of the cells express CK8/CK18.

10. The population of hepatocyte-like cells of claim 8, wherein about 20% to about 38% of the cells express CK8/CK18.

11. The population of hepatocyte-like cells of claim 8, wherein less than 9% of the cells in the population express CD105.

12. The population of hepatocyte-like cells of claim 8, wherein the cells do not express ASGR1.

* * * * *